US007498153B2

(12) United States Patent
Klein et al.

(10) Patent No.: US 7,498,153 B2
(45) Date of Patent: *Mar. 3, 2009

(54) CHIMERIC IMMUNOGENS

(75) Inventors: Michel H. Klein, Toronto (CA); Run-Pan Du, Thornhill (CA); Mary E. Ewasyshyn, Thornhill (CA)

(73) Assignee: Sanofi Pasteur Limited, Toronto, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 11/808,802

(22) Filed: Jun. 13, 2007

(65) Prior Publication Data

US 2008/0032342 A1 Feb. 7, 2008

Related U.S. Application Data

(60) Division of application No. 10/842,032, filed on May 10, 2004, now Pat. No. 7,244,589, which is a continuation of application No. 09/479,240, filed on Jan. 7, 2000, now abandoned, which is a continuation of application No. 08/467,961, filed on Jun. 6, 1995, now Pat. No. 6,171,783, which is a division of application No. 08/001,554, filed on Jan. 6, 1993, now Pat. No. 6,225,091.

(30) Foreign Application Priority Data

Jan. 6, 1992 (GB) ................................ 9200117.1

(51) Int. Cl.
*C12N 1/20* (2006.01)
*C12N 5/00* (2006.01)
*C12N 15/00* (2006.01)
*C12P 21/06* (2006.01)
*C07H 21/02* (2006.01)

(52) U.S. Cl. ................ 435/69.1; 435/252.3; 435/320.1; 435/325; 536/23.1

(58) Field of Classification Search ................ 536/23.1; 435/320.1, 69.1, 252.3, 325
See application file for complete search history.

(56) References Cited

U.S. PATENT DOCUMENTS

| 4,578,269 | A | 3/1986 | Morein |
| 4,722,848 | A | 2/1988 | Paoletti et al. |
| 4,866,034 | A | 9/1989 | Ribi |
| 4,879,213 | A | 11/1989 | Fox et al. |
| 4,950,480 | A | 8/1990 | Barber et al. |
| 5,098,998 | A | 3/1992 | Mekolanos et al. |
| 5,110,587 | A | 5/1992 | Paoletti et al. |
| 6,225,091 | B1 * | 5/2001 | Klein et al. ................ 435/69.3 |

FOREIGN PATENT DOCUMENTS

| EP | 0421626 | 4/1991 |
| WO | WO 89/05823 | 6/1989 |
| WO | WO 89/10405 | 11/1989 |
| WO | WO 90/03437 | 4/1990 |
| WO | WO 93/21310 | 10/1993 |

OTHER PUBLICATIONS

Kapikian et al, Am. J. Epidemiology 89, 1969, p. 405-421; An Epidemiologic Study of Altered Clinical Reactivity to Respiratory Syncytial (RS) Virus Infection in Children Previously Vaccinated With an Inactivated RS Virus Vaccine.
Belshe et al, J. Inf. Dis. 145, 1982, p. 311-319; Characteristics of the Amino Acids as Components of a Peptide Hormone Sequence.
Ray et al, (1989) Virus Research, 12:169-180.; Expression of the Fusion Glycoprotein of Human Parainfluenza Type 3 Virus in Insect Cells by a Recombinant Baculovirus and Analysis of its Immunogenic Property.
Coelingh et al, (1987) Virology 160:465-472; Expression of Biologically Active and Antigenically Authentic Parainfluenza Type 3 Virus Hemagglutinin-Neuraminidase Glycoprotein by a Recombinant Baculovirus.
Wathen et al, (1989) J. Of Inf. Dis. 159:255-263; Immunization of Cotton Rats With the Human Respiratory Synctial Virus F Glycoprotein Produced Using a Baculovirus Vector.
Spriggs et al, (1987), J. Virol. 61:3416-3423; Expression of the F and HN Glycoproteins of Human Parainfluenza Virus type 3 by Recombinant Vaccinia Viruses: Contributions of the Individual Proteins to Host Immunity.
Stott et al, (1987) J. Virol. 61:3855-3861.; Immune and Histopathological Responses in Animals Vaccinated With Recombinant Vacinia Viruses That Express Individual Genes of Human Respiratory Syncytial Virus.
Wathen et al (1989) J. Gen. Virol. 70:2625-2635; Characterization of a Novel Human Respiratory Syncytial Virus Chimeric FG Glycoprotein Expressed Using a Baculovirus Vector.
Connors et al (1992) Vaccine 10:475-484; Cotton Rats Previously Immunized With a Chimeric RSV FG Glycoprotein Develop Enhanced Pulmonary Pathology When Infected With RSV, a Phenomenon not Encountered Following Immunization With Vaccinia—RSV Recombinants or RSV.
Perkus et al (1989) J. Virology 63:3829-3836; Cloning and Expression of Foreign Genes in Vaccinia Virus, Using a Host Range Selection System.
Goebel et al, (1990) Virology 179:247-266; The Complete DNA Sequence of Vaccinia Virus.
Perkus et al (1990) Virology 179:276-286; Vaccinia Virus Host Range Genes.
Goebel et al (1990) Virology 179:517-563; Appendix to "The Complete DNA Sequence of Vaccinia Virus".
Targaglia et al (1992) Virology 188:217-232; NYVAC: A Highly Attenuated Strain of Vaccinia Virus.
Piccini et al (1987) Methods in Enzymology, 153:545-563; Vaccinia Virus as an Expression Vector.

(Continued)

*Primary Examiner*—Mark Navarro
(74) *Attorney, Agent, or Firm*—Michael I. Stewart; Sim & McBurney

(57) ABSTRACT

Multimeric hybrid genes encoding the corresponding chimeric protein comprise a gene sequence coding for an antigenic region of a protein from a first pathogen linked to a gene sequence coding for an antigenic region of a protein from a second pathogen. The pathogens particularly are parainfluenza virus (PIV) and respiratory syncytial virus (RSV). A single recombinant immunogen is capable of protecting infants and similar susceptible individuals against diseases caused by both PIV and RSV.

16 Claims, 39 Drawing Sheets

OTHER PUBLICATIONS

Taylor et al, (1990) J. Virology 64:1441-1450; Newcastle Disease Virus Fusion Protein Expressed in a Fowlpox Virus Recombinant Confers Protection in Chickens.

Collins et al (1990) J. Virology 64:4007-4012; O Glycosylation of Glycoprotein G of Human Respiratory Syncytial Virus is Specified Within the Divergent Ectodomain.

Vijaya et al—Mol. Cell. Biol. Vol. 8: No. 4 (1988) pp. 1709-1714; Transport of the Cell Surface of a Peptide Sequence Attached to the Truncated C Terminus of an N-Terminally Anchored Integral Membrane Protein.

Ray et al, Journal of Virology, pp. 783-787—Mar. 1988; Role of Individual Glycoproteins of Human Parainfluenza Virus Type 3 in the Induction of a Protective Immune Response.

Stover et al, Nature 351:456-460 (1991); New Use of BCG for Recombinant Vaccines.

Olmstead et al PNAS 83, 7462-7466 (1986); Expression of the F Glycoprotein of Respiratory Syncytial Virus by a Recombinant Vaccinia Virus: Comparison of the Individual Contributions of the F and G Glycoproteins to Host Immunity.

Chanock et al, Pediatrics vol. 90, No. 1, Jul. 1992; Serious Respiratory Tract Disease Caused by Respiratory Syncytial Virus: Prospects for Improved Therapy and Effective Immunization.

Murphy et al, Experimental Lung Research 2:97-109 (1981); The Cotton Rat as an Experimental Model of Human Parainfluenza Virus Type 3 Disease.

Porter et al, J. Of Virology, Jan. 1991—vol. 65:No. 1, pp. 103-111; Pathogenesis of Human Parainfluenza Virus 3 Infection in Two Species of Cotton Rats: Sigmodon Hispidus Develops Bronchiolitis, While Sigmodon Fulviventer Develops Interstitial Pneumonia.

Prince et al, Am. J. Of Pathology, vol. 93, No. 3; pp. 771-783; The Pathogenesis of Respiratory Syncytial Virus Infection in Cotton Rats.

Prince et al, J. Of Virology 57:721-728; Enhancement of Respiratory Syncytial Virus Pulmonary Pathology in Cotton Rats by Prior Intramuscular Inoculation of Formalin-Inactivated Virus.

Tizard, I. "An Introduction to Veterinary Immunology",—2nd Edition—published by W.B. Saunders Company (1982), pp. 123-124.; An Introduction to Veterinary Immunology.

Hall et al, Science 265:1393-1399 (1994)L; Prospects for a Respiratory Syncytial Virus Vacine.

Bowie et al, Science 247: 1306-1310 (1990); Deciphering the Message in Protein Sequences: Tolerance to Amino Acid Substitutions.

Kumar et al, PNAS 87:1337-1341 (1990); Amino Acid Variations at a Single Residue in an Autoimmune Peptide Profoundly Affect its Propreties: T-Cell Activation, Major Histocompatibility Complex Binding, and Ability to Block Experimental Allergic Encephalomyelitis.

Lazar et al, Molecular and Cellular Biology, 8(3):1247-52 (1988); Transforming Growth Factor a: Mutation of Aspartic Acid 47 and Leucine 48 Results in Different Biological Activities.

Burgess et al, Journal of Cell Biology 111:2129-38 (1990); Possible Dissociation of the Heparin-Binding and Mitogenic Activities of Heparin-Binding (Acidic Fibroblast) Growth Factor-1 From its Receptor-Binding Activities by Site-Directed Mutagenesis of a Single Lysine Residue.

Sallgaller et al, Cancer Immunology Immunotherapy 39: 105:116—1994.

Coelingh et al, J. Virol. 64(8):3833-43 (see abstract)—1990; Antibody Responses of Humans and Nonhuman Primates to Individual Antigenic Sites of the Hemagglutinin-Neuraminidase and Fusion Glycoproteins After Primary Infection or Reinfection With Parainfluenza Type 3 Virus.

Hendry et al, J. Gen. Virol. 66(8):1705-14—1985; Quantification of Respiratory Syncytial Virus Polypeptides in NASLA Secretions by Monoclonal Antibodies.

Rudinger et al, See Chapter 1, pp. 1-6 of "Peptide Hormones" J.A. Parsons et al (ed.) published by U. Park Press (Baltimore)—1976; Characteristics of the Amino Acids as Components of a Peptide Hormone Sequence.

Brideau et al, J. Gen. Virol. 70: 2637-2644—1989; Protection of Cotton Rats Against Human Respiratory Syncytial Virus by Vaccination With a Novel Chimeric FG Glycoprotein.

Kasel et al, Journal of Virology, Dec. 1984, pp. 828-832—vol. 52, No. 3; Acquisition of Serum Antibodies to Specific Viral Glycoproteins of Parainfluenza Virus 3 in Children.

* cited by examiner

FIG.1A. NUCLEOTIDE SEQUENCE OF THE PIV-3 F GENE (PCR-AMPLIFIED)

```
AAGTCAATACCAACAACTATTAGCAGTCATACGTGCAAGAACAAGAAAGAAGAGATTCAA
TTCAGTTATGGTTGTTGATAATCGTCAGTCAGTATGCACGTTCTTGTTCTTTCTCTAAGTT
         10        20        30        40        50        60

AAAGCTAAATAAGAGAAATCAAACAAAAGGTATAGAACACCCGAACAACAAAATCAAAA
TTTCGATTTATTCTCTTTAGTTTTGTTTTCCATATCTTGTGGGCTTGTTGTTTTAGTTTT
         70        80        90       100       110       120

CATCCAATCCATTTTAAACAAAATTTGTTTTTAAGGTTTCTCTTGGCCGTTGTTCGTGGTTTG
GTAGGTTAGGTAAAATTTGTTTTTAAGGTTTCTCTTGGCCGTTGTTCGTGGTTTG
         130       140       150       160       170       180
                           SP
            MET PRO THR [LEU] ILE LEU LEU ILE ILE THR THR MET ILE MET ALA [SER] SER CYS GLN
ACAATGCCAACTTTAATACTGCTAATTATTACAACAATGATTATGGCATCTTCCTGCCAA
TGTTACGGTTGAAATTATGACGATTAATAATGTTGTTACTAATACCGTAGAAGGACGGTT
         190       200       210       220       230       240

ILE ASP ILE THR LYS LEU GLN HIS VAL GLY VAL LEU VAL ASN SER PRO LYS GLY MET LYS
ATACACAAAAACTACAGCATGGTGTATTGGTCAACAGTCCAAAGGGATGAAG
TATGTATAGTGTTTGATGTCGTACCATCCACAGTTGTCAGGGTTTCCCTACTTC
         250       260       270       280       290       300

ILE SER GLN ASN PHE GLU THR ARG TYR LEU ILE LEU SER LEU ILE PRO LYS ILE GLU ASP
ATATCACAAAACTTCGAAACTAGATATCTAATTTGAGCCTCATACCAAAATAGAAGAC
TATAGTGTTTTGAAGCTTTGATCTATAGATTAAACTCGGAGTATGGTTTTATCTTCTG
         310       320       330       340       350       360

SER ASN SER CYS GLY ASP GLN GLN ILE LYS GLN TYR LYS ARG LEU LEU ASP ARG LEU ILE
TCTAACTCTTGTGGTGACCAACAGATCAAACAAGAGTTATTGGATAGACTGATC
AGATTGAGAACACCACTGGTTGTCTAGTTTGTTCCAATAACCTATCTGACTAG
         370       380       390       400       410       420
```

FIG. 1B.

```
          ILE PRO LEU TYR ASP GLY LEU ARG LEU GLN LYS ASP VAL ILE VAL  THR  ASN GLN GLU SER
          ATCCCTCTATATGATGGATTAAGATTACAGAAAGATGTGATAGTAACCAATCAAGAATCC
          TAGGGAGATATACTACCTAATTCTAATGTCTTTCTACACTATCATTGGTTAGTTCTTAGG
                       430           440           450           460           470           480

F2-F1 CLEAVAGE SITE
          ASN GLU ASN THR ASP PRO ARG THR  ARG   ARG ↓ SER  PHE GLY GLY VAL ILE GLY THR ILE ALA
          AATGAAAACACTGATCCCAGAACAAGACGATCTCCTAGGAGGGGTAATTGGAACCATTGCT
          TTACTTTTGTGACTAGGGTCTTGTTCTGCTAGAGGATCCTCCCCATTAACCTTGGTAACGA
                       490           500           510           520           530           540

LEU GLY VAL ALA THR SER ALA GLN ILE THR ALA ALA LEU VAL ALA GLU ALA LYS GLN
          CTGGGAGTAGCAACCTCAGCACAAATTACAGCGGCAGTTGCTCTGGTTGAAGCCAAGCAG
          GACCCTCATCGTTGGAGTCGTGTTTAATGTCGCCGTCAACGAGACCAACTTCGGTTCGTC
                       550           560           570           580           590           600

ALA  LYS  SER ASP ILE THR ILE ARG ARG LEU LYS GLU ALA LYS ALA VAL GLN
          GCAAAATCACACAGATCACAATCAGAAGAAGCAATCAGGACACAAAGCAAGCAGTGCAG
          CGTTTTAGTGTGTCTAGCTTTTGAGTCTTCTTCGTTAGTCCTGTGTTTCGTTCGTCACGTC
                       610           620           630           640           650           660

SER VAL GLN SER SER ILE GLY ASN LEU ILE VAL ALA ILE LYS SER VAL GLN ASP TYR VAL
          TCAGTTCAGTCTTCTATAGGCAATCTGATTGTTGCTATAAATCAGTCCAAGATTATGTC
          AGTCAAGTCAGAAGATATCCGTTAGACTAACAACGATATTTAGTCAGGTTCTAATACAG
                       670           680           690           700           710           720

ASN  ASN  GLU ILE VAL PRO SER ILE ALA ARG LEU GLY CYS GLU ALA ALA GLY LEU GLN LEU
          AACAACGAAATCGTGCCATCGATTGCTAGACTAGGTTGTGAAGCAGGACTTCAATTA
          TTGTTGCTTTTAGCACGGTAGCTAACGATCTGATCCAACACTTCGTCCTGAAGTTAAT
                       730           740           750           760           770           780

GLY ILE ALA LEU THR GLN HIS TYR SER GLU LEU THR ASN ILE PHE GLY ASP ASN ILE GLY
          GGAATTGCATTAACACAGCATTACTCAGAATTAACAAACATATTTGGTGATAACATAGGA
          CCTTAACGTAATTGTGTCGTAATGAGTCTTAATTGTTTGTATAAACCACTATTGTATCCT
                       790           800           810           820           830           840
```

FIG.1C.

```
SER LEU GLN GLU LYS GLY ILE LYS LEU GLN GLY ILE ALA SER LEU TYR ARG THR ASN ILE
TCGTTACAAGAGAAGGAATTAAAATTACAAGGTATAGCATCATTATACCGCACAAATATC
AGCAATGTTCTTTTTCCTTATTTTAATGTTCCATATCGTAGTAATATGGCGTGTTTATAG
        850                 860                 870                 880                 890                 900

THR GLU ILE PHE THR THR SER THR VAL ASP LYS TYR ASP ILE ASP LEU LEU PHE THR
ACAGAAATATTCACAACAAGTAGTTGATAAATATGATATCGATCTATTATTTACA
TGTCTTTATAAGTGTTGTTCAACTACAGTTGTAGTCTATAGATAATAAATGT
        910                 920                 930                 940                 950                 960

GLU SER ILE LYS VAL ARG VAL ILE ASP VAL ASP LEU ASN ASP TYR SER ILE THR LEU GLN
GAATCAATAAAGGTGAGAGTTATAGATGTTGATTTGAATGATTACTCAATCACCCTCCAA
CTTAGTTATTTCCACTCTCAATATCTACAACTAAACTTACTAATGAGTTAGTGGGAGGTT
        970                 980                 990                1000                1010                1020

VAL ARG LEU PRO LEU LEU THR ARG LEU LEU ASN THR GLN ILE TYR [LYS] VAL ASP SER ILE
GTCAGACTCCCTTATTAACTAGGCTGCTGAACACTCAGATCTACAAGTAGATTCCATA
CAGTCTGAGGGAATAATTGATCCGACGACTTGTGAGTCTAGATGTTCATCTAAGGTAT
       1030                1040                1050                1060                1070                1080

SER TYR ASN ILE GLN ASN ARG GLU TRP TYR ILE PRO LEU PRO SER HIS ILE MET THR LYS
TCATATAATATCCAAACAGAGAATGGTATATCCCTCTTCCCAGCCATATCATGACGAAA
AGTATATTATAGGTTTGTCTCTTACCATATAGGGAGAAGGGTCGGTATAGTACTGCTTT
       1090                1100                1110                1120                1130                1140

GLY ALA PKE LEU GLY GLY ALA ASP VAL LYS GLU CYS ILE GLU ALA PHE SER SER TYR ILE
GGGGCATTTCTAGGTGGAGCAGATGTCAAGGAATGTATAGAAGCATTCAGCAGTTATATA
CCCCGTAAAGATCCACCTCGTCTACAGTTCCTTACATATCTTCGTAAGTCGTCAATATAT
       1150                1160                1170                1180                1190                1200

CYS PRO SER ASP PRO GLY PHE VAL LEU ASN HIS GLU KET GLU SER CYS LEU SER GLY ASN
TGCCCCTTCTGATCCAGGATTTGTACTAAACCATGAAATGGAGAGCTGCTTATCAGGAAC
ACGGGAAGACTAGGTCCTAAACATGATTTGGTACTTTACCTTCGACGAATAGTCCTTTG
       1210                1220                1230                1240                1250                1260
```

FIG. 1D.

```
ILE SER GLN CYS PRO ARG THR [THR] VAL [THR] SER ASP ILE VAL PRO ARG TYR ALA PHE VAL
ATATCCCAATGTCCAAGAACCACGGTCACATCAGACATTGTTCCAAGATATGCATTCGTC
      1270              1280              1290              1300              1310              1320
TATAGGGTTACAGGTTCTTGGTGCCAGTGTAGTCTGTAACAAGGTTCTATACGTAAGCAG

ASN GLY GLY VAL VAL ALA ASN CYS ILE THR THR THR CYS THR CYS ASN GLY ILE [ASP] ASN
AATGGAGGAGTGGTTGCAAACTGTATAACAACCACCTGTACATGCAACGGAATCGACAAT
      1330              1340              1350              1360              1370              1380
TTACCTCCTCACCAACGTTTGACATATTGTTGGTGGACATGTACGTTGCCTTAGCTGTTA

ARG ILE ASN GLN PRO PRO ASP GLN GLY VAL LYS ILE ILE THR HIS LYS CYS ASN THR
AGAATCAATCAACCACCTGATCAAGGAGTAAAATATAACATAAAGAATGTAATACA
      1390              1400              1410              1420              1430              1440
TCTTAGTTAGTTGGTGGACTAGTTCCTCATTTTAATATTGTATTTCTTACATTATGT

ILE GLY ILE ASN GLY MET LEU PHE ASN THR ASN LYS GLU GLY THR LEU ALA PHE TYR THR
ATAGGTATCAACGGAATGCTGTTCAATACAAATAAAGAAGGAACTCTTGCATTCTACACA
      1450              1460              1470              1480              1490              1500
TATCCATAGTTGCCTTACGACAAGTTATGTTTATTTCTTGAGAACGTAAGATGTGT

PRO ASN ASP ILE THR LEU ASN ASN SER VAL ALA LEU ASP PRO ILE ASP ILE SER ILE GLU
CCAAATGATATAACACTAAATAATTCTGTTGCACTTGATCCAATTGACATATCAATCGAG
      1510              1520              1530              1540              1550              1560
GGTTTACTATATTGTGATTTATTAAGACAACGTGAACTAGGTTAACTGTATAGTTAGCTC

LEU ASN LYS ALA LYS SER ASP LEU GLU GLU SER LYS GLU TRP ILE ARG ARG SER ASN GLN
CTTAACAAAGCCAAATCAGATCTAGAAGAATCAAAAGAATGGATAAGAAGGTCAAATCAA
      1570              1580              1590              1600              1610              1620
GAATTGTTTCGGTTTAGTCTAGATCTTCTTAGTTTTCTTACCTATTCTTCCAGTTAGTT
                                                                                              TM

LYS LEU ASP SER ILE GLY ASN TRP HIS GLN SER SER THR THR ILE ILE ILE [ILE] LEU ILE
AAACTAGATTCTATTGGAAACTGGCATCAATCTAGCACTACAATCATAATTATTTTAATA
      1630              1640              1650              1660              1670              1680
TTTGATCTAAGATAACCTTTGACCGTAGTTAGATCGTGATGTTAGTATTAATAAAATTAT
```

FIG.1E

```
MET ILE ILE ILE LEU PHE ILE ILE ASN VAL THR ILE ILE [THR] ILE ALA [ILE] LYS TYR TYR
ATGATCATTATATTGTTTATAATTAATGTAACGATAATTACAATTGCAATTAAGTATTAC
TACTAGTAATATAACAAATATTAATTACATTGCTATTAATGTTAACGTTAATTCATAATG
         1690      1700      1710      1720      1730      1740

ARG ILE GLN LYS ARG ASN ARG VAL ASP GLN ASN ASP LYS PRO TYR VAL LEU THR ASN LYS
AGAATTCAAAAGAGAAATCGAGTGGATCAAAATGACAAGCCATATGTACTAACAAACAAA
TCTTAAGTTTTCTCTTTAGCTCACCTAGTTTTACTGTTCGGTATACATGATTGTTTGTTT
         1750      1760      1770      1780      1790      1800

TGACATATCTATAGATCATTAGATATTAAAATTATAAAAAACTT
ACTGTATAGATATCTAGTAATCTATAATTTTAATATTTTTTGAA
         1810      1820      1830      1840
```

NUCLEOTIDE SEQUENCE OF THE PIV-3 F GENE. THE cDNA SEQUENCE IS SHOWN IN THE PLUS (mRNA) STRAND SENSE IN THE 5' TO 3' DIRECTION. THE SIGNAL PEPTIDE (SP) AND THE TRANSMEMBRANE (TM) ANCHOR DOMAIN ARE UNDERLINED. THE PREDICTED F2-F1 CLEAVAGE SITE IS INDICATED BY THE ARROW (↓). AMINO ACIDS DIFFERING FROM THE PUBLISHED PRIMARY SEQUENCE OF THE PROTEIN ENCODED BY THE PIV-3 F GENE ARE BOXED.

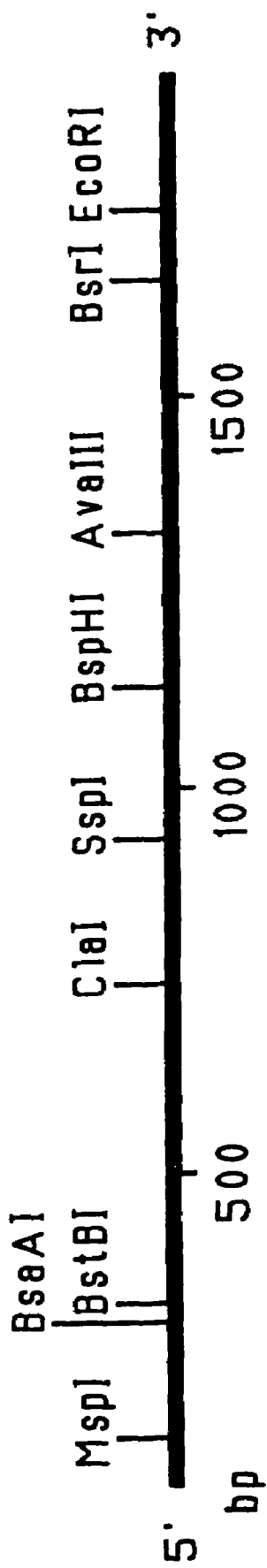

FIG.3A. NUCLEOTIDE SEQUENCE OF THE PIV-3 HN GENE.

```
                    MET GLU TYR TRP LYS HIS THR ASN HIS GLY LYS ASP ALA GLY
5' AGACAAATCCAAATTCGAGATGGAATACTGGAAGCATACCAATCACGGAAAGGATGCTGG
   TCTGTTTAGGTTTAAGCTCTACCTTATGACCTTCGTATGGTTAGTGCCTTTCCTACGACC 60
                    10            20            30            40            50

ASN LYS  ILE THR TYR
   ASN GLU LEU GLU THR SER MET ALA THR [ASN] GLY ASN LYS [LEU] THR
   CAATGAGCTGGAGACGTCCATGGCTACTAATGGCAACAAGCTCACCAATAAGATAACATA
   GTTACTCGACCTCTGCAGGTACCGATGATTACCGTTGTTCGAGTGGTTATTCTATTGTAT 120
                    70            80            90            100           110

ILE LEU TRP THR ILE ILE ILE VAL LEU LEU SER ILE ILE VAL PHE ILE ILE VAL LEU ILE ASN
   TATATTATGGACAATAATCCTGGTTATTATCAATAGTCTTCATCATAGTAGTGCTAATTAA
   ATATAATACCTGTTATTAGGACCACAATAATAGTTATCAGAAGTAGTATCACGATTAATT 180
                    130           140           150           160           170      TM→

SER ILE LYS SER GLU LYS ALA HIS GLU SER LEU LEU GLN ASP ASN [ILE] ASN ASN GLU PHE MET
   TTCCATCAAAAAGTGAAAAGGCTCATGAATCATTGCTGCAAGACAATATAAATAATGAGTTTAT
   AAGGTAGTTTTCACTTTCCGAGTACTTAGTAACGACGTTCTGTTATTATTACTCAAATA 240
                    190           200           210           220           230

GLU [ILE] THR GLU LYS ILE GLN MET ALA SER ASP ASN [THR] ASN ASP LEU ILE GLN SER GLY
   GGAAATTACAGAAAAGATCCAAATGGCATCGGATAATACCAATGATCTAATACAGTCAGG
   CCTTTAATTGTCTTTTCTAGGTTTACCGTAGCCTATTATGGTTACTAGATTATGTCAGTCC 300
                    250           260           270           280           290

VAL ASN THR ARG LEU LEU THR ILE GLN SER HIS VAL GLN ASN TYR ILE PRO ILE SER LEU
   AGTGAATACAAGGCTTCTTACAATTCAGAGTCATGTCCAGAATTATATACCAATATCACT
   TCACTTATGTTCCGAAGAATGTTAAGTCTCAGTACACAGGTCTTAATATATATGGTTATAGTGA 360
                    310           320           330           340           350
```

```
                THR GLN GLN MET SER ASP LEU ARG LYS PHE ILE SER GLU ILE THR ILE ARG ASN ASP ASN
              GACACAACAGATGTCAGATCTTAGGAAATTCATTAGTGAAATTACAATTAGAAATGATAA
              CTGTGTTGTCTACAGTCTAGAATCCTTTAAGTAATCACTTTAATGTTAATCTTTACTATT
                               380                   390                  400                 410                 420

GLN GLU VAL LEU PRO GLN ARG ILE THR HIS ASP VAL GLY ILE LYS PRO LEU ASN PRO ASP
              TCAAGAAGTGCTGCCACAAAGAATAACACATGATGTGGGTATAAAACCTTTAAATCCAGA
              AGTTCTTCACGACGGTGTTTCTTATTGTGTACTACACCCATATTTTGGAAATTTAGGTCT
                              430                   440                  450                 460                   480

ASP PHE TRP ARG CYS THR SER GLY LEU PRO SER LEU PRO SER MET LYS THR PRO LYS ILE ARG LEU
              TGATTTTTGGAGATGCACGTCTGGTCTTCCATCTCTTAATGAAAACTCCAAAAATAAGGTT
              ACTAAAAACCTCTACGTGCAGACCAGAAGGTAGAGAATTACTTTTGAGTTTTATTCCAA
                              490                   500                  510                 520                 530                 540

MET PRO GLY PRO GLY LEU LEU ALA MET PRO THR THR VAL ASP GLY CYS ILE ARG THR PRO
              AATGCCAGGGCCGGGCCCCGGGATTATTAGCCATGCCAACGACTGTTGATGGCTGTATCAGAGAACTCC
              TTACGGTCCCGGCCCGGGCCCTAATAATCGATACGGTTGCTGACAACTACCGACATAGTCTTGAGG
                               550                  560                  570                 580                 590                 600

SER LEU VAL ILE ASN ASP LEU ILE TYR ALA TYR THR SER ASN LEU THR ARG GLY CYS
              GTCCTTAGTTATAAATGATCTAGATTTATGCTTATACCTCAAATCTAATTACTCGAGGTTG
              CAGGAATCAATATTTACTAGACTAAATACGAATATGGAGTTTAGATTAATGAGCTCCAAC
                               610                  620                  630                 640                 650                  660

GLN ASP ILE GLY LYS SER TYR GLN VAL LEU GLN ILE GLY ILE ILE THR VAL ASN SER ASP
              TCAGGATATAGGAAAAATCATCAAGTCTTACAGATCTTCATATCCCTATTATTGACAGTCTTAAACTCAGA
              AGTCCTATATCCTTTTAGTAGTTCAGAATGTCTAGAGTATAGGATAATAACTGTCAGAATTTGAGTCT
                               670                  680                  690                 700                 710                 720

LEU VAL PRO ASP LEU ASN PRO ARG ILE SER HIS THR PHE ASN ILE ASN ASP ASN ARG LYS
              CTTGGTACCTGACTTAAATCCCAGGATCTCTCATACTTTAACATAAATGACAATAGGAA
              GAACCATGGACTGAATTTAGGGTCCTAGAGAGTATGAAAATTGTATTTACTGTTATCCTT
              730                   740                   750                 760                 770                 780
```

FIG.3B.

```
SRE CYS SER LEU LEU ALA LEU LEU ASN THR ASP VAL TYR GLN LEU CYS SER THR PRO LYS VAL
GTCATGTTCTCTAGCACTCCTAAATACAGATGTATATATAGTCAACTGTTCAACTCCCAAAGT
CAGTACAAGAGATCGTGAGGATTTATGTCTACATATATCAGTTGACACAAGTTGAGGTTTCA
                 790                800               810                820                830                840

ASP GLU ARG SER ASP TYR ALA SER SER GLY ILE VAL LEU ASP ILE VAL ASN
TGATGAAAGATCAGATTATGCATCATCAGGCATAGAAGATATTGTACTTGATATTGTCAA
ACTACTTTCTAGTCTAATACGTAGTAGTCCGTATCTTCTATAACATGAACTATAACAGTT
       850               860               870               880               890               900

TYR ASP GLY SER ILE SER THR THR ARG PHE LYS ASN ASN ILE SER PHE ASP GLN PRO
TTATGATGGCTCAATCTCAACAACAAGATTTAAGAATAACATAAGCTTTGATCAACC
AATACTACCGAGTTAGAGTTGTTGTTCTAAATTCTTATTGTATTCGAAACTAGTTGG
         910               920               930               940               950               960

TYR ALA ALA LEU TYR PRO SER VAL GLY PRO GLY ILE TYR TYR LYS ILE ILE PHE
TTATGCTGCACTATACCCATCTGTTGGACCAGGGATATACTACAAAGGCAAAATAATATT
AATACGACGTGATATGGGTAGGCAGACAACCTGGTCCCTATATGATGTTTCCGTTTTATAA
         970               980               990               1000              1010              1020

LEU GLY TYR GLY GLY LEU GLU HIS PRO ILE ASN GLU ASN VAL ILE CYS ASN THR THR GLY
TCTCGGGTATGGAGGTCTTGAACATCCAATAAATGAGAATGTAATCTGCAACACTACTGG
AGAGCCCATACCTCCAGAACTTGTAGGTTATTTACTCTTACATTAGACGTTGTGTTGACC
           1030                1040                1050                1060                1070                1080

CYS PRO GLY LYS THR GLN ARG ASP CYS ASN GLN ALA SER HIS SER PRO TRP PHE SER ASP
GTGTCCCGGGAAAACACAGAGAGACTGCAATCAGGCATCTCATAGTCCATGGTTTCAGA
CACAGGGCCCTTTTGTGTCTCTCTGACGTTAGTCCGTAGAGTATCAGGTACCAAAAGTCT
          1090              1100              1110              1120              1130              1140

ARG ARG MET VAL ASN SER ILE ILE VAL VAL ASP LYS GLY LEU ASN SER ILE PRO LYS LEU
TAGGAGGATGGTCAACTCTATCATTGTTGTTGACAAAGGCTTAAACTCAATTCCAAAATT
ATCCTCCTACCAGTTGAGATAGTAACAACTGTTTCCGAATTTGAGTTAAGGTTTTAA
         1150              1160              1170              1180              1190              1200
```

```
     LYS VAL TRP THR ILE SER MET ARG GLN ASN TYR TRP GLY SER GLU GLY ARG LEU LEU LEU
    GAAGGTATGGACGATATCTATGAGACAGAATTACTGGGGGTCAGAAGGAAGGAAGGTTACTTCT
    CTTCCATACCTGCTATAGATACTCTGTCTTAATGACCCCAGTCTTCCTTCCAATGAAGA
                      1210              1220              1230              1240              1250          1260

LEU GLY ASN LYS ILE TYR ILE TYR THR ARG SER THR TRP HIS SER LYS LEU GLN LEU
    ACTAGGTAACAAGATCTATATATATACAAGATCCACAAGTTGGCATAGCAAGTTACAATT
    TGATCCATTGTTCTAGATATATATATGTTCTAGGTGTTCAACCGTATCGTTCAATGTTAA
                      1270              1280              1290              1300              1310              1320

GLY ILE ILE ASP THR ILE THR ASP TYR SER ASP ILE ARG ILE LYS TRP THR TRP HIS ASN VAL
    AGGAATAATTGATACTATTACTGATTACAGTGATATAAGGATAAAATGGACATGGCATAATGT
    TCCTTATTAACTATGATAATGACTAATGTCACTATATTCCTATTTTACCTGTACCGTATTACA
                      1330              1340              1350              1360              1370              1380

LEU SER ARG PRO GLY ASN ASN GLU CYS PRO TRP GLY HIS SER CYS PRO ASP GLY CYS ILE
    GCTATCAAGACCAGGTAACAATGAATGTCCATGGGGACATTCATGTCCAGATGGATGTAT
    CGATAGTTCTGGTCCATTGTTACTTACAGGTACCCCTGTAAGTACAGGTCTACCTACATA
                      1390              1400              1410              1420              1430              1440

THR GLY VAL TYR THR ASP ALA TYR PRO LEU ASN PRO THR GLY SER ILE VAL SER SER VAL
    AACAGGAGTATATACTGATGCATATCCACTCAATCCCACAGGGAGCATTGTGTCATCTGT
    TTGTCCTCATATATGACTACGTATAGGTGAGTTAGGGTGTCCCTCGTAACACAGTAGACA
                      1450              1460              1470              1480              1490              1500

ILE LEU ASP SER GLN LYS SER ARG VAL ASN PRO VAL ILE THR TYR SER THR [ALA] THR GLU
    CATATTAGATTCACAAAAATCGAGAGTGAACCAGTCATAACTTACTCAACAGCAACCGA
    GTATAATCTAAGTGTTTTTAGCTCTCACTTGGTCAGTATTGAATGAGTTGTCGTTGGCT
                      1510              1520              1530              1540              1550              1560

ARG VAL ASN GLU LEU ALA ILE [ARG] ASN ARG THR LEU SER ALA GLY TYR THR THR THR SER
    AAGAGTAAACGAGCTGCTCGACCGAGAACAGAACACTCTCAGCTGGATATACAACAAG
    TTCTCATTTGCTCGACGGAGCTGGCTTGTCTTGTGAGAGTCGACCTATATGTTGTTGTTC
                      1570              1580              1590              1600              1610              1620
```

```
      CYS ILE THR HIS TYR ASN LYS GLY TYR CYS PHE HIS ILE VAL GLU ILE ASN GLN LYS SER
      CTGCATCACACACTATAACAAAGGATATTGTTTCATATAGTAGAAATAAATCAGAAAAG
      GACGTAGTGTGTGATATTGTTTCCTATAACAAAAGTATATCATCTTTATTTAGTCTTTTC
                      1630              1640              1650              1660              1670              1680

LEU ASN THR LEU GLN PRO MET LEU PHE LYS THR GLU VAL PRO LYS SER CYS SER ***
      CTTAAACACACTTCAACCATGTTGTTCAAGACAGAGGTTCCAAAAAGCTGCAGTTAATC
      GAATTTGTGTGAAGTTGGGTACAACAAGTTCTGTCTCCAAGGTTTTTCGACGTCAATTAG
                      1690              1700              1710              1720              1730              1740

ATAATTAACCGCAATATGCATTAACCTATCTATAATACAAGTATATGATAAGTAATCAGC
      TATTAATTGGCGTTATACGTAATTGGATAGATATTATGTTCATATACTATTCATTAGTCG
                      1750              1760              1770              1780              1790              1800

AATCAGACAATAGACAAAAGGGAAATATAAAAA
      TTAGTCTGTTATCTGTTTTCCCTTTATATTTTT
                      1810              1820              1830
```

NUCLEOTIDE SEQUENCE OF THE PIV-3 HN GENE. THE cDNA SEQUENCE
IS SHOWN IN THE PLUS (mRNA) STRAND SENSE IN THE 5' TO 3'
DIRECTION. THE TRANSMEMBRANE (TM) ANCHOR DOMAIN IS UNDERLINED. AMINO ACIDS DIFFERING FROM THE PUBLISHED PRIMARY SEQUENCE OF THE PROTEIN ENCODED BY THE PIV-3 HN GENE ARE BOXED.

FIG.3E.

FIG. 5A.  NUCLEOTIDE SEQUENCE OF THE RSV F GENE.

```
         SP
         ────────▶
5' MET GLU LEU [PRO] ILE LEU LYS ALA ASN ALA ILE THR THR ILE LEU ALA [ALA] VAL THR PHE
   ATG GAG TTG CCA ATC CTC AAA GCA AAT GCA ATT ACC ACA ATC CTC GCT GCA GTC ACA TTT
                        10                  20                  30                  40                  50                  60
   ACC CTC AAC GGT TAG GAG TTT CGT TAA TGG TGT TAG GAG CGA CGT CAG TGT AAA

CYS PHE ALA [SER] SER GLN ASN ILE THR GLU GLU PHE TYR GLN SER THR CYS SER ALA VAL
TGC TTT GCT TCT AGT CAA GAA ACA TCA CTG AAG AAT TTT ATC AAT CAA CAT GCA GTG CAG TT
                70                  80                  90                 100                 110                 120
ACG AAA CGA AGA TCA GTT CTT TGT AGT GAC TTC TTA AAA TAG TTA GTT GTA CGT CAC GTC AA

SER LYS GLY TYR LEU SER ALA LEU ARG THR GLY TRP TYR THR TYR THR SER VAL ILE THR ILE GLU
AGC AAA GGC TAT CTT AGT GCT CTA AGA ACT GGT TGG TAT ACT AGT GTT ATA ACT ATA GAA
               130                 140                 150                 160                 170                 180
TCG TTT CCG ATA GAA TCA CGA GAT TCT TGA CCA ACC ATA TGA TCA CAA TAT TGA TAT CTT

LEU SER ASN ILE LYS GLU ASN LYS CYS ASN GLY THR ASP ALA LYS VAL LYS LEU [MET] LYS
TTA AGT AAT ATC AAG GAA AAT AAG TGT AAT GGA ACA GAT GCT AAG GTA AAA TTG ATG AAA
               190                 200                 210                 220                 230                 240
AAT TCA TTA TAG TTC CTT TTA TTC ACA TTA CCT TGT CTA CGA TTC CAT TTT AAC TAC TTT

GLN GLU LEU ASP LYS TYR LYS ASN ALA VAL THR GLU LEU GLN LEU LEU MET GLN SER THR
CAA GAA TTA GAT AAA TAT AAA AAT GCT GTA ACA GAA TTG CAG TTG CTC ATG CAA AGC ACA
               250                 260                 270                 280                 290                 300
GTT CTT AAT CTA TTT ATA TTT TTA CGA CAT TGT CTT AAC GTC AAC GAG TAC GTT CGT GT

PRO [ALA] [ALA] ASN ASN ARG ALA ARG ARG GLU LEU PRO ARG PHE MET ASN TYR THR LEU ASN
CCA GCA GCA AAC AAT CGA GCC AGC AGA GAA CTA CCA AGG TTT ATG AAT TAT ACA CTC AAC
               310                 320                 330                 340                 350                 360
GGT CGT CGT TTG TTA GCT CGG TCG TCT CTT GAT GGT TCC AAA TAC TTA ATA TGT GAG TTG
```

```
        LEU ILE ALA VAL GLY LEU LEU LEU TYR CYS LYS ALA ARG SER THR PRO VAL THR LEU SER
        TTAATTGCTGTTGGACTGCTCCTATACTGTCTAAGGCCAGAAGCACACCAGTCACACTAAGC
        AATTAACGACAACCTGACGAGGATATGACATTCCGGTCTTCGTGTGGTCAGTGTGATTCG
                   1630                1640                1650                1660                1670                1680

LYS, ASP GLN LEU SER GLY ILE ALA PHE SER ASN
        AGGATCAACTGAGTGGTATAAATAATATTGCATTTAGTAACTGAATAAAAAATAGCACCT
        TCCTAGTTGACTCACCATATTTATTATAACGTAAATCATTGACTTATTTTATCGTGGA
                   1690                1700                1710                1720                1730                1740

AATCATGTTCTTACAATGGTTTACTATCTGCTCATAGACAACCCATCTATCATTGGATTT
        TTAGTACAAGAATGTTACCAAATGATAGACGAGTCTGTTGGGTAGATAGTAACCTAAA
                   1750                1760                1770                1780                1790                1800

TCTTAAAATCTGAAACTTCATCGAAACTCTTATCTATAAACCATCTCACTTACACTATTTA
        AGAATTTTAGACTTGAAGTAGCTTTGAGATAGATATTTGGTAGAGTGAATGTGATAAAT
                   1810                1820                1830                1840                1850                1860

AGTAGATTCCTAGTTTATAGTTATAT 3'
        TCATCTAAGGATCAAATATCAATATA
                   1870                1880

NUCLEOTIDE SEQUENCE OF THE RSV F GENE.THE cDNA SEQUENCE IS SHOWN IN THE PLUS (mRNA)
        STRAND SENSE IN THE 5' TO 3' DIRECTION.THE SIGNAL PEPTIDE (SP) AND THE TRANSMEMBRANE (TM)
        ANCHOR DOMAIN ARE UNDERLINED.THE PREDICTED F2-F1 CLEAVAGE SITE IS INDICATED BY THE ARROW
        (↓).AMINO ACIDS DIFFERING FROM THE PUBLISHED PRIMARY SEQUENCE OF THE PROTEIN ENCODED BY
        THE RSV F GENE ARE BOXED.
```

FIG.5E.

RESTRICTION MAP OF THE RSV F GENE

FIG.7A. NUCLEOTIDE SEQUENCE OF THE RSV G GENE

```
      MET   SER   LYS   ASN   LYS   ASP   GLN   ARG
T G C A A A C A T G T C C A A A A A C A A G G A C C A A C G
A C G T T T G T A C A G G T T T T T G T T C C T G G T T G C
         10                  20                  30

THR   ALA   LYS   THR   LEU   GLU   [LYS]  THR   TRP   ASP
C A C C G C T A A G A C A C T A G A A A A G A C C T G G G A
G T G G C G A T T C T G T G A T C T T T T C T G G A C C C T
         40                  50                  60

THR   LEU   ASN   HIS   LEU   LEU   PHE   ILE   SER   SER
C A C T C T C A A T C A T T T A T T A T T C A T A T C A T C
G T G A G A G T T A G T A A A T A A T A A G T A T A G T A G
         70                  80                  90
                                                       ←
   [GLY]  LEU   TYR   LYS   LEU   ASN   LEU   LYS   SER   VAL
G G G C T T A T A T A A G T T A A A T C T T A A A T C T G T
C C C G A A T A T A T T C A A T T T A G A A T T T A G A C A
        100                 110                 120
─────────────── TM ───────────────
   ALA   GLN   ILE   THR   LEU   SER   ILE   LEU   ALA   MET
A G C A C A A A T C A C A T T A T C C A T T C T G G C A A T
T C G T G T T T A G T G T A A T A G G T A A G A C C G T T A
        130                 140                 150
─────────────────────────────────────────────────
   ILE   ILE   SER   THR   SER   LEU   ILE   ILE   [THR]  ALA
G A T A A T C T C A A C T T C A C T T A T A A T T A C A G C
C T A T T A G A G T T G A A G T G A A T A T T A A T G T C G
        160                 170                 180
─────────────────────────────────────────────────→
   ILE   ILE   PHE   ILE   ALA   SER   ALA   ASN   HIS   LYS
C A T C A T A T T C A T A G C C T C G G C A A A C C A C A A
G T A G T A T A A G T A T C G G A G C C G T T T G G T G T T
        190                 200                 210

VAL   THR   [LEU]  THR   THR   ALA   ILE   ILE   GLN   ASP
A G T C A C A C T A A C A A C T G C A A T C A T A C A A G A
T C A G T G T G A T T G T T G A C G T T A G T A T G T T C T
        220                 230                 240

ALA   THR   SER   GLN   ILE   LYS   ASN   THR   THR   PRO
T G C A A C A A G C C A G A T C A A G A A C A C A A C C C C
A C G T T G T T C G G T C T A G T T C T T G T G T T G G G G
        250                 260                 270

THR   TYR   LEU   THR   GLN   [ASP]  PRO   GLN   LEU   GLY
A A C A T A C C T C A C T C A G G A T C C T C A G C T T G G
T T G T A T G G A G T G A G T C C T A G G A G T C G A A C C
        280                 290                 300
```

FIG.7B.

```
    ILE   SER   PHE   SER   ASN   LEU   SER   GLU   ILE   THR
    A A T C A G C T T C T C C A A T C T G T C T G A A A T T A C
    T T A G T C G A A G A G G T T A G A C A G A C T T T A A T G
              310                 320                 330

SER   GLN   THR   THR   THR   ILE   LEU   ALA   SER   THR
    A T C A C A A A C C A C C A C C A T A C T A G C T T C A A C
    T A G T G T T T G G T G G T G G T A T G A T C G A A G T T G
              340                 350                 360

THR   PRO   GLY   VAL   LYS   SER   ASN   LEU   GLN   PRO
    A A C A C C A G G A G T C A A G T C A A A C C T G C A A C C
    T T G T G G T C C T C A G T T C A G T T T G G A C G T T G G
              370                 380                 390

THR   THR   VAL   LYS   THR   LYS   ASN   THR   THR   THR
    C A C A A C A G T C A A G A C T A A A A A C A C A A C A A C
    G T G T T G T C A G T T C T G A T T T T T G T G T T G T T G
              400                 410                 420

THR   GLN   THR   GLN   PRO   SER   LYS   PRO   THR   THR
    A A C C C A A A C A C A A C C C A G C A A G C C C A C T A C
    T T G G G T T T G T G T T G G G T C G T T C G G G T G A T G
              430                 440                 450

LYS   GLN   ARG   GLN   ASN   LYS   PRO   PRO   ASN   LYS
    A A A A C A A C G C C A A A A C A A A C C A C C A A A C A A
    T T T T G T T G C G G T T T T G T T T G G T G G T T T G T T
              460                 470                 480

PRO   ASN   ASN   ASP   PHE   HIS   PHE   GLU   VAL   PHE
    A C C C A A T A A T G A T T T T C A C T T C G A A G T G T T
    T G G G T T A T T A C T A A A A G T G A A G C T T C A C A A
              490                 500                 510

ASN   PHE   VAL   PRO   CYS   SER   ILE   CYS   SER   ASN
    T A A C T T T G T A C C C T G C A G C A T A T G C A G C A A
    A T T G A A A C A T G G G A C G T C G T A T A C G T C G T T
              520                 530                 540

ASN   PRO   THR   CYS   TRP   ALA   ILE   CYS   LYS   ARG
    C A A T C C A A C C T G C T G G G C T A T C T G C A A A A G
    G T T A G G T T G G A C G A C C C G A T A G A C G T T T T C
              550                 560                 570

ILE   PRO   ASN   LYS   LYS   PRO   GLY   LYS   LYS   THR
    A A T A C C A A A C A A A A A A C C A G G A A A G A A A A C
    T T A T G G T T T G T T T T T T G G T C C T T T C T T T T G
              580                 590                 600
```

FIG.7C.

```
    THR  THR  LYS  PRO  THR  LYS  LYS  PRO  THR  PHE
    C A C C A C C A A G C C T A C A A A A A A C C A A C C T T
    G T G G T G G T T C G G A T G T T T T T T G G T T G G A A
              610                 620                 630

LYS  THR  THR  LYS  LYS  ASP  [LEU] LYS  PRO  GLN
    C A A G A C A A C C A A A A A A G A T C T C A A A C C T C A
    G T T C T G T T G G T T T T T T C T A G A G T T T G G A G T
              640                 650                 660

THR  THR  LYS  [PRO] LYS  GLU  VAL  PRO  THR  THR
    A A C C A C T A A A C C A A A G G A A G T A C C C A C C A C
    T T G G T G A T T T G G T T T C C T T C A T G G G T G G T G
              670                 680                 690

LYS  PRO  THR  GLU  GLU  PRO  THR  ILE  ASN  THR
    C A A G C C C A C A G A A G A G C C A A C C A T C A A C A C
    G T T C G G G T G T C T T C T C G G T T G G T A G T T G T G
              700                 710                 720

THR  LYS  THR  ASN  ILE  [THR] THR  THR  LEU  LEU
    C A C C A A A A C A A A C A T C A C A A C T A C A C T G C T
    G T G G T T T T G T T T G T A G T G T T G A T G T G A C G A
              730                 740                 750

THR  [ASN] ASN  THR  THR  GLY  ASN  PRO  [LYS] LEU
    C A C C A A C A A C A C C A C A G G A A A T C C A A A A C T
    G T G G T T G T T G T G G T G T C C T T T A G G T T T T G A
              760                 770                 780

THR  SER  GLN  MET  GLU  THR  PHE  HIS  SER  THR
    C A C A A G T C A A A T G G A A A C C T T C C A C T C A A C
    G T G T T C A G T T T A C C T T T G G A A G G T G A G T T G
              790                 800                 810

SER  SER  GLU  GLY  ASN  [LEU] SER  PRO  SER  GLN
    C T C C T C C G A A G G C A A T C T A A G C C C T T C T C A
    G A G G A G G C T T C C G T T A G A T T C G G G A A G A G T
              820                 830                 840

VAL  SER  THR  THR  SER  GLU  [HIS] PRO  SER  GLN
    A G T C T C C A C A A C A T C C G A G C A C C C A T C A C A
    T C A G A G G T G T T G T A G G C T C G T G G G T A G T G T
              850                 860                 870

PRO  SER  SER  PRO  PRO  ASN  THR  [THR] ARG  GLN
    A C C C T C A T C T C C A C C C A A C A C A A C A C G C C A
    T G G G A G T A G A G G T G G G T T G T G T T G T G C G G T
              880                 890                 900
```

```
     ***
   GTAGTTATTAAAAAAAAAA
   CATCAATAATTTTTTTTTT
            910        920
```

NUCLEOTIDE SEQUENCE OF THE RSV G GENE. THE cDNA SEQUENCE IS SHOWN IN THE PLUS (mRNA) STRAND SENSE IN THE 5' TO 3' DIRECTION. THE TRANSMEMBRANE (TM) ANCHOR DOMAIN IS UNDERLINED. AMINO ACIDS DIFFERING FROM THE PUBLISHED PRIMARY SEQUENCE OF THE PROTEIN ENCODED BY THE RSV G GENE ARE BOXED.

FIG.7D.

RESTRICTION MAP OF RSV G GENE

FIG.8.

Construction of a Bluescript-based expression vector containing the chimeric $F_{PIV-3}$-$F_{RSV}$ gene with the 5' untranslated region of the PIV-3 F gene intact but lacking the nucleotide sequences coding for the hydrophobic anchor domains and cytoplasmic tails of both the PIV-3 and RSV F genes.

Step 1: Preparation of the plasmid containing the modified PIV-3 F gene

[Plasmid map: pPI3F with P13 F insert, showing sites KpnI, EcoRV, EcoRI, BsrI at 3' end and BamHI, NotI, SacI at 5' end]

[Plasmid map: pMCR20 showing NaeI, SspI, T7 promoter, KpnI, ApaI, DraII, LacZ, MT promoter, f1 ori, Ap, ORI, SV40polyA, XbaI, NotI, EagI, BstXI, SacII, SacI, BglII, T3 promoter, AccI, ClaI, HindIII, EcoRV, EcoRI, PstI, SmaI, BamHI]

Cut with BamHI, blunt end and cut with BsrI

Retrieve 1.6 Kb EcoRV-BsrI PIV-3 F gene

Cut with EcoRV and BamH

Ligate: 1.6 Kb [BamHI]-BsrI F gene fragment + EcoRV-BamHI restricted vector +

```
         BspHI                    BamHI
5'   __ATCAATCAAAGGTCCTGTGATAATAG____ 3'
       CGTAGTTAGTTTCCAGGACACTATTATCCTAG
```

[Plasmid map: pMEI PI3 F2+FI showing NaeI, SspI, T7 promoter, KpnI, ApaI, DraII, LacZ, MT promoter, f1 ori, Ap, ORI, SV40polyA, BglII, T3 promoter, BsrI, PpuMI, BamHI, AccI, ClaI, HindIII, EcoRV]

FIG.9A.

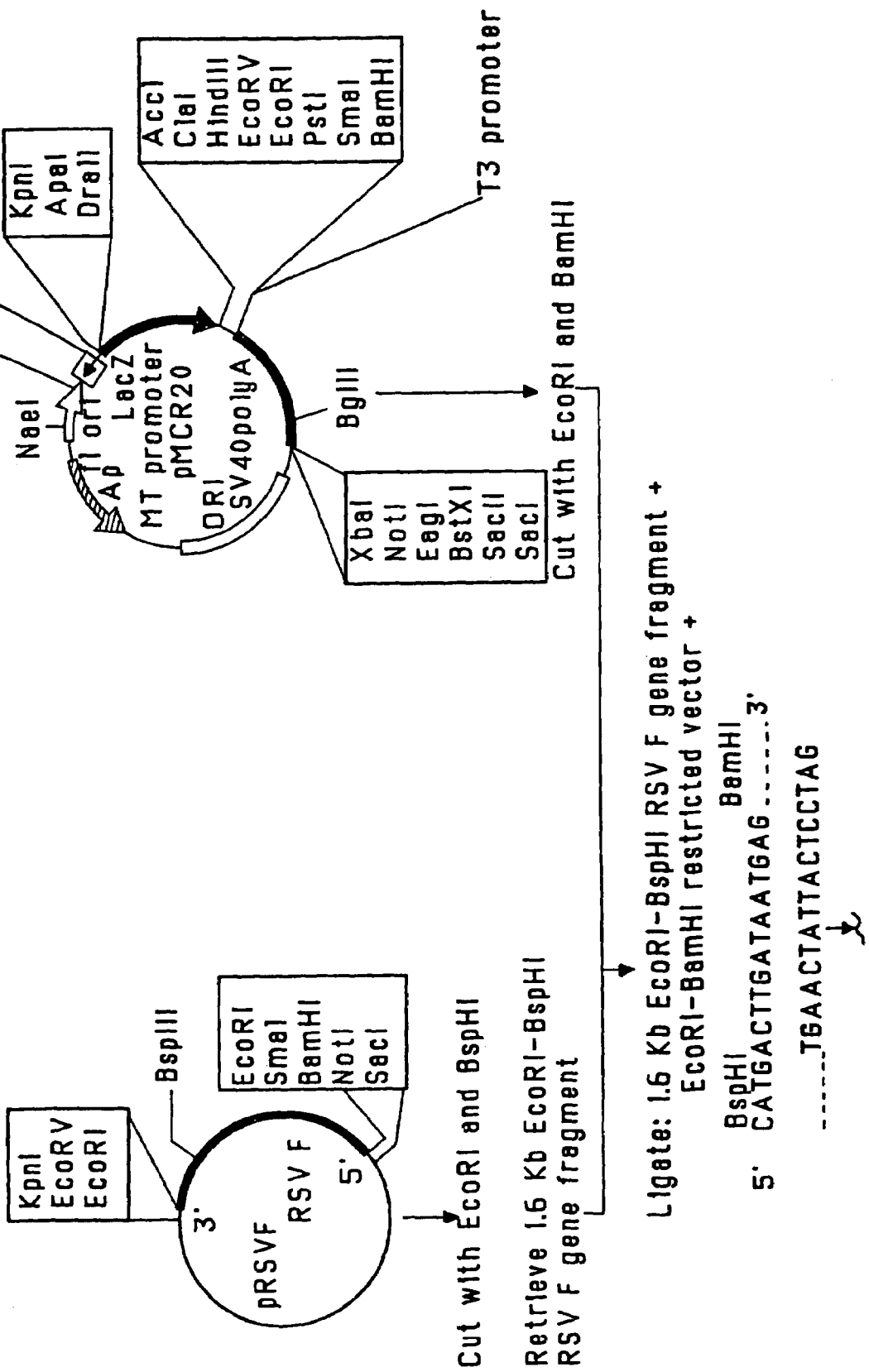
FIG.9B. Step 2: Preparation of the plasmid containing the modified RSV F gene FIG.10B.
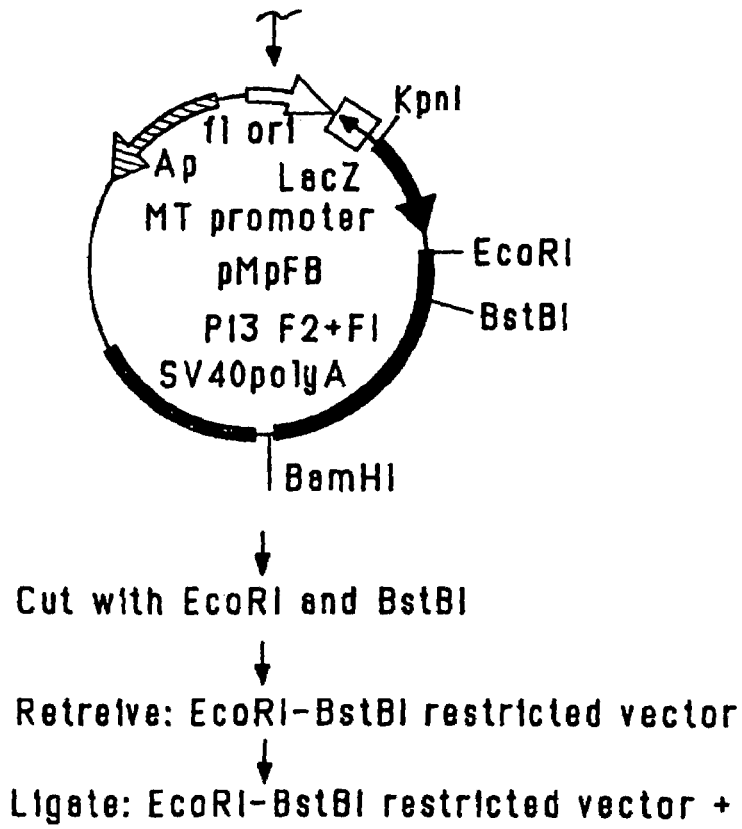
```
EcoRI                                              PpuMI
AATTCATGCCAACTTTAATACTGCTAATTATTACAACAATGATTATGG
CATCTTCCTGCCAAATAGATATCACAAAACTACAGCAATGTAGGTGTA
TTGGTCAACAGTCCCAAGGGATGAAGATATCACAAAACTT____ 3'
____GTACGGTTGAAATTATGACGATTAATAATGTTGTTACTAATACC
GTAGAAGGACGGTTTATCTATAGTGTTTTGATGTCGTACATCCACATA
ACCAGTTGTCAGGGTTTCCCTACTTCTATAGTGTTTTGAAGCTT
```
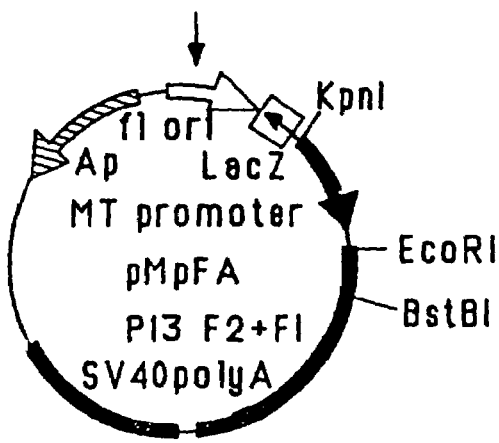

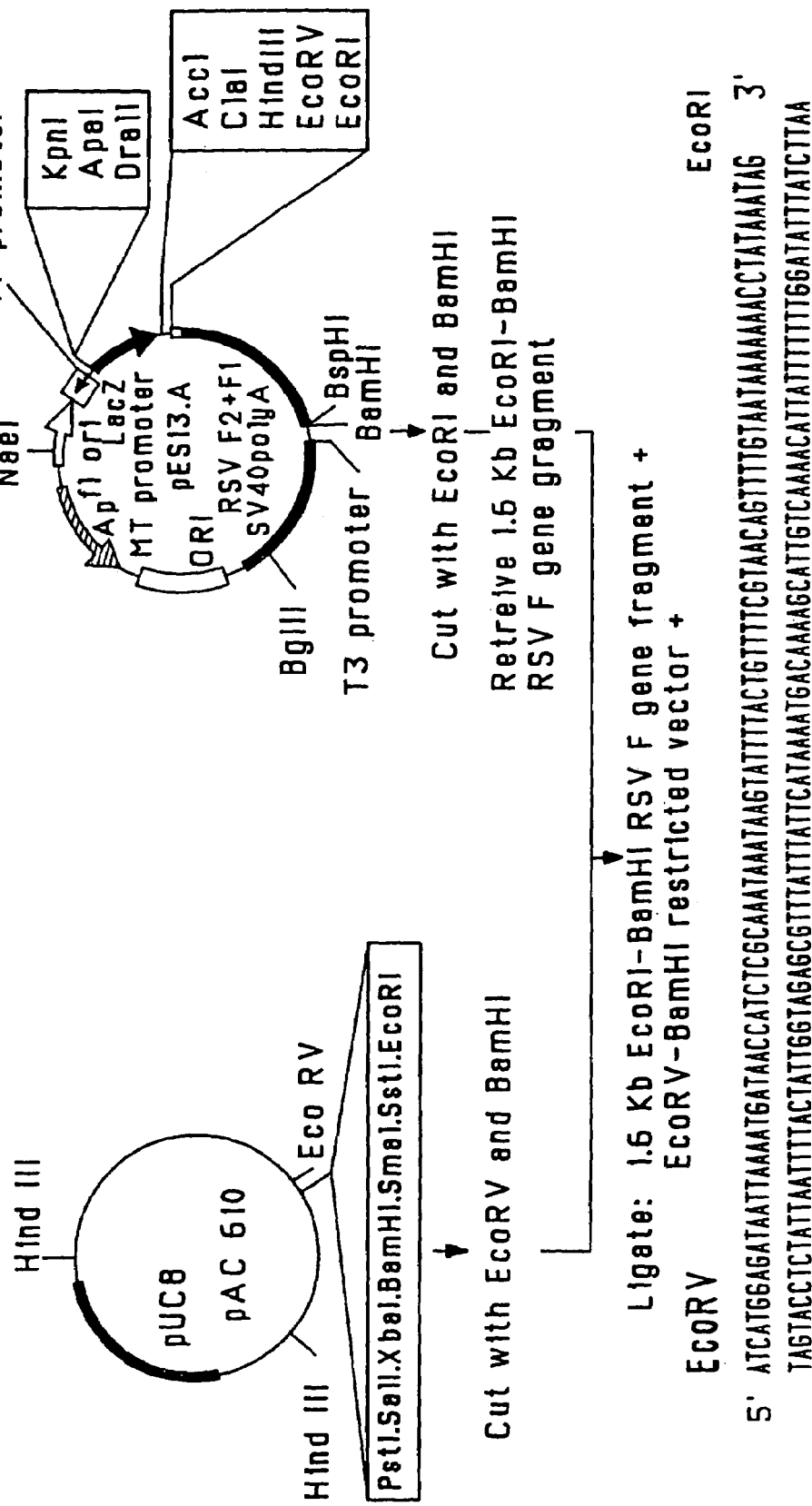
FIG.12A. Construction of the modified pAc 610 baculovirus expression vector containing the chimeric $F_{PIV-3}-F_{RSV}$ gene consisting of the PIV-3 F gene lacking both the 5' untranslated sequence as well as the transmembrane and cytoplasmic tail coding regions linked to the truncated RSV F1 gene

FIG. 13

IMMUNOBLOTS OF CELL LYSATES FROM Sf9 CELLS INFECTED WITH RECOMBINANT BACULOVIRUSES

Panel A — Lane 1: RSV F2+1; Lane 2: $F_{PIV-3}$-$F_{RSV}$; Lane 3: WILD TYPE

Panel B — Lane 1: RSV F2+1; Lane 2: $F_{PIV-3}$-$F_{RSV}$; Lane 3: WILD TYPE

FIG 13 : Immunoblots of cell lysates from Sf9 cells infected with recombinant baculoviruses containing the truncated RSV F gene (Lane 1), the chimeric $F_{PIV-3}$-$F_{RSV}$ gene (Lane 2) or infected with wild type virus (Lane 3) reacted with anti-F RSV Mab (panel A) and anti-F1 PIV-3 antiserum (panel B)

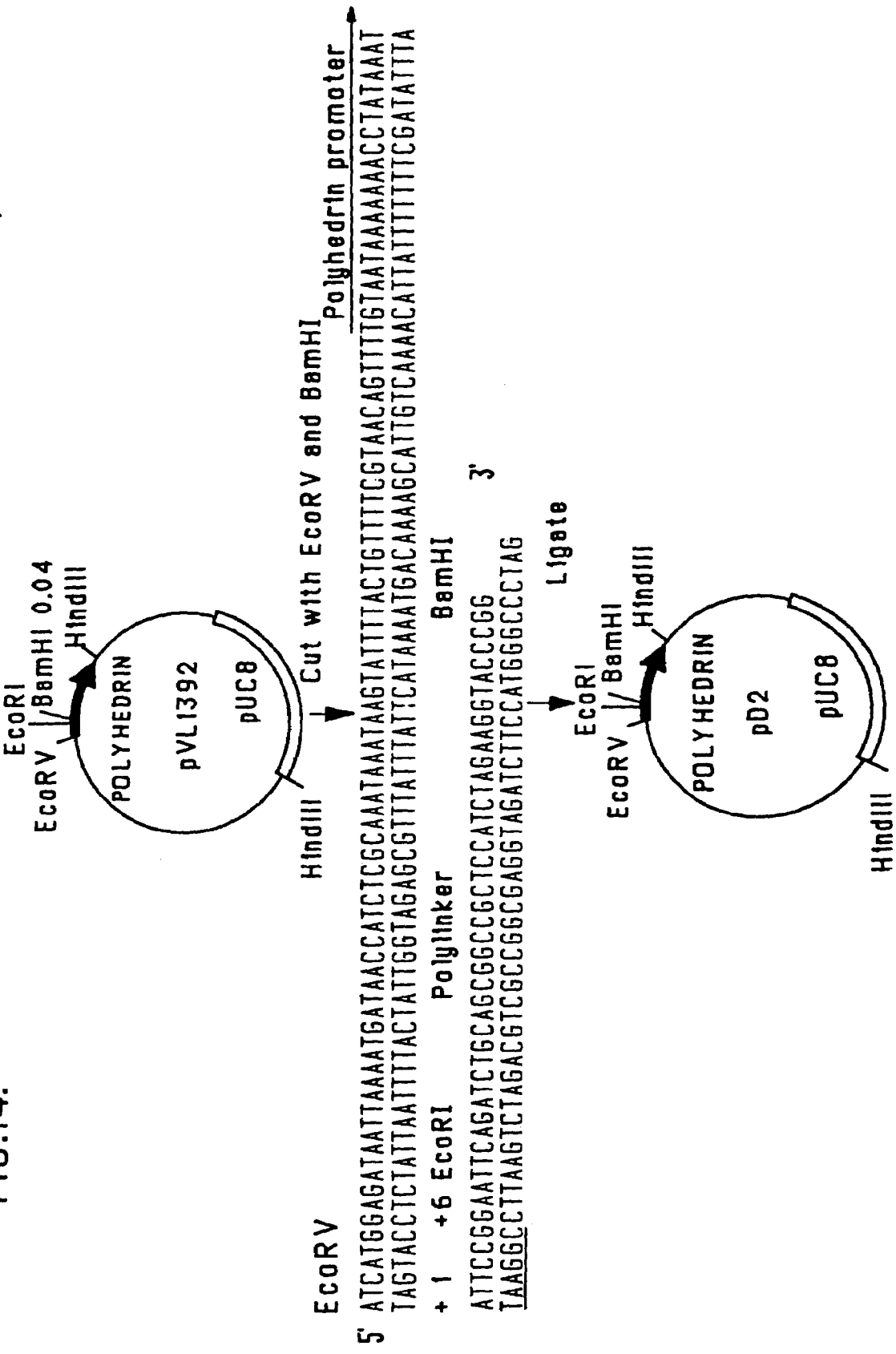
FIG. 14. CONSTRUCTION OF THE BACULOVIRUS TRANSFER VECTOR pD2

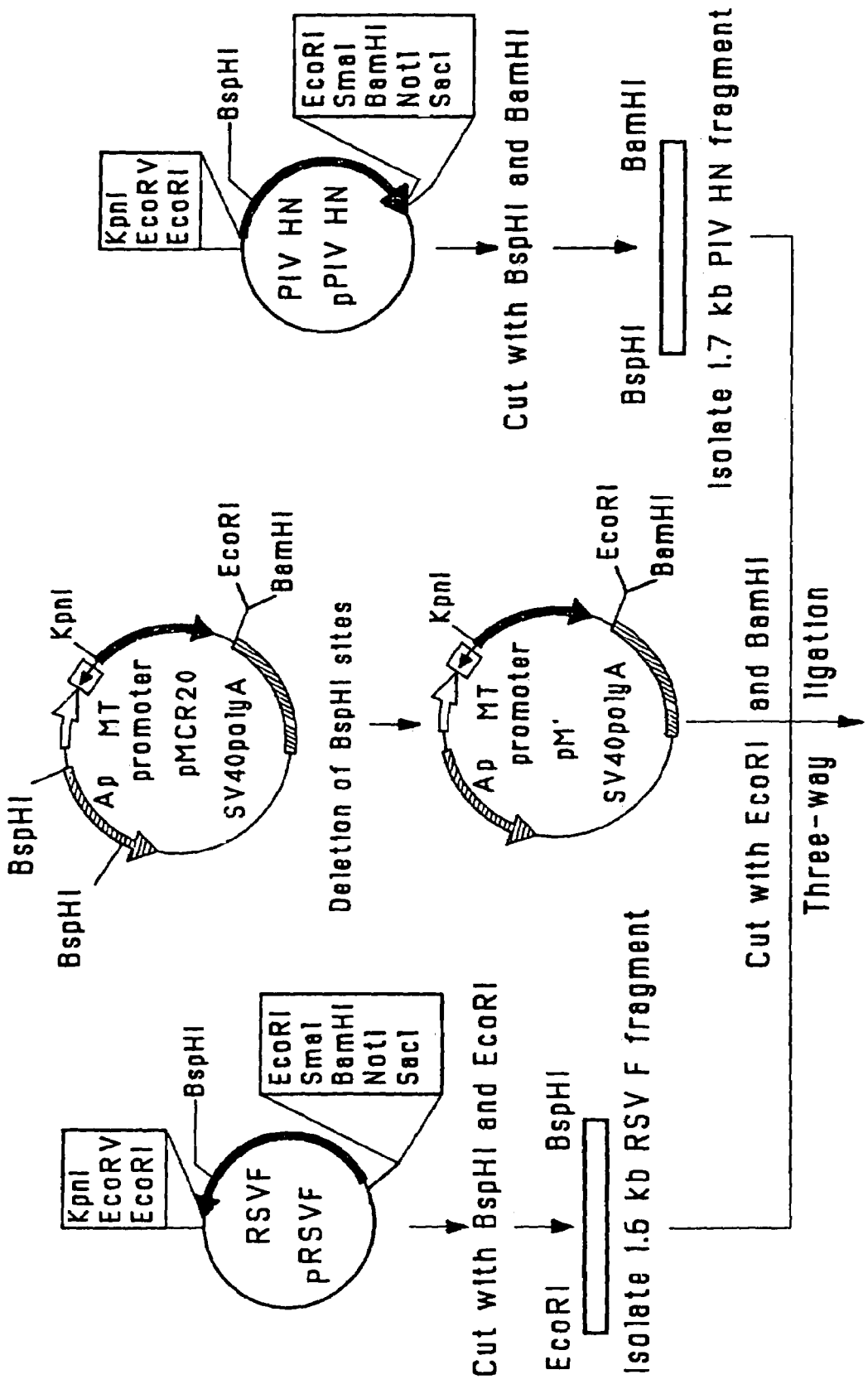
FIG.15A. CONSTRUCTION OF THE $F_{RSV}-HN_{PIV3}$ CHIMERIC GENE

FIG.16

SDS POLY ACRYLAMIDE GEL AND IMMUNOBLOTS OF PURIFIED $F_{RSV}-HN_{PIV-3}$ CHIMERIC PROTEIN

FIG 16 : A) Coomassie-stained SDS polyacrylamide gel of immunoaffinity- purified $F_{RSV}-HN_{PIV-3}$ protein.

B) Immunoblots of $F_{RSV}-HN_{PIV-3}$ protein reacted with an anti-F RSV Mab ( lane 1 ) and anti-HN PIV-3 antiserum ( lane 2)

FIG. 17. MUTAGENESIS OF THE PIV-3 F GENE

```
          5'    GLN    GLU    LYS    GLY    LIE    LYS   3'
PI3Fc  ......C A A  G A A  A A A  G G A  A T A  A A A......
          5'    ↓      ↓      ↓      ↓      ↓      ↓      3'
PI3Fm  ......C A G  G A G  A A G  G G T  A T C  A A G......
              847                                    864
```

5' TAACATAGGATCGTTACAGGAGAAGGGTATCAAGTTACA
ATTGTATCCTAGCAATGTCCTCTTCCCATAGTTCAATGT

AGGTATAGCATCATTATACCGCACAAATATCACAGAAAT
TCCATATCGTAGTAATATGGCGTGTTTATAGTGTCTTTA 5' -*2721

FIG. 18. CONSTRUCTION OF THE $F_{PIV3}$-$G_{RSV}$ CHIMERIC GENE

```
                        SEQUENCE LISTING (1) GENERAL INFORMATION:

(iii) NUMBER OF SEQUENCES: 38

(2) INFORMATION FOR SEQ ID NO: 1:

(i) SEQUENCE CHARACTERISTICS:
        (A) LENGTH: 1844 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 1:

AAGTCAATAC CAACAACTAT TAGCAGTCAT ACGTGCAAGA ACAAGAAAGA AGAGATTCAA      60

AAAGCTAAAT AAGAGAAATC AAAACAAAAG GTATAGAACA CCCGAACAAC AAAATCAAAA     120

CATCCAATCC ATTTTAAACA AAAATTCCAA AAGAGACCGG CAACACAACA AGCACCAAAC     180

ACAATGCCAA CTTTAATACT GCTAATTATT ACAACAATGA TTATGGCATC TTCCTGCCAA     240

ATAGATATCA CAAAACTACA GCATGTAGGT GTATTGGTCA ACAGTCCCAA AGGGATGAAG     300

ATATCACAAA ACTTCGAAAC AAGATATCTA ATTTTGAGCC TCATACCAAA AATAGAAGAC     360

TCTAACTCTT GTGGTGACCA ACAGATCAAA CAATACAAGA GGTTATTGGA TAGACTGATC     420

ATCCCTCTAT ATGATGGATT AAGATTACAG AAAGATGTGA TAGTAACCAA TCAAGAATCC     480

AATGAAAACA CTGATCCCAG AACAAGACGA TCCTTTGGAG GGGTAATTGG AACCATTGCT     540
```

-continued

```
CTGGGAGTAG CAACCTCAGC ACAAATTACA GCGGCAGTTG CTCTGGTTGA AGCCAAGCAG    600

GCAAAATCAG ACATCGAAAA ACTCAAAGAA GCAATCAGGG ACACAAACAA AGCAGTGCAG    660

TCAGTTCAGA GCTCTATAGG AAATTTAATA GTAGCAATTA ATCAGTCCA AGATTATGTC    720

AACAACGAAA TGGTGCCATC GATTGCTAGA CTAGGTTGTG AAGCAGCAGG ACTTCAATTA    780

GGAATTGCAT TAACACAGCA TTACTCAGAA TTAACAAACA TATTTGGTGA TAACATAGGA    840

TCGTTACAAG AAAAAGGAAT AAAATTACAA GGTATAGCAT CATTATACCG CACAAATATC    900

ACAGAAATAT TCACAACATC AACAGTTGAT AAATATGATA TCTATGATCT ATTATTTACA    960

GAATCAATAA AGGTGAGAGT TATAGATGTT GATTTGAATG ATTACTCAAT CACCCTCCAA   1020

GTCAGACTCC CTTTATTAAC TAGGCTGCTG AACACTCAGA TCTACAAAGT AGATTCCATA   1080

TCATATAATA TCCAAAACAG AGAATGGTAT ATCCCTCTTC CCAGCCATAT CATGACGAAA   1140

GGGGCATTTC TAGGTGGAGC AGATGTCAAG GAATGTATAG AAGCATTCAG CAGTTATATA   1200

TGCCCTTCTG ATCCAGGATT TGTACTAAAC CATGAAATGG AGAGCTGCTT ATCAGGAAAC   1260

ATATCCCAAT GTCCAAGAAC CACGGTCACA TCAGACATTG TTCCAAGATA TGCATTTGTC   1320

AATGGAGGAG TGGTTGCAAA CTGTATAACA ACCACCTGTA CATGCAACGG AATCGACAAT   1380

AGAATCAATC AACCACCTGA TCAAGGAGTA AAAATTATAA CACATAAAGA ATGTAATACA   1440

ATAGGTATCA ACGGAATGCT GTTCAATACA AATAAGAAG GAACTCTTGC ATTCTACACA   1500

CCAAATGATA TAACACTAAA TAATTCTGTT GCACTTGATC CAATTGACAT ATCAATCGAG   1560

CTTAACAAAG CCAATCAGA TCTAGAAGAA TCAAAGAAT GGATAAGAAG GTCAAATCAA   1620

AAACTAGATT CTATTGGAAA CTGGCATCAA TCTAGCACTA CAATCATAAT TATTTTAATA   1680

ATGATCATTA TATTGTTTAT AATTAATGTA ACGATAATTA CAATTGCAAT TAAGTATTAC   1740

AGAATTCAAA AGAGAAATCG AGTGGATCAA AATGACAAGC CATATGTACT AACAAACAAA   1800

TGACATATCT ATAGATCATT AGATATTAAA ATTATAAAAA ACTT                    1844
```

(2) INFORMATION FOR SEQ ID NO: 2:

(i) SEQUENCE CHARACTERISTICS:
        (A) LENGTH: 539 amino acids
        (B) TYPE: amino acid
        (C) STRANDEDNESS: single
        (D) TOPOLOGY: linear (xi) SEQUENCE DESCRIPTION: SEQ ID NO: 2:

```
Met Pro Thr Leu Ile Leu Leu Ile Ile Thr Thr Met Ile Met Ala Ser
1               5                   10                  15

Ser Cys Gln Ile Asp Ile Thr Lys Leu Gln His Val Gly Val Leu Val
                20                  25                  30

Asn Ser Pro Lys Gly Met Lys Ile Ser Gln Asn Phe Glu Thr Arg Tyr
            35                  40                  45

Leu Ile Leu Ser Leu Ile Pro Lys Ile Glu Asp Ser Asn Ser Cys Gly
        50                  55                  60

Asp Gln Gln Ile Lys Gln Tyr Lys Arg Leu Leu Asp Arg Leu Ile Ile
65                  70                  75                  80

Pro Leu Tyr Asp Gly Leu Arg Leu Gln Lys Asp Val Ile Val Thr Asn
                85                  90                  95

Gln Glu Ser Asn Glu Asn Thr Asp Pro Arg Thr Arg Arg Ser Phe Gly
            100                 105                 110

Gly Val Ile Gly Thr Ile Ala Leu Gly Val Ala Thr Ser Ala Gln Ile
        115                 120                 125
```

-continued

```
Thr Ala Ala Val Ala Leu Val Glu Ala Lys Gln Ala Lys Ser Asp Ile
    130                 135                 140

Glu Lys Leu Lys Glu Ala Ile Arg Asp Thr Asn Lys Ala Val Gln Ser
145                 150                 155                 160

Val Gln Ser Ser Ile Gly Asn Leu Ile Val Ala Ile Lys Ser Val Gln
                165                 170                 175

Asp Tyr Val Asn Asn Glu Ile Val Pro Ser Ile Ala Arg Leu Gly Cys
            180                 185                 190

Glu Ala Ala Gly Leu Gln Leu Gly Ile Ala Leu Thr Gln His Tyr Ser
        195                 200                 205

Glu Leu Thr Asn Ile Phe Gly Asp Asn Ile Gly Ser Leu Gln Glu Lys
    210                 215                 220

Gly Ile Lys Leu Gln Gly Ile Ala Ser Leu Tyr Arg Thr Asn Ile Thr
225                 230                 235                 240

Glu Ile Phe Thr Thr Ser Thr Val Asp Lys Tyr Asp Ile Tyr Asp Leu
                245                 250                 255

Leu Phe Thr Glu Ser Ile Lys Val Arg Val Ile Asp Val Asp Leu Asn
            260                 265                 270

Asp Tyr Ser Ile Thr Leu Gln Val Arg Leu Pro Leu Leu Thr Arg Leu
        275                 280                 285

Leu Asn Thr Gln Ile Tyr Lys Val Asp Ser Ile Ser Tyr Asn Ile Gln
    290                 295                 300

Asn Arg Glu Trp Tyr Ile Pro Leu Pro Ser His Ile Met Thr Lys Gly
305                 310                 315                 320

Ala Phe Leu Gly Gly Ala Asp Val Lys Glu Cys Ile Glu Ala Phe Ser
                325                 330                 335

Ser Tyr Ile Cys Pro Ser Asp Pro Gly Phe Val Leu Asn His Glu Met
            340                 345                 350

Glu Ser Cys Leu Ser Gly Asn Ile Ser Gln Cys Pro Arg Thr Thr Val
        355                 360                 365

Thr Ser Asp Ile Val Pro Arg Tyr Ala Phe Val Asn Gly Gly Val Val
    370                 375                 380

Ala Asn Cys Ile Thr Thr Thr Cys Thr Cys Asn Gly Ile Asp Asn Arg
385                 390                 395                 400

Ile Asn Gln Pro Pro Asp Gln Gly Val Lys Ile Ile Thr His Lys Glu
                405                 410                 415

Cys Asn Thr Ile Gly Ile Asn Gly Met Leu Phe Asn Thr Asn Lys Glu
            420                 425                 430

Gly Thr Leu Ala Phe Tyr Thr Pro Asn Asp Ile Thr Leu Asn Asn Ser
        435                 440                 445

Val Ala Leu Asp Pro Ile Asp Ile Ser Ile Glu Leu Asn Lys Ala Lys
    450                 455                 460

Ser Asp Leu Glu Glu Ser Lys Glu Trp Ile Arg Arg Ser Asn Gln Lys
465                 470                 475                 480

Leu Asp Ser Ile Gly Asn Trp His Gln Ser Ser Thr Thr Ile Ile Ile
                485                 490                 495

Ile Leu Ile Met Ile Ile Leu Phe Ile Ile Asn Val Thr Ile Ile
            500                 505                 510

Thr Ile Ala Ile Lys Tyr Tyr Arg Ile Gln Lys Arg Asn Arg Val Asp
        515                 520                 525

Gln Asn Asp Lys Pro Tyr Val Leu Thr Asn Lys
    530                 535
```

(2) INFORMATION FOR SEQ ID NO: 3:

(i) SEQUENCE CHARACTERISTICS:
        (A) LENGTH: 1833 base pairs
        (B) TYPE: nucleic acid
        (C) STRANDEDNESS: single
        (D) TOPOLOGY: linear (xi) SEQUENCE DESCRIPTION: SEQ ID NO: 3:

```
AGACAAATCC AAATTCGAGA TGGAATACTG GAAGCATACC AATCACGGAA AGGATGCTGG      60

CAATGAGCTG GAGACGTCCA TGGCTACTAA TGGCAACAAG CTCACCAATA AGATAACATA     120

TATATTATGG ACAATAATCC TGGTGTTATT ATCAATAGTC TTCATCATAG TGCTAATTAA     180

TTCCATCAAA AGTGAAAAGG CTCATGAATC ATTGCTGCAA GACATAAATA ATGAGTTTAT     240

GGAAATTACA GAAAAGATCC AAATGGCATC GGATAATACC AATGATCTAA TACAGTCAGG     300

AGTGAATACA AGGCTTCTTA CAATTCAGAG TCATGTCCAG AATTATATAC CAATATCACT     360

GACACAACAG ATGTCAGATC TTAGGAAATT CATTAGTGAA ATTACAATTA GAATGATAA     420

TCAAGAAGTG CTGCCACAAA GAATAACACA TGATGTGGGT ATAAAACCTT TAAATCCAGA     480

TGATTTTTGG AGATGCACGT CTGGTCTTCC ATCTTTAATG AAAACTCCAA AATAAGGTT     540

AATGCCAGGG CCGGGATTAT TAGCTATGCC AACGACTGTT GATGGCTGTA TCAGAACTCC     600

GTCCTTAGTT ATAAATGATC TGATTTATGC TTATACCTCA AATCTAATTA CTCGAGGTTG     660

TCAGGATATA GGAAAATCAT ATCAAGTCTT ACAGATAGGG ATAATAACTG TAAACTCAGA     720

CTTGGTACCT GACTTAAATC CCAGGATCTC TCATACTTTT AACATAAATG ACAATAGGAA     780

GTCATGTTCT CTAGCACTCC TAAATACAGA TGTATATCAA CTGTGTTCAA CTCCCAAAGT     840

TGATGAAAGA TCAGATTATG CATCATCAGG CATAGAAGAT ATTGTACTTG ATATTGTCAA     900

TTATGATGGC TCAATCTCAA CAACAAGATT TAAGAATAAT AACATAAGCT TGATCAACC     960

TTATGCTGCA CTATACCCAT CTGTTGGACC AGGGATATAC TACAAAGGCA AATAATATT    1020

TCTCGGGTAT GGAGGTCTTG AACATCCAAT AAATGAGAAT GTAATCTGCA ACACAACTGG    1080

GTGTCCCGGG AAAACACAGA GAGACTGCAA TCAGGCATCT CATAGTCCAT GGTTTTCAGA    1140

TAGGAGGATG GTCAACTCTA TCATTGTTGT TGACAAAGGC TTAAACTCAA TTCCAAAATT    1200

GAAGGTATGG ACGATATCTA TGAGACAGAA TTACTGGGGG TCAGAAGGAA GGTTACTTCT    1260

ACTAGGTAAC AAGATCTATA TATATACAAG ATCCACAAGT TGGCATAGCA AGTTACAATT    1320

AGGAATAATT GATATTACTG ATTACAGTGA TATAAGGATA AAATGGACAT GGCATAATGT    1380

GCTATCAAGA CCAGGAAACA ATGAATGTCC ATGGGGACAT TCATGTCCAG ATGGATGTAT    1440

AACAGGAGTA TATACTGATG CATATCCACT CAATCCCACA GGGAGCATTG TGTCATCTGT    1500

CATATTAGAT TCACAAAAAT CGAGAGTGAA CCCAGTCATA ACTTACTCAA CAGCAACCGA    1560

AAGAGTAAAC GAGCTGGCCA TCCGAAACAG AACACTCTCA GCTGGATATA CAACAACAAG    1620

CTGCATCACA CACTATAACA AAGGATATTG TTTTCATATA GTAGAAATAA ATCAGAAAAG    1680

CTTAAACACA CTTCAACCCA TGTTGTTCAA GACAGAGGTT CCAAAAAGCT GCAGTTAATC    1740

ATAATTAACC GCAATATGCA TTAACCTATC TATAATACAA GTATATGATA AGTAATCAGC    1800

AATCAGACAA TAGACAAAAG GGAAATATAA AAA                                1833
```

(2) INFORMATION FOR SEQ ID NO: 4:

(i) SEQUENCE CHARACTERISTICS:
        (A) LENGTH: 572 amino acids
        (B) TYPE: amino acid
        (C) STRANDEDNESS: single -continued (D) TOPOLOGY: linear (xi) SEQUENCE DESCRIPTION: SEQ ID NO: 4:

```
Met Glu Tyr Trp Lys His Thr Asn His Gly Lys Asp Ala Gly Asn Glu
1               5                   10                  15

Leu Glu Thr Ser Met Ala Thr Asn Gly Asn Lys Leu Thr Asn Lys Ile
            20                  25                  30

Thr Tyr Ile Leu Trp Thr Ile Ile Leu Val Leu Leu Ser Ile Val Phe
        35                  40                  45

Ile Ile Val Leu Ile Asn Ser Ile Lys Ser Glu Lys Ala His Glu Ser
50                  55                  60

Leu Leu Gln Asp Ile Asn Asn Glu Phe Met Glu Ile Thr Glu Lys Ile
65                  70                  75                  80

Gln Met Ala Ser Asp Asn Thr Asn Asp Leu Ile Gln Ser Gly Val Asn
                85                  90                  95

Thr Arg Leu Leu Thr Ile Gln Ser His Val Gln Asn Tyr Ile Pro Ile
            100                 105                 110

Ser Leu Thr Gln Gln Met Ser Asp Leu Arg Lys Phe Ile Ser Glu Ile
        115                 120                 125

Thr Ile Arg Asn Asp Asn Gln Glu Val Leu Pro Gln Arg Ile Thr His
130                 135                 140

Asp Val Gly Ile Lys Pro Leu Asn Pro Asp Asp Phe Trp Arg Cys Thr
145                 150                 155                 160

Ser Gly Leu Pro Ser Leu Met Lys Thr Pro Lys Ile Arg Leu Met Pro
                165                 170                 175

Gly Pro Gly Leu Leu Ala Met Pro Thr Thr Val Asp Gly Cys Ile Arg
            180                 185                 190

Thr Pro Ser Leu Val Ile Asn Asp Leu Ile Tyr Ala Tyr Thr Ser Asn
        195                 200                 205

Leu Ile Thr Arg Gly Cys Gln Asp Ile Gly Lys Ser Tyr Gln Val Leu
210                 215                 220

Gln Ile Gly Ile Ile Thr Val Asn Ser Asp Leu Val Pro Asp Leu Asn
225                 230                 235                 240

Pro Arg Ile Ser His Thr Phe Asn Ile Asn Asp Asn Arg Lys Ser Cys
                245                 250                 255

Ser Leu Ala Leu Leu Asn Thr Asp Val Tyr Gln Leu Cys Ser Thr Pro
            260                 265                 270

Lys Val Asp Glu Arg Ser Asp Tyr Ala Ser Ser Gly Ile Glu Asp Ile
        275                 280                 285

Val Leu Asp Ile Val Asn Tyr Asp Gly Ser Ile Ser Thr Thr Arg Phe
290                 295                 300

Lys Asn Asn Asn Ile Ser Phe Asp Gln Pro Tyr Ala Ala Leu Tyr Pro
305                 310                 315                 320

Ser Val Gly Pro Gly Ile Tyr Tyr Lys Gly Lys Ile Ile Phe Leu Gly
                325                 330                 335

Tyr Gly Gly Leu Glu His Pro Ile Asn Glu Asn Val Ile Cys Asn Thr
            340                 345                 350

Thr Gly Cys Pro Gly Lys Thr Gln Arg Asp Cys Asn Gln Ala Ser His
        355                 360                 365

Ser Pro Trp Phe Ser Asp Arg Arg Met Val Asn Ser Ile Ile Val Val
370                 375                 380

Asp Lys Gly Leu Asn Ser Ile Pro Lys Leu Lys Val Trp Thr Ile Ser
385                 390                 395                 400
```

```
Met Arg Gln Asn Tyr Trp Gly Ser Glu Gly Arg Leu Leu Leu Gly
            405                 410                 415

Asn Lys Ile Tyr Ile Tyr Thr Arg Ser Thr Ser Trp His Ser Lys Leu
            420                 425                 430

Gln Leu Gly Ile Ile Asp Ile Thr Asp Tyr Ser Asp Ile Arg Ile Lys
            435                 440                 445

Trp Thr Trp His Asn Val Leu Ser Arg Pro Gly Asn Asn Glu Cys Pro
450                 455                 460

Trp Gly His Ser Cys Pro Asp Gly Cys Ile Thr Gly Val Tyr Thr Asp
465                 470                 475                 480

Ala Tyr Pro Leu Asn Pro Thr Gly Ser Ile Val Ser Ser Val Ile Leu
                485                 490                 495

Asp Ser Gln Lys Ser Arg Val Asn Pro Val Ile Thr Tyr Ser Thr Ala
                500                 505                 510

Thr Glu Arg Val Asn Glu Leu Ala Ile Arg Asn Arg Thr Leu Ser Ala
                515                 520                 525

Gly Tyr Thr Thr Thr Ser Cys Ile Thr His Tyr Asn Lys Gly Tyr Cys
                530                 535                 540

Phe His Ile Val Glu Ile Asn Gln Lys Ser Leu Asn Thr Leu Gln Pro
545                 550                 555                 560

Met Leu Phe Lys Thr Glu Val Pro Lys Ser Cys Ser
                565                 570
```

(2) INFORMATION FOR SEQ ID NO: 5:

(i) SEQUENCE CHARACTERISTICS:
        (A) LENGTH: 1886 base pairs
        (B) TYPE: nucleic acid
        (C) STRANDEDNESS: single
        (D) TOPOLOGY: linear (xi) SEQUENCE DESCRIPTION: SEQ ID NO: 5:

```
ATGGAGTTGC CAATCCTCAA AGCAAATGCA ATTACCACAA TCCTCGCTGC AGTCACATTT      60

TGCTTTGCTT CTAGTCAAAA CATCACTGAA GAATTTTATC AATCAACATG CAGTGCAGTT     120

AGCAAAGGCT ATCTTAGTGC TCTAAGAACT GGTTGGTATA CTAGTGTTAT AACTATAGAA     180

TTAAGTAATA TCAAGGAAAA TAAGTGTAAT GGAACAGATG CTAAGGTAAA ATTGATGAAA     240

CAAGAATTAG ATAAATATAA AAATGCTGTA ACAGAATTGC AGTTGCTCAT GCAAAGCACA     300

CCAGCAGCAA ACAATCGAGC CAGAAGAGAA CTACCAAGGT TTATGAATTA TACACTCAAC     360

AATACCAAAA AACCAATGTA ACATTAAGC AAGAAAAGGA AAAGAAGATT TCTTGGTTTT      420

TTGTTAGGTG TTGGATCTGC AATCGCCAGT GGCATTGCTG TATCTAAGGT CCTGCACTTA     480

GAAGGAGAAG TGAACAAGAT CAAAAGTGCT CTACTATCCA CAAACAAGGC CGTAGTCAGC     540

TTATCAAATG GAGTTAGTGT CTTAACCAGC AAAGTGTTAG ACCTCAAAAA CTATATAGAT     600

AAACAATTGT TACCTATTGT GAATAAGCAA AGCTGCAGAA TATCAAATAT AGAAACTGTG     660

ATAGAGTTCC AACAAAAGAA CAACAGACTA CTAGAGATTA CCAGGGAATT TAGTGTTAAT     720

GCAGGTGTAA CTACACCTGT AAGCACTTAC ATGTTAACTA ATAGTGAATT ATTGTCATTA     780

ATCAATGATA TGCCTATAAC AAATGATCAG AAAAAGTTAA TGTCCAACAA TGTTCAAATA     840

GTTAGACAGC AAAGTTACTC TATCATGTCC ATAATAAAAG AGGAAGTCTT AGCATATGTA     900

GTACAATTAC CACTATATGG TGTGATAGAT ACACCTTGTT GGAAATTACA CACATCCCCT     960

CTATGTACAA CCAACACAAA AGAAGGGTCA AACATCTGTT TAACAAGAAC TGACAGAGGA    1020

TGGTACTGTG ACAATGCAGG ATCAGTATCT TTCTTCCCAC AAGCTGAAAC ATGTAAAGTT    1080
```

-continued

```
CAATCGAATC GAGTATTTTG TGACACAATG AACAGTTTAA CATTACCAAG TGAAGTAAAT    1140

CTCTGCAATG TTGACATATT CAATCCCAAA TATGATTGTA AAATTATGAC TTCAAAAACA    1200

GATGTAAGCA GCTCCGTTAT CACATCTCTA GGAGCCATTG TGTCATGCTA TGGCAAAACT    1260

AAATGTACAG CATCCAATAA AAATCGTGGA ATCATAAAGA CATTTTCTAA CGGGTGTGAT    1320

TATGTATCAA ATAAAGGGGT GGACACTGTG TCTGTAGGTA ACACATTATA TTATGTAAAT    1380

AAGCAAGAAG GCAAAAGTCT CTATGTAAAA GGTGAACCAA TAATAAATTT CTATGACCCA    1440

TTAGTATTCC CCTCTGATGA ATTTGATGCA TCAATATCTC AAGTCAATGA GAAGATTAAC    1500

CAGAGTTTAG CATTTATTCG TAAATCCGAT GAATTATTAC ATAATGTAAA TGCTGGTAAA    1560

TCAACCACAA ATATCATGAT AACTACTATA ATTATAGTGA TTATAGTAAT ATTGTTATCA    1620

TTAATTGCTG TTGGACTGCT CCTATACTGT AAGGCCAGAA GCACACCAGT CACACTAAGC    1680

AAGGATCAAC TGAGTGGTAT AAATAATATT GCATTTAGTA ACTGAATAAA ATAGCACCT    1740

AATCATGTTC TTACAATGGT TTACTATCTG CTCATAGACA ACCCATCTAT CATTGGATTT    1800

TCTTAAAATC TGAACTTCAT CGAAACTCTT ATCTATAAAC CATCTCACTT ACACTATTTA    1860

AGTAGATTCC TAGTTTATAG TTATAT                                         1886
```

(2) INFORMATION FOR SEQ ID NO: 6:

(i) SEQUENCE CHARACTERISTICS:
  (A) LENGTH: 594 amino acids
  (B) TYPE: amino acid
  (C) STRANDEDNESS: single
  (D) TOPOLOGY: linear (xi) SEQUENCE DESCRIPTION: SEQ ID NO: 6:

```
Met Glu Leu Pro Ile Leu Lys Ala Asn Ala Ile Thr Thr Ile Leu Ala
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Met Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205
```

-continued

```
Lys Gln Ser Cys Arg Ile Ser Asn Ile Glu Thr Val Ile Glu Phe Gln
    210                 215                 220
His Lys Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Asn Asn Val Gln Ile Val Arg Gln Gln Ser Tyr Ser Ile
        275                 280                 285
Met Ser Ile Ile Lys Glu Glu Val Leu Ala Tyr Val Val Gln Leu Pro
    290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
        355                 360                 365
Thr Met Asn Ser Leu Thr Leu Pro Ser Glu Val Asn Leu Cys Asn Val
    370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
Thr Val Ser Val Gly Asn Thr Leu Tyr Tyr Val Asn Lys Gln Glu Gly
    450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Leu Val Phe Pro Ser Asp Glu Phe Asp Ala Ser Ile
            500                 505                 510
Ser Gln Val Asn Glu Lys Ile Asn Gln Ser Leu Ala Phe Ile Arg Lys
        515                 520                 525
Ser Asp Glu Leu Leu His Asn Val Asn Ala Gly Lys Ser Thr Thr Asn
    530                 535                 540
Ile Met Ile Thr Thr Ile Ile Ile Glu Ile Ile Val Ile Leu Leu Ser
545                 550                 555                 560
Leu Ile Ala Val Gly Leu Leu Leu Tyr Cys Lys Ala Arg Ser Thr Pro
                565                 570                 575
Val Thr Leu Ser Lys Asp Gln Leu Ser Gly Ile Asn Asn Ile Ala Phe
            580                 585                 590
Ser Asn
```

(2) INFORMATION FOR SEQ ID NO: 7:

(i) SEQUENCE CHARACTERISTICS:
        (A) LENGTH: 920 base pairs (B) TYPE: nucleic acid
        (C) STRANDEDNESS: single
        (D) TOPOLOGY: linear (xi) SEQUENCE DESCRIPTION: SEQ ID NO: 7:

```
TGCAAACATG TCCAAAAACA AGGACCAACG CACCGCTAAG ACACTAGAAA AGACCTGGGA      60

CACTCTCAAT CATTTATTAT TCATATCATC GGGCTTATAT AAGTTAAATC TTAAATCTGT     120

AGCACAAATC ACATTATCCA TTCTGGCAAT GATAATCTCA ACTTCACTTA TAATTACAGC     180

CATCATATTC ATAGCCTCGG CAAACCACAA AGTCACACTA ACAACTGCAA TCATACAAGA     240

TGCAACAAGC CAGATCAAGA ACACAACCCC AACATACCTC ACTCAGGATC CTCAGCTTGG     300

AATCAGCTTC TCCAATCTGT CTGAAATTAC ATCACAAACC ACCACCATAC TAGCTTCAAC     360

AACACCAGGA GTCAAGTCAA ACCTGCAACC CACAACAGTC AAGACTAAAA ACACAACAAC     420

AACCCAAACA CAACCCAGCA AGCCCACTAC AAAACAACGC CAAACAAAC CACCAAACAA      480

ACCCAATAAT GATTTTCACT TCGAAGTGTT TAACTTTGTA CCCTGCAGCA TATGCAGCAA     540

CAATCCAACC TGCTGGGCTA TCTGCAAAAG AATACCAAAC AAAAAACCAG GAAAGAAAAC     600

CACCACCAAG CCTACAAAAA AACCAACCTT CAAGACAACC AAAAAAGATC TCAAACCTCA     660

AACCACTAAA CCAAAGGAAG TACCCACCAC CAAGCCCACA GAAGAGCCAA CCATCAACAC     720

CACCAAAACA AACATCACAA CTACACTGCT CACCAACAAC ACCACAGGAA ATCCAAAACT     780

CACAAGTCAA ATGGAAACCT TCCACTCAAC CTCCTCCGAA GGCAATCTAA GCCCTTCTCA     840

AGTCTCCACA ACATCCGAGC ACCCATCACA ACCCTCATCT CCACCCAACA CAACACGCCA     900

GTAGTTATTA AAAAAAAAA                                                  920
```

(2) INFORMATION FOR SEQ ID NO: 8:

(i) SEQUENCE CHARACTERISTICS:
        (A) LENGTH: 298 amino acids
        (B) TYPE: amino acid
        (C) STRANDEDNESS: single
        (D) TOPOLOGY: linear (xi) SEQUENCE DESCRIPTION: SEQ ID NO: 8:

```
Met Ser Lys Asn Lys Asp Gln Arg Thr Ala Lys Thr Leu Glu Lys Thr
1               5                   10                  15

Trp Asp Thr Leu Asn His Leu Leu Phe Ile Ser Ser Gly Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Thr Ala Ile Ile Phe Ile Ala Ser
    50                  55                  60

Ala Asn His Lys Val Thr Leu Thr Thr Ala Ile Ile Gln Asp Ala Thr
65                  70                  75                  80

Ser Gln Ile Lys Asn Thr Thr Pro Thr Tyr Leu Thr Gln Asp Pro Gln
                85                  90                  95

Leu Gly Ile Ser Phe Ser Asn Leu Ser Glu Ile Thr Ser Gln Thr Thr
            100                 105                 110

Thr Ile Leu Ala Ser Thr Thr Pro Gly Val Lys Ser Asn Leu Gln Pro
        115                 120                 125

Thr Thr Val Lys Thr Lys Asn Thr Thr Thr Gln Thr Gln Pro Ser
    130                 135                 140

Lys Pro Thr Thr Lys Gln Arg Gln Asn Lys Pro Pro Asn Lys Pro Asn
145                 150                 155                 160
```

```
Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Pro Thr Phe
        195                 200                 205

Lys Thr Thr Lys Lys Asp Leu Lys Pro Gln Thr Thr Lys Pro Lys Glu
    210                 215                 220

Val Pro Thr Thr Lys Pro Thr Glu Glu Pro Thr Ile Asn Thr Thr Lys
225                 230                 235                 240

Thr Asn Ile Thr Thr Thr Leu Leu Thr Asn Asn Thr Thr Gly Asn Pro
                245                 250                 255

Lys Leu Thr Ser Gln Met Glu Thr Phe His Ser Thr Ser Ser Glu Gly
                260                 265                 270

Asn Leu Ser Pro Ser Gln Val Ser Thr Thr Ser Glu His Pro Ser Gln
            275                 280                 285

Pro Ser Ser Pro Pro Asn Thr Thr Arg Gln
        290                 295

(2) INFORMATION FOR SEQ ID NO: 9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 9:

ATCAATCAAA GGTCCTGTGA TAATAG                                        26

(2) INFORMATION FOR SEQ ID NO: 10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 10:

CATGACTTGA TAATGAG                                                  17

(2) INFORMATION FOR SEQ ID NO: 11:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 11:

AATTCATGGA GTTGCTAATC CTCAAAGCAA ATGCAATTAC CACAATCCTC ACTGCAGTCA   60

CATTTTGTTT TGCTTCTGGT TCTAAG                                        86

(2) INFORMATION FOR SEQ ID NO: 12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 12:
```

```
ACTGGCATCA ATCTAGCACT ACATGAG                                           27

(2) INFORMATION FOR SEQ ID NO: 13:

(i) SEQUENCE CHARACTERISTICS:
        (A) LENGTH: 136 base pairs
        (B) TYPE: nucleic acid
        (C) STRANDEDNESS: single
        (D) TOPOLOGY: linear (xi) SEQUENCE DESCRIPTION: SEQ ID NO: 13:

AATTCATGCC AACTTTAATA CTGCTAATTA TTACAACAAT GATTATGGCA TCTTCCTGCC        60

AAATAGATAT CACAAAACTA CAGCATGTAG GTGTATTGGT CAACAGTCCC AAAGGGATGA      120

AGATATCACA AAACTT                                                      136

(2) INFORMATION FOR SEQ ID NO: 14:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (xi) SEQUENCE DESCRIPTION: SEQ ID NO: 14:

ATCATGGAGA TAATTAAAAT GATAACCATC TCGCAAATAA ATAAGTATTT TACTGTTTTC        60

GTAACAGTTT TGTAATAAAA AAACCTATAA ATAG                                   94

(2) INFORMATION FOR SEQ ID NO: 15:

(i) SEQUENCE CHARACTERISTICS:
        (A) LENGTH: 141 base pairs
        (B) TYPE: nucleic acid
        (C) STRANDEDNESS: single
        (D) TOPOLOGY: linear (xi) SEQUENCE DESCRIPTION: SEQ ID NO: 15:

ATCATGGAGA TAATTAAAAT GATAACCATC TCGCAAATAA ATAAGTATTT TACTGTTTTC        60

GTAACAGTTT TGTAATAAAA AAACCTATAA ATATTCCGGA ATTCAGATCT GCAGCGGCCG      120

CTCCATCTAG AAGGTACCCG G                                                141

(2) INFORMATION FOR SEQ ID NO: 16:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 16:

CATGACTAAT TCCATCAAAA GTGAAAAGGC T                                      31

(2) INFORMATION FOR SEQ ID NO: 17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 17:

CAAGAAAAAG GAATAAAA                                                     18

(2) INFORMATION FOR SEQ ID NO: 18:
```

```
    (i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO: 18:

ATTTCTGTGA TATTTGTGCG GTATAATGAT GCTATACCT                              39

(2) INFORMATION FOR SEQ ID NO: 19:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 19:

CAGGAGAAGG GTATCAAG                                                     18

(2) INFORMATION FOR SEQ ID NO: 20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 20:

AGGAGAAGGG TATCAAG                                                      17

(2) INFORMATION FOR SEQ ID NO: 21:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (xi) SEQUENCE DESCRIPTION: SEQ ID NO: 21:

ATCATGGAGA TAATTAAAAT GATAACCATC TCGCAAATAA ATAAGTATTT TACTGTTTTC        60

GTAACAGTTT TGTAATAAAA AAACCTATAA ATAG                                   94

(2) INFORMATION FOR SEQ ID NO: 22:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO: 22:

Gln Glu Lys Gly Ile Lys
  1               5

(2) INFORMATION FOR SEQ ID NO: 23:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO: 23:

Gln Glu Lys Gly Ile Lys
  1               5
```

(2) INFORMATION FOR SEQ ID NO: 24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 24:

```
ATCAATCTAG CACTACACAG                                              20
```

(2) INFORMATION FOR SEQ ID NO: 25:

(i) SEQUENCE CHARACTERISTICS:
        (A) LENGTH: 1617 base pairs
        (B) TYPE: nucleic acid
        (C) STRANDEDNESS: single
        (D) TOPOLOGY: linear (xi) SEQUENCE DESCRIPTION: SEQ ID NO: 25:

```
ATGCCAACTT TAATACTGCT AATTATTACA ACAATGATTA TGGCATCTTC CTGCCAAATA    60
GATATCACAA AACTCAGCA TGTAGGTGTA TTGGTCAACA GTCCCAAAGG GATGAAGATA   120
TCACAAAACT TCGAAACAAG ATATCTAATT TTGAGCCTCA TACCAAAAAT AGAAGACTCT   180
AACTCTTGTG GTGACCAACA GATCAAACAA TACAAGAGGT TATTGGATAG ACTGATCATC   240
CCTCTATATG ATGGATTAAG ATTACAGAAA GATGTGATAG TAACCAATCA AGAATCCAAT   300
GAAAACACTG ATCCCAGAAC AAGACGATCC TTTGGAGGGG TAATTGGAAC CATTGCTCTG   360
GGAGTAGCAA CCTCAGCACA AATTACAGCG GCAGTTGCTC TGGTTGAAGC CAAGCAGGCA   420
AAATCAGACA TCGAAAAACT CAAAGAAGCA ATCAGGGACA CAAACAAAGC AGTGCAGTCA   480
GTTCAGAGCT CTATAGGAAA TTTAATAGTA GCAATTAAAT CAGTCCAAGA TTATGTCAAC   540
AACGAAATGG TGCCATCGAT TGCTAGACTA GGTTGTGAAG CAGCAGGACT TCAATTAGGA   600
ATTGCATTAA CACAGCATTA CTCAGAATTA ACAAACATAT TTGGTGATAA CATAGGATCG   660
TTACAAGAAA AAGGAATAAA ATTACAAGGT ATAGCATCAT TATACCGCAC AAATATCACA   720
GAAATATTCA CAACATCAAC AGTTGATAAA TATGATATCT ATGATCTATT ATTTACAGAA   780
TCAATAAAGG TGAGAGTTAT AGATGTTGAT TTGAATGATT ACTCAATCAC CCTCCAAGTC   840
AGACTCCCTT TATTAACTAG GCTGCTGAAC ACTCAGATCT ACAAAGTAGA TTCCATATCA   900
TATAATATCC AAAACAGAGA ATGGTATATC CCTCTTCCCA GCCATATCAT GACGAAAGGG   960
GCATTTCTAG GTGGAGCAGA TGTCAAGGAA TGTATAGAAG CATTCAGCAG TTATATATGC  1020
CCTTCTGATC CAGGATTTGT ACTAAACCAT GAAATGGAGA GCTGCTTATC AGGAAACATA  1080
TCCCAATGTC CAAGAACCAC GGTCACATCA GACATTGTTC CAAGATATGC ATTTGTCAAT  1140
GGAGGAGTGG TTGCAAACTG TATAACAACC ACCTGTACAT GCAACGGAAT CGACAATAGA  1200
ATCAATCAAC CACCTGATCA AGGAGTAAAA ATTATAACAC ATAAAGAATG TAATACAATA  1260
GGTATCAACG GAATGCTGTT CAATACAAAT AAAGAAGGAA CTCTTGCATT CTACACACCA  1320
AATGATATAA CACTAAATAA TTCTGTTGCA CTTGATCCAA TTGACATATC AATCGAGCTT  1380
AACAAAGCCA ATCAGATCT AGAAGAATCA AAAGAATGGA TAAGAAGGTC AAATCAAAAA  1440
CTAGATTCTA TTGGAAACTG GCATCAATCT AGCACTACAA TCATAATTAT TTTAATAATG  1500
ATCATTATAT TGTTTATAAT TAATGTAACG ATAATTACAA TTGCAATTAA GTATTACAGA  1560
ATTCAAAAGA GAAATCGAGT GGATCAAAAT GACAAGCCAT ATGTACTAAC AAACAAA     1617
```

(2) INFORMATION FOR SEQ ID NO: 26:

(i) SEQUENCE CHARACTERISTICS:
    (A) LENGTH: 1715 base pairs
    (B) TYPE: nucleic acid
    (C) STRANDEDNESS: single
    (D) TOPOLOGY: linear (xi) SEQUENCE DESCRIPTION: SEQ ID NO: 26:

| | | | | | |
|---|---|---|---|---|---|
| ATGGAATACT | GGAAGCATAC | CAATCACGGA | AAGGATGCTG | GCAATGAGCT | GGAGACGTCC | 60 |
| ATGGCTACTA | ATGGCAACAA | GCTCACCAAT | AAGATAACAT | ATATATTATG | ACAATAATC | 120 |
| CTGGTGTTAT | TATCAATAGT | CTTCATCATA | GTGCTAATTA | ATTCCATCAA | AAGTGAAAAG | 180 |
| GCTCATGAAT | CATTGCTGCA | AGACATAAAT | AATGAGTTTA | TGGAAATTAC | AGAAAAGATC | 240 |
| CAAATGGCAT | CGGATAATAC | CAATGATCTA | ATACAGTCAG | GAGTGAATAC | AAGGCTTCTT | 300 |
| ACAATTCAGA | GTCATGTCCA | GAATTATATA | CCAATATCAC | TGACACAACA | GATGTCAGAT | 360 |
| CTTAGGAAAT | TCATTAGTGA | AATTACAATT | AGAAATGATA | ATCAAGAAGT | GCTGCCACAA | 420 |
| AGAATAACAC | ATGATGTGGG | TATAAAACCT | TTAAATCCAG | ATGATTTTTG | GAGATGCACG | 480 |
| TCTGGTCTTC | CATCTTTAAT | GAAAACTCCA | AAAATAAGGT | TAATGCCAGG | GCCGGGATTA | 540 |
| TTAGCTATGC | CAACGACTGT | TGATGGCTGT | ATCAGAACTC | CGTCCTTAGT | TATAAATGAT | 600 |
| CTGATTTATG | CTTATACCTC | AAATCTAATT | ACTCGAGGTT | GTCAGGATAT | AGGAAAATCA | 660 |
| TATCAAGTCT | TACAGATAGG | GATAATAACT | GTAAACTCAG | ACTTGGTACC | TGACTTAAAT | 720 |
| CCCAGGATCT | CTCATACTTT | TAACATAAAT | GACAATAGGA | AGTCATGTTC | TCTAGCACTC | 780 |
| CTAAATACAG | ATGTATATCA | ACTGTGTTCA | ACTCCCAAAG | TTGATGAAAG | ATCAGATTAT | 840 |
| GCATCATCAG | GCATAGAAGA | TATTGTACTT | GATATTGTCA | ATTATGATGG | CTCAATCTCA | 900 |
| ACAACAAGAT | TTAAGAATAA | TAACATAAGC | TTTGATCAAC | CTTATGCTGC | ACTATACCCA | 960 |
| TCTGTTGGAC | CAGGGATATA | CTACAAAGGC | AAAATAATAT | TTCTCGGGTA | TGGAGGTCTT | 1020 |
| GAACATCCAA | TAAATGAGAA | TGTAATCTGC | AACACAACTG | GGTGTCCCGG | AAAACACAG | 1080 |
| AGAGACTGCA | ATCAGGCATC | TCATAGTCCA | TGGTTTTCAG | ATAGGAGGAT | GGTCAACTCT | 1140 |
| ATCATTGTTG | TTGACAAAGG | CTTAAACTCA | ATTCCAAAAT | TGAAGGTATG | GACGATATCT | 1200 |
| ATGAGACAGA | ATTACTGGGG | GTCAGAAGGA | AGGTTACTTC | TACTAGGTAA | CAAGATCTAT | 1260 |
| ATATATACAA | GATCCACAAG | TTGGCATAGC | AAGTTACAAT | TAGGAATAAT | TGATATTACT | 1320 |
| GATTACAGTG | ATATAAGGAT | AAAATGGACA | TGGCATAATG | TGCTATCAAG | ACCAGGAAAC | 1380 |
| AATGAATGTC | CATGGGGACA | TTCATGTCCA | GATGGATGTA | TAACAGGAGT | ATATACTGAT | 1440 |
| GCATATCCAC | TCAATCCCAC | AGGGAGCATT | GTGTCATCTG | TCATATTAGA | TTCACAAAAA | 1500 |
| TCGAGAGTGA | ACCCAGTCAT | AACTTACTCA | ACAGCAACCG | AAAGAGTAAA | CGAGCTGGCC | 1560 |
| ATCCGAAACA | GAACACTCTC | AGCTGGATAT | ACAACAACAA | GCTGCATCAC | ACACTATAAC | 1620 |
| AAAGGATATT | GTTTTCATAT | AGTAGAAATA | AATCAGAAAA | GCTTAAACAC | ACTTCAACCC | 1680 |
| ATGTTGTTCA | AGACAGAGGT | TCCAAAAAGC | TGCAG | | | 1715 |

(2) INFORMATION FOR SEQ ID NO: 27:

(i) SEQUENCE CHARACTERISTICS:
        (A) LENGTH: 1722 base pairs
        (B) TYPE: nucleic acid
        (C) STRANDEDNESS: single
        (D) TOPOLOGY: linear (xi) SEQUENCE DESCRIPTION: SEQ ID NO: 27:

ATGGAGTTGC CAATCCTCAA AGCAAATGCA ATTACCACAA TCCTCGCTGC AGTCACATTT     60

```
TGCTTTGCTT CTAGTCAAAA CATCACTGAA GAATTTTATC AATCAACATG CAGTGCAGTT      120

AGCAAAGGCT ATCTTAGTGC TCTAAGAACT GGTTGGTATA CTAGTGTTAT AACTATAGAA      180

TTAAGTAATA TCAAGGAAAA TAAGTGTAAT GGAACAGATG CTAAGGTAAA ATTGATGAAA      240

CAAGAATTAG ATAAATATAA AAATGCTGTA ACAGAATTGC AGTTGCTCAT GCAAAGCACA      300

CCAGCAGCAA ACAATCGAGC CAGAAGAGAA CTACCAAGGT TTATGAATTA TACACTCAAC      360

AATACCAAAA AAACCAATGT AACATTAAGC AAGAAAAGGA AAAGAAGATT TCTTGGTTTT      420

TTGTTAGGTG TTGGATCTGC AATCGCCAGT GGCATTGCTG TATCTAAGGT CCTGCACTTA      480

GAAGGAGAAG TGAACAAGAT CAAAAGTGCT CTACTATCCA AAACAAGGC CGTAGTCAGC       540

TTATCAAATG GAGTTAGTGT CTTAACCAGC AAAGTGTTAG ACCTCAAAAA CTATATAGAT      600

AAACAATTGT TACCTATTGT GAATAAGCAA AGCTGCAGAA TATCAAATAT AGAAACTGTG      660

ATAGAGTTCC AACAAAGAA CAACAGACTA CTAGAGATTA CCAGGGAATT TAGTGTTAAT       720

GCAGGTGTAA CTACACCTGT AAGCACTTAC ATGTTAACTA ATAGTGAATT ATTGTCATTA      780

ATCAATGATA TGCCTATAAC AAATGATCAG AAAAAGTTAA TGTCCAACAA TGTTCAAATA      840

GTTAGACAGC AAAGTTACTC TATCATGTCC ATAATAAAAG AGGAAGTCTT AGCATATGTA      900

GTACAATTAC CACTATATGG TGTGATAGAT ACACCTTGTT GGAAATTACA CACATCCCCT      960

CTATGTACAA CCAACACAAA AGAAGGGTCA AACATCTGTT TAACAAGAAC TGACAGAGGA     1020

TGGTACTGTG ACAATGCAGG ATCAGTATCT TTCTTCCCAC AAGCTGAAAC ATGTAAAGTT     1080

CAATCGAATC GAGTATTTTG TGACACAATG AACAGTTTAA CATTACCAAG TGAAGTAAAT     1140

CTCTGCAATG TTGACATATT CAATCCCAAA TATGATTGTA AAATTATGAC TTCAAAAACA     1200

GATGTAAGCA GCTCCGTTAT CACATCTCTA GGAGCCATTG TGTCATGCTA TGGCAAAACT     1260

AAATGTACAG CATCCAATAA AAATCGTGGA ATCATAAAGA CATTTTCTAA CGGGTGTGAT     1320

TATGTATCAA ATAAAGGGGT GGACACTGTG TCTGTAGGTA ACACATTATA TTATGTAAAT     1380

AAGCAAGAAG GCAAAGTCT CTATGTAAAA GGTGAACCAA TAATAAATTT CTATGACCCA      1440

TTAGTATTCC CCTCTGATGA ATTTGATGCA TCAATATCTC AAGTCAATGA GAAGATTAAC     1500

CAGAGTTTAG CATTTATTCG TAAATCCGAT GAATTATTAC ATAATGTAAA TGCTGGTAAA     1560

TCAACCACAA ATATCATGAT AACTACTATA ATTATAGTGA TTATAGTAAT ATTGTTATCA     1620

TTAATTGCTG TTGGACTGCT CCTATACTGT AAGGCCAGAA GCACACCAGT CACACTAAGC     1680

AAGGATCAAC TGAGTGGTAT AAATAATATT GCATTTAGTA AC                        1722
```

(2) INFORMATION FOR SEQ ID NO: 28:

(i) SEQUENCE CHARACTERISTICS:
        (A) LENGTH: 894 base pairs
        (B) TYPE: nucleic acid
        (C) STRANDEDNESS: single
        (D) TOPOLOGY: linear (xi) SEQUENCE DESCRIPTION: SEQ ID NO: 28:

```
ATGTCCAAAA ACAAGGACCA ACGCACCGCT AAGACACTAG AAAAGACCTG GGACACTCTC       60

AATCATTTAT TATTCATATC ATCGGGCTTA TATAAGTTAA ATCTTAAATC TGTAGCACAA      120

ATCACATTAT CCATTCTGGC AATGATAATC TCAACTTCAC TTATAATTAC AGCCATCATA      180

TTCATAGCCT CGGCAAACCA CAAAGTCACA CTAACAACTG CAATCATACA AGATGCAACA      240

AGCCAGATCA GAACACAAC CCAACATAC CTCACTCAGG ATCCTCAGCT TGGAATCAGC        300

TTCTCCAATC TGTCTGAAAT TACATCACAA ACCACCACCA TACTAGCTTC AACAACACCA      360
```

```
GGAGTCAAGT CAAACCTGCA ACCCACAACA GTCAAGACTA AAAACACAAC AACAACCCAA      420

ACACAACCCA GCAAGCCCAC TACAAAACAA CGCCAAAACA AACCACCAAA CAAACCCAAT      480

AATGATTTTC ACTTCGAAGT GTTTAACTTT GTACCCTGCA GCATATGCAG CAACAATCCA      540

ACCTGCTGGG CTATCTGCAA AAGAATACCA AACAAAAAAC CAGGAAAGAA AACCACCACC      600

AAGCCTACAA AAAACCAAC CTTCAAGACA ACCAAAAAAG ATCTCAAACC TCAAACCACT       660

AAACCAAAGG AAGTACCCAC CACCAAGCCC ACAGAAGAGC CAACCATCAA CACCACCAAA      720

ACAAACATCA CAACTACACT GCTCACCAAC AACACCACAG GAAATCCAAA ACTCACAAGT      780

CAAATGGAAA CCTTCCACTC AACCTCCTCC GAAGGCAATC TAAGCCCTTC TCAAGTCTCC      840

ACAACATCCG AGCACCCATC ACAACCCTCA TCTCCACCCA ACACAACACG CCAG            894

(2) INFORMATION FOR SEQ ID NO: 29:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO: 29:

CGTAGTTAGT TTCCAGGACA CTATTATCCT AG                                     32

(2) INFORMATION FOR SEQ ID NO: 30:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 30:

TGAACTATTA CTCCTAG                                                      17

(2) INFORMATION FOR SEQ ID NO: 31:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO: 31:

GTACCTCAAC GATTAGGAGT TTCGTTTACG TTAATGGTGT TAGGAGTGAC GTCAGTGTAA       60

AACAAAACGA AGACCAAGAT TCCAG                                             85

(2) INFORMATION FOR SEQ ID NO: 32:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 32:

CGTAGTTAGA TCGTGATGTA CTCCTAG                                           27

(2) INFORMATION FOR SEQ ID NO: 33:

(i) SEQUENCE CHARACTERISTICS:
        (A) LENGTH: 136 base pairs
        (B) TYPE: nucleic acid
```

(C) STRANDEDNESS: single
(D) TOPOLOGY: linear (xi) SEQUENCE DESCRIPTION: SEQ ID NO: 33:

GTACGGTTGA AATTATGACG ATTAATAATG TTGTTACTAA TACCGTAGAA GGACGGTTTA      60

TCTATAGTGT TTTGATGTCG TACATCCACA TAACCAGTTG TCAGGGTTTC CCTACTTCTA     120

TAGTGTTTTG AAGCTT                                                    136

(2) INFORMATION FOR SEQ ID NO: 34:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (xi) SEQUENCE DESCRIPTION: SEQ ID NO: 34:

TAGTACCTCT ATTAATTTTA CTATTGGTAG AGCGTTTATT TATTCATAAA ATGACAAAAG      60

CATTGTCAAA ACATTATTTT TTTGGATATT TATCTTAA                             98

(2) INFORMATION FOR SEQ ID NO: 35:

(i) SEQUENCE CHARACTERISTICS:
        (A) LENGTH: 145 base pairs
        (B) TYPE: nucleic acid
        (C) STRANDEDNESS: single
        (D) TOPOLOGY: linear (xi) SEQUENCE DESCRIPTION: SEQ ID NO: 35:

TAGTACCTCT ATTAATTTTA CTATTGGTAG AGCGTTTATT TATTCATAAA ATGACAAAAG      60

CATTGTCAAA ACATTATTTT TTTGGATATT TATAAGGCCT TAAGTCTAGA CGTCGCCGGC    120

GAGGTAGATC TTCCATGGGC CCTAG                                          145

(2) INFORMATION FOR SEQ ID NO: 36:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 36:

TGATTAAGGT AGTTTTCACT TTTCCGAGTA C                                    31

(2) INFORMATION FOR SEQ ID NO: 37:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO: 37:

TAAAGACACT ATAAACACGC CATATTACTA CGATATGGA                            39

(2) INFORMATION FOR SEQ ID NO: 38:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 38:

AGGACAAAAG                                                                                                          10

1

CHIMERIC IMMUNOGENS

REFERENCE TO RELATED APPLICATIONS

This application is a division of U.S. application Ser. No. 10/842,032 filed May 10, 2004 (now U.S. Pat. No. 7,244,589), which is a continuation of U.S. application Ser. No. 09/479,240 filed Jan. 7. 2000 (now abandoned) which itself is a continuation of U.S. application Ser. No. 08/467,961 filed Jun. 6, 1995 (now U.S. Pat. No.6,171,783) which itself is a division of U.S. application Ser. No. 08/001,554 filed Jan. 6, 1993 (now U.S. Pat. No. 6,225,091), which claims priority under 35 USC 119(e) from Great Britain Application No. 92 00117.1 filed Jan. 6. 1992.

FIELD OF INVENTION

The present invention relates to the engineering and expression of multimeric hybrid genes containing sequences from the gene coding for immunogenic proteins or protein fragments of numerous pathogens.

BACKGROUND TO THE INVENTION

The advantage of the approach taken by the present invention is to produce single immunogens containing protective antigens from a range of pathogens. Such chimeras greatly simplify the development of combination vaccines, in particular, with the view ultimately to produce single dose multivalent vaccines. Multivalent vaccines are currently made by separately producing pathogens and/or their pertinent antigens and combining them in various formulations. This is a labour intensive, costly and complex manufacturing procedure. In contrast, the availability of a single immunogen capable of protecting against a range of diseases would solve many of the problems of multivalent vaccine production. Several chimeric immunogens of the type provided herein may be combined to decrease the number of individual antigens required in a multivalent vaccine.

Human Parainfluenza virus types 1, 2, 3 and Respiratory syncytial virus types A and B are the major viral pathogens responsible for causing severe respiratory tract infections in infants and young children. It is estimated that, in the United States alone, approximately 1.6 million infants under one year of age will have a clinically significant RSV infection each year and an additional 1.4 million infants will be infected with PIV-3. Approximately 4000 infants less than one year of age in the United States die each year from complications arising from severe respiratory tract disease caused by infection with RSV and PIV-3. The WHO and NIALD vaccine advisory committees ranked RSV number two behind HIV for vaccine development while the preparation of an efficacious PIV-3 vaccine is ranked in the top ten vaccines considered a priority for vaccine development.

Safe and effective vaccines for protecting infants against these viral infections are not available and are urgently required. Clinical trials have shown that formaldehyde-inactivated and live-attenuated viral vaccines failed to adequately protect vaccines against these infections. In fact, infants who received the formalin-inactivated RSV vaccine developed more serious lower respiratory tract disease during subsequent natural RSV infection than did the control group. [Am. J. Epidemiology 89, 1969, p. 405-421; J. Inf. Dis. 145, 1982, p. 311-319]. Furthermore, RSV glycoproteins purified by immunoaffinity chromatography using elution at acid pH induced immunopotentiation in cotton rats. [Vaccine, 10(7), 1992, p. 475-484]. The development of efficacious PIV-3 and RSV vaccines which do not cause exacerbated pulmonary disease in vaccines following injection with wild-type virus would have significant therapeutic implications. It is anticipated that the development of a single recombinant immunogen capable of simultaneously protecting infants against diseases caused by infection with both Parainfluenza and Respiratory syncytial viruses could significantly reduce the morbidity and mortality caused by these viral infections.

It has been reported that a protective response against PIV-3 and RSV is contingent on the induction of neutralizing antibodies against the major viral surface glycoproteins. For PIV, these protective immunogens are the HN protein which has a molecular weight of 72 kDa and possesses both hemagglutination and neuraminidase activities and the fusion (F) protein, which has a molecular weight of 65 kDa and which is responsible for both fusion of the virus to the host cell membrane and cell-to-cell spread of the virus. For RSV, the two major immunogenic proteins are the 80 to 90 kDa G glycoprotein and the 70 kDa fusion (F) protein. The G and F proteins are thought to be functionally analogous to the PIV HN and F proteins, respectively. The PIV and RSV F glycoproteins are synthesized as inactive precursors (FO) which are proteolytically cleaved into N-terminal F2 and C-terminal F1 fragments which remain linked by disulphide bonds.

Recombinant surface glycoproteins from PIV and RSV have been individually expressed in insect cells using the baculovirus system [Ray et al., (1989), Virus Research, 12: 169-180; Coelingh et al., (1987), Virology, 160: 465-472; Wathen et al., (1989), J. of Inf. Dis. 159: 253-263] as well as in mammalian cells infected with recombinant poxviruses [Spriggs, et al., (1987), J. Virol. 61: 3416-3423; Stott et al., (1987), J. Virol. 61: 3855-3861]. Recombinant antigens produced in these systems were found to protect immunized cotton rats against live virus challenge. More recently, hybrid RSV F-G [Wathan et al., (1989), J. Gen Virol. 70: 2625-2635; Wathen, published International Patent application WO 89/05823] and PIV-3 F-HN [Wathen, published International Patent Application WO 89/10405], recombinant antigens have been engineered and produced in mammalian and insect cells. The RSV F-G hybrid antigen was shown to be protective in cotton rats [Wathan et al., (1989), J. Gen. Virol. 70: 2637-2644] although it elicited a poor anti-G antibody response [Connors et al., (1992), Vaccine 10: 475-484]. The protective ability of the PIV-3 F-HN protein was not reported in the published patent application. These antigens were engineered with the aim to protect against only the homologous virus, that is either RSV or PIV-3. However, it would be advantageous and economical to engineer and produce a single recombinant immunogen containing at least one protective antigen from each virus in order simultaneously to protect infants and young children against both PIV and RSV infections. The chimeric proteins provided herein for such purpose also may be administered to pregnant women or women of child bearing age to stimulate maternal antibodies to both PIV and RSV. In addition, the vaccine also may be administered to other susceptible individuals, such as the elderly.

SUMMARY OF INVENTION

In its broadest aspect, the present invention provides a multimeric hybrid gene, comprising a gene sequence coding for an immunogenic region of a protein from a first pathogen linked to a gene sequence coding for an immunogenic region of a protein from a second pathogen and to a chimeric protein encoded by such multimeric hybrid gene. Such chimeric protein comprises an immunogenic region of a protein from a first pathogen linked to an immunogenic region of a protein from a second pathogen.

The first and second pathogens are selected from bacterial and viral pathogens and, in one embodiment, may both be viral pathogens. Preferably, the first and second pathogens are selected from those causing different respiratory tract diseases, which may be upper and lower respiratory tract diseases. In a preferred embodiment, the first pathogen is parainfluenza virus and the second pathogen is respiratory syncytial virus. The PIV protein particularly is selected from PIV-3 F and HN proteins and the RSV protein particularly is selected from RSV G and F proteins. Another aspect of the invention provides cells containing the multimeric hybrid gene for expression of a chimeric protein encoded by the gene. Such cells may be bacterial cells, mammalian cells, insect cells, yeast cells or fungal cells. Further, the present invention provides a live vector for antigen delivery containing the multimeric hybrid gene, which may be a viral vector or a bacterial vector, and a physiologically-acceptable carrier therefor. Such live vector may form the active component of a vaccine against diseases caused by multiple pathogenic infections. Such vaccine may be formulated to be administered in an injectable form, intranasally or orally.

In an additional aspect of the present invention, there is provided a process for the preparation of a chimeric protein, which comprises isolating a gene sequence coding for an immunogenic region of a protein from a first pathogen; isolating a gene sequence coding for an immunogenic region of a protein from a second pathogen; linking the gene sequences to form a multimeric hybrid gene; and expressing the multimeric hybrid gene in a cellular expression system. The first and second pathogens are selected from bacterial and viral pathogens. Such cellular expression system may be provided by bacterial cells, mammalian cells, insect cells, yeast cells or fungal cells. The chimeric protein product of gene expression may be separated from a culture of the cellular expression system and purified.

The present invention further includes a vaccine against diseases caused by multiple pathogen infections, comprising the chimeric protein encoded by the multimeric hybrid gene and a physiologically-acceptable carrier therefor. Such vaccine may be formulated to be administered in an injectable form, intranasally or orally.

The vaccines provided herein may be used to immunize a host against disease caused by multiple pathogenic infections, particularly those caused by a parainfluenza virus and respiratory syncytial virus, by administering an effective amount of the vaccine to the host. As noted above, for human PIV and RSV, the host may be infants and young children, pregnant women as well as those of a child-bearing age, and other susceptible persons, such as the elderly.

The chimeric protein provided herein also may be used as a diagnostic reagent for detecting infection by a plurality of different pathogens in a host, using a suitable assaying procedure.

It will be appreciated that, while the description of the present invention which follows focuses mainly on a chimeric molecule which is effective for immunization against diseases caused by infection by PIV and RSV, nevertheless the invention provided herein broadly extends to any chimeric protein which is effected for immunization against diseases caused by a plurality of pathogens, comprising an antigen from each of the pathogens linked in a single molecule, as well as to genes coding for such chimeric molecules.

In this application, by the term "multimeric hybrid genes" we mean genes encoding antigenic regions of proteins from different pathogens and by the term "chimeric proteins" we mean immunogens containing antigenic regions from proteins from different pathogens.

BRIEF DESCRIPTION OF DRAWINGS

FIGS. 1A to 1E show the nucleotide (SEQ ID No: 1) and amino acid (SEQ ID No: 2) sequence of a PCR-amplified PIV-3 F gene and F protein, respectively;

FIG. 2 shows the restriction map of the PIV-3 F gene;

FIGS. 3A to 3E show the nucleotide (SEQ ID No: 3) and amino acid (SEQ ID No: 4) sequences of the PIV-3 HN gene and HN protein, respectively;

Figure 5B:
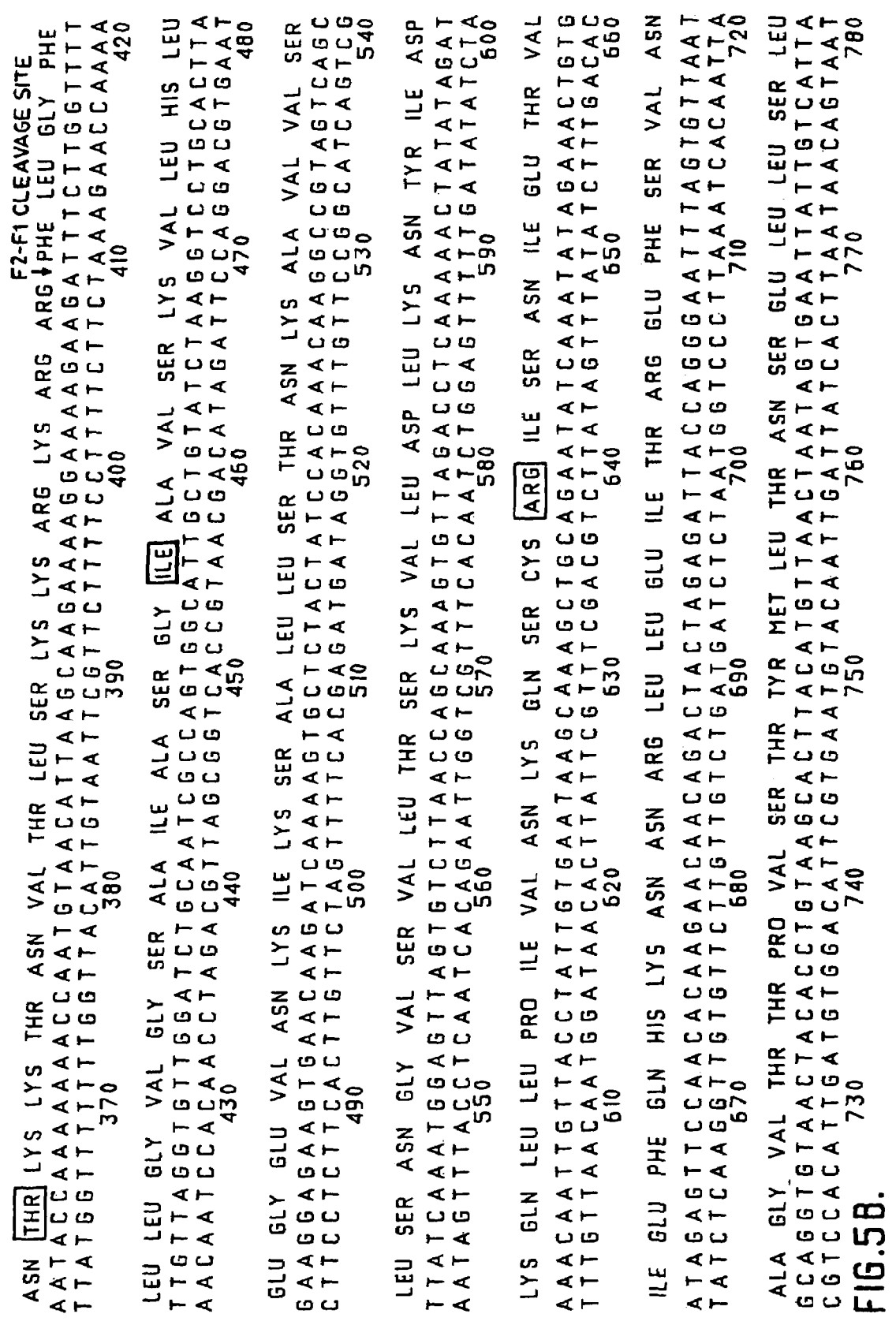
Figure 5C:
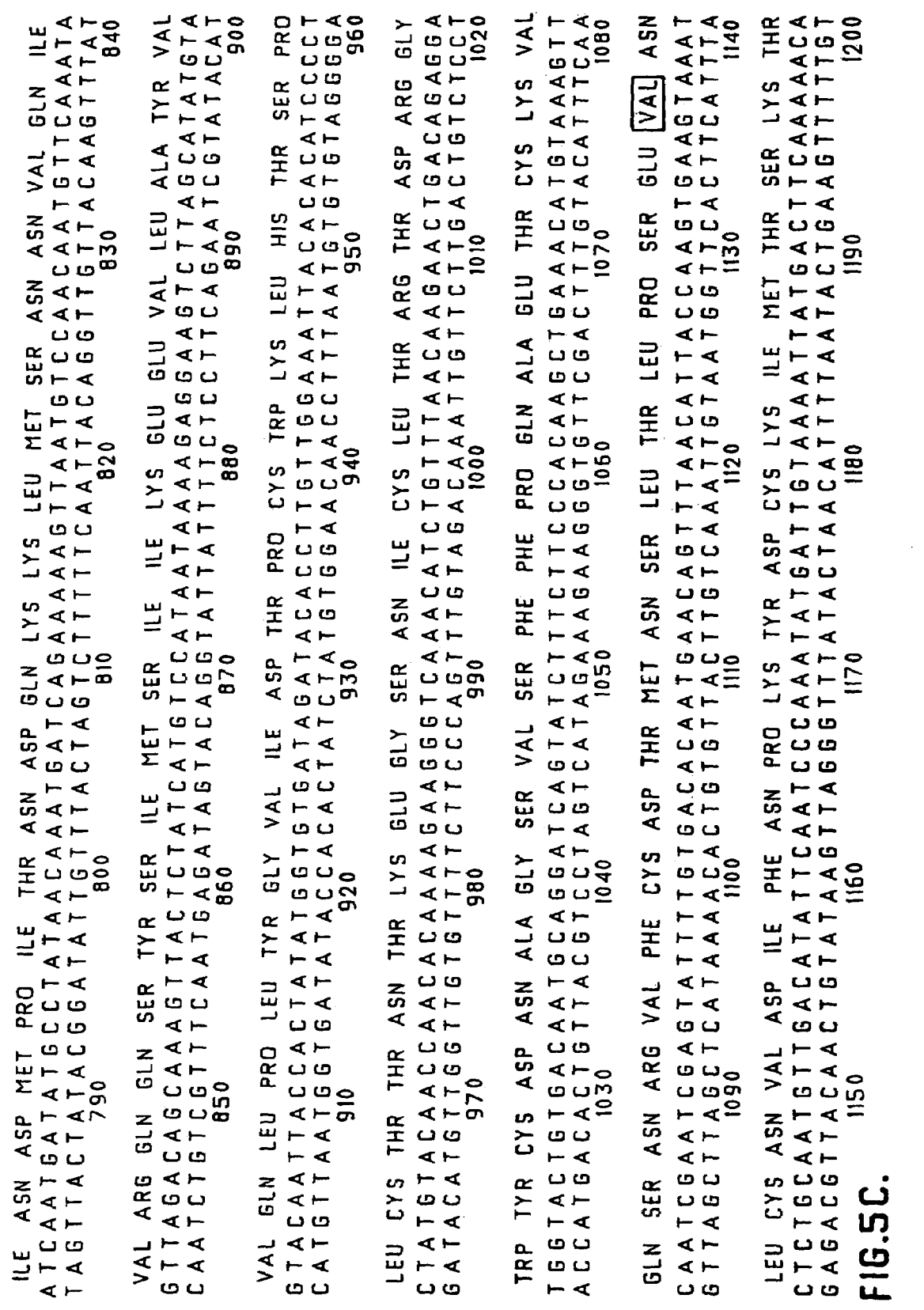
Figure 5D:
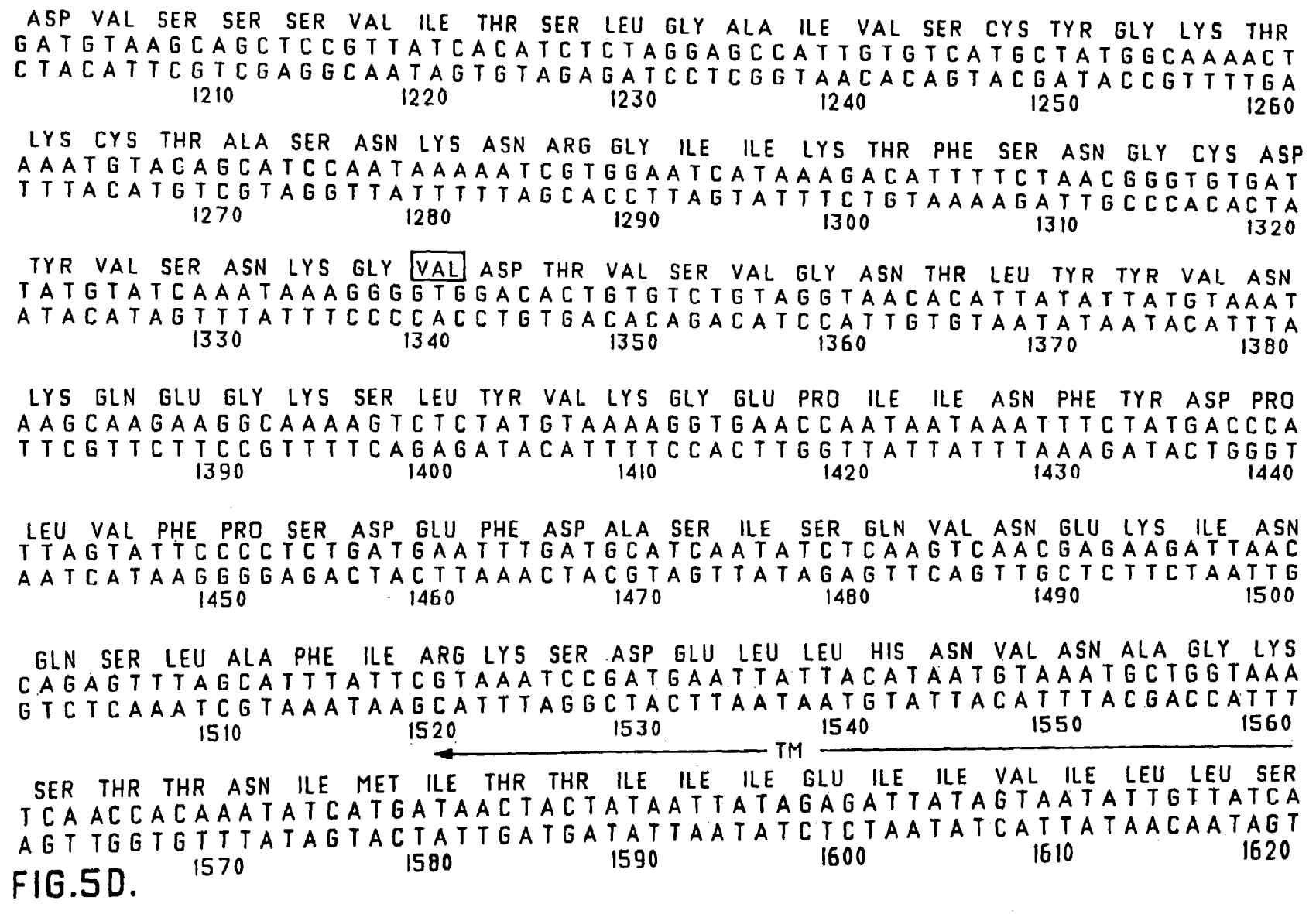

FIGS. 5A to 5E show the nucleotide (SEQ ID No: 5) and amino acid (SEQ ID No: 6) sequences of the RSV F gene and RSV F protein, respectively;

FIGS. 7A to 7D show the nucleotide (SEQ ID No: 7) and amino acid (SEQ ID No: 8) sequences of the RSV G gene and RSV G protein, respectively;

Figure 8:
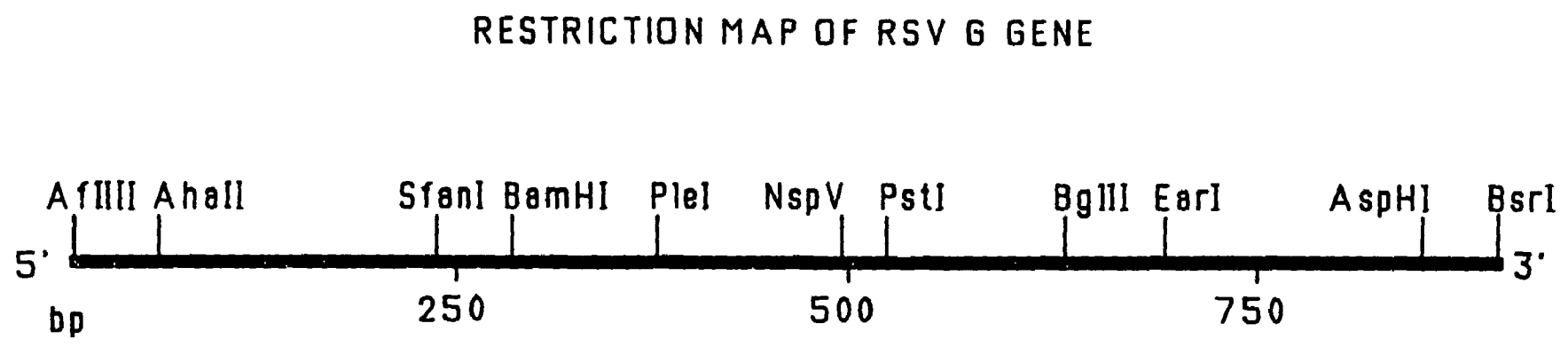

FIG. 8 shows the restriction map of the RSV G gene;

FIGS. 9A to 9D show the steps involved in the construction of an expression vector containing a chimeric $F_{PIV-3}$-$F_{RSV}$ gene;

FIGS. 10A to 10B show the steps involved in the construction of an expression vector containing a $F_{PIV-3}$ gene lacking the 5'-untranslated sequence and transmembrane anchor and cytoplasmic tail coding regions;

FIGS. 12A to 12B show the steps involved in construction of a modified pAC 610 baculovirus expression vector containing a chimeric $F_{PIV-3}$-$F_{RSV}$ gene consisting of the PIV-3 F gene lacking both the 5'-untranslated sequence as well as transmembrane and cytoplasmic tail coding region linked to the truncated RSV F1 gene;

FIG. 13 shows immunoblots of cell lysates from Sf9 cells infected with recombinant baculoviruses;

FIG. 14 shows the steps involved in constructing a baculovirus transfer vector (pD2);

FIG. 16 shows an SDS-PAGE gel and immunoblot of purified $F_{RSV}$-$HN_{PIV-3}$ chimeric protein;

FIG. 17 illustrates mutagenesis of a PIV-3 F gene; and

FIG. 18 shows the steps involved in the construction of a chimeric $F_{PIV-3}$-$G_{RSV}$ gene.

GENERAL DESCRIPTION OF INVENTION

Figure 4:
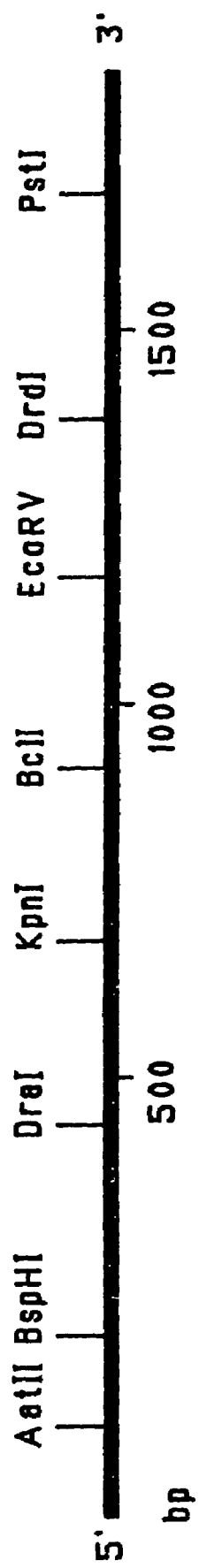
FIG. 4 shows the restriction map of the PIV-3 HN gene.
Figure 6:
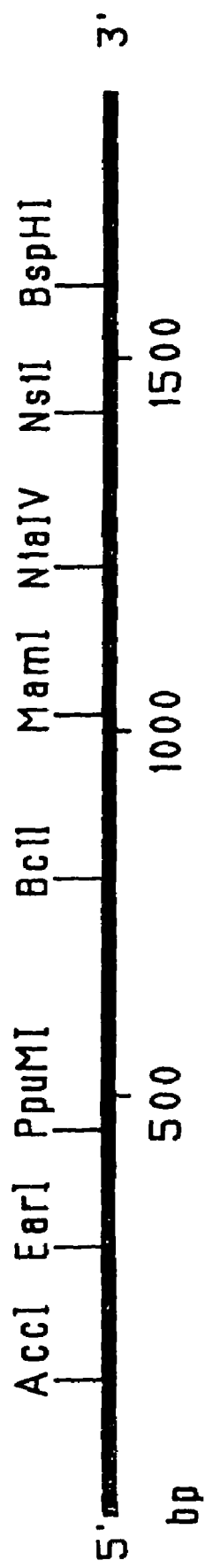
FIG. 6 shows the restriction map of the RSV F gene.

In the present invention, a chimeric molecule protective against two different major childhood diseases is provided. The present invention specifically relates to the formulation of various recombinant Parainfluenza virus (PIV)/Respiratory syncytial virus (RSV) immunogens to produce safe and efficacious vaccines capable of protecting infants and young children, as well as other susceptible individuals, against diseases caused by infection with both PIV and RSV. However, as described above, the present invention extends to the construction of multimeric hybrid genes containing genes coding for protective antigens from many pathogens. Such vaccines may be administered in any desired manner, such as a readily-injectable vaccine, intranasally or orally.

In the present invention, the inventors have specifically engineered several model PIV/RSV chimeric genes containing relevant sequences from selected genes coding for PIV-3 and RSV surface glycoproteins linked in tandem. All genes in the chimeric constructs described herein were obtained from recent clinical isolates of PIV-3 and RSV. The chimeric gene constructs may include gene sequences from either PIV-3 F or HN genes linked in tandem to either RSV F or G genes in all possible relative orientations and combinations.

The chimeric gene constructs provided herein may consist of either the entire gene sequences or gene segments coding for immunogenic and protective epitopes thereof. The natural nucleotide sequence of these genes may be modified by mutation while retaining antigenicity and such modifications may include the removal of putative pre-transcriptional terminators to optimize their expression in eukaryotic cells. The genes were designed to code for hybrid PIV-RSV surface glycoproteins linked in tandem in a single construct to produce gene products which elicit protective antibodies against both parainfluenza and respiratory syncytial viruses. Such multimeric hybrid genes consist of a gene sequence coding for a human PIV-3. F or HN protein or an immunogenic epitope-containing fragment thereof linked to a gene sequence coding for a human RSV G or F protein or an immunogenic epitope-containing fragment thereof. Specific gene constructs which may be employed include $F_{PIV-3}$-$F_{RSV}$, $F_{RSV}$-$HN_{PIV-3}$ and $F_{PIV-3}$-$G_{RSV}$ hybrid genes.

In addition, the present invention also extends to the construction of other multimeric genes, such as trimeric genes containing PIV and RSV genes or gene segments, linked in all possible relative orientations. For example:

$F_{PIV}$-$HN_{PIV}$-F or $G_{RSV}$
$F_{PIV}$-$F_{RSV}$-$G_{RSV}$
$HN_{PIV}$-$F_{RSV}$-$G_{RSV}$

The multimeric genes provided herein also may comprise at least one gene encoding at least one immunogenic and/or immunostimulating molecule.

The multimeric hybrid genes provided herein may be subcloned into appropriate vectors for expression in cellular expression systems. Such cellular expression systems may include bacterial, mammalian, insect and fungal, such as yeast, cells.

The chimeric proteins provided herein also may be presented to the immune system by the use of a live vector, including live viral vectors, such as recombinant poxviruses, adenoviruses, retroviruses, Semliki Forest viruses, and live bacterial vectors, such as Salmonella and mycobacteria (e.g. BCG).

Chimeric proteins, such as a PIV/RSV chimera, present in either the supernatants or cell lysates of transfected, transformed or infected cells then can be purified in any convenient manner.

To evaluate the immunogenicity and protective ability of the chimeric proteins, suitable experimental animals are immunized with either varying doses of the purified chimeric proteins, such as the PIV/RSV chimera, and/or live recombinant vectors as described above. Such chimeric proteins may be presented to the immune system by either the use of physiologically-acceptable vehicles, such as aluminum phosphate, or by the use of delivery systems, such as ISCOMS and liposomes. The chimeras also may be formulated to be capable of eliciting a mucosal response, for example, by conjugation or association with immunotargeting vehicles, such as the cholera toxin B subunit, or by incorporation into microparticles. The vaccines may further comprise means for delivering the multimeric protein specifically to cells of the immune system, such as toxin molecules or antibodies. To further enhance the immunoprotective ability of the chimeric proteins, they may be supplemented with other immunogenic and/or immunostimulating molecules. The chimeric PIV/RSV proteins specifically described herein may be formulated with an adjuvant, such as aluminum phosphate, to produce readily-injectable vaccines for protection against the diseases caused by both PIV-3 and RSV. The chimeric proteins also may be administered intranasally or orally. The chimeric proteins may be used in test kits for diagnosis of infection by PIV-3 and RSV.

The invention is not limited to the preparation of chimeric PIV-3 and RSV proteins, but is applicable to the production of chimeric immunogens composed of either the entire sequences or regions of the immunogenic proteins from at least two pathogens sequentially linked in a single molecule. Chimeric antigens also may be synthesized to contain the immunodominant epitopes of several proteins from different pathogens. These chimeric antigens may be useful as vaccines or as diagnostic reagents.

SEQUENCE IDENTIFICATION

Figure 9C:
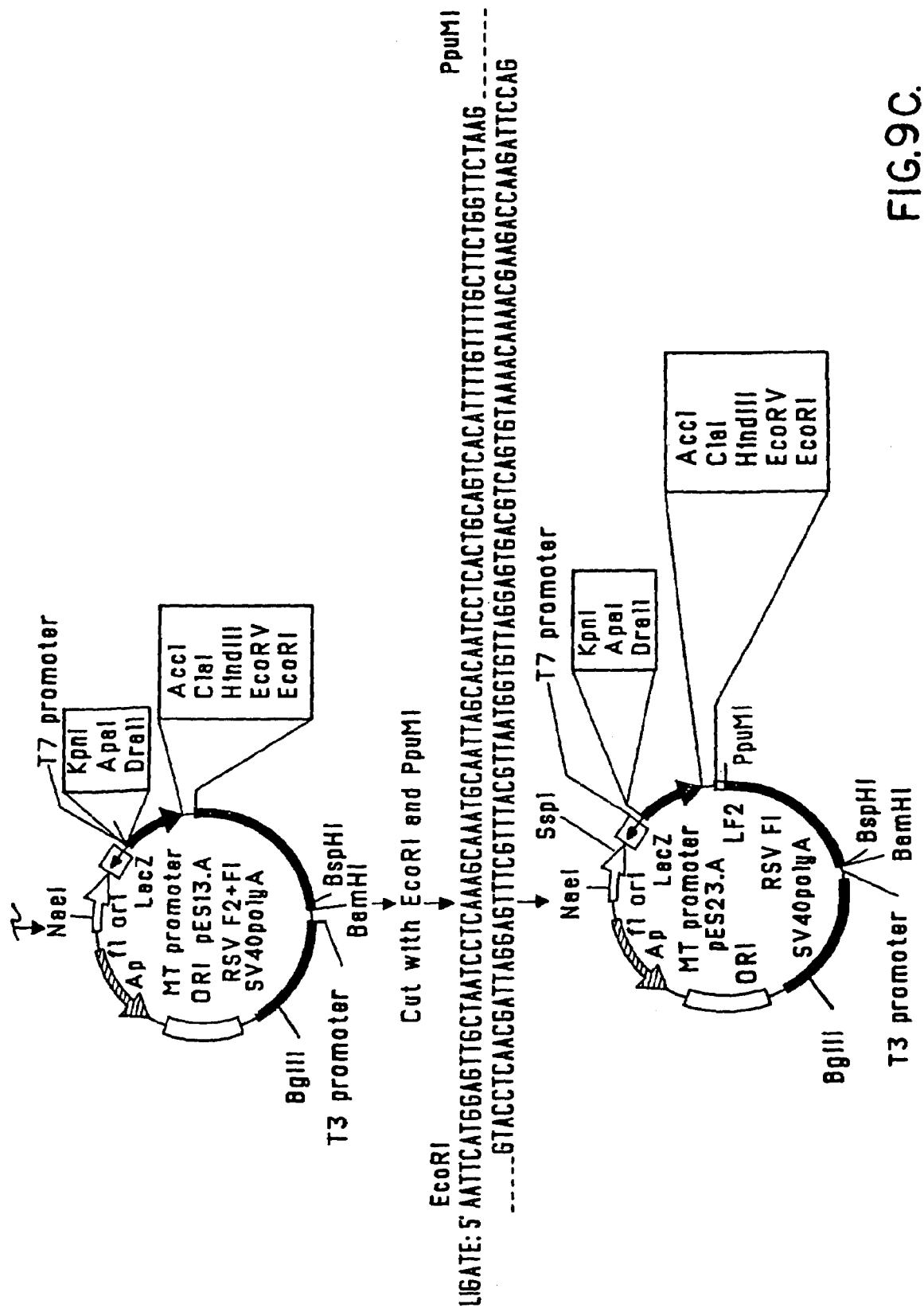
Figure 9D:
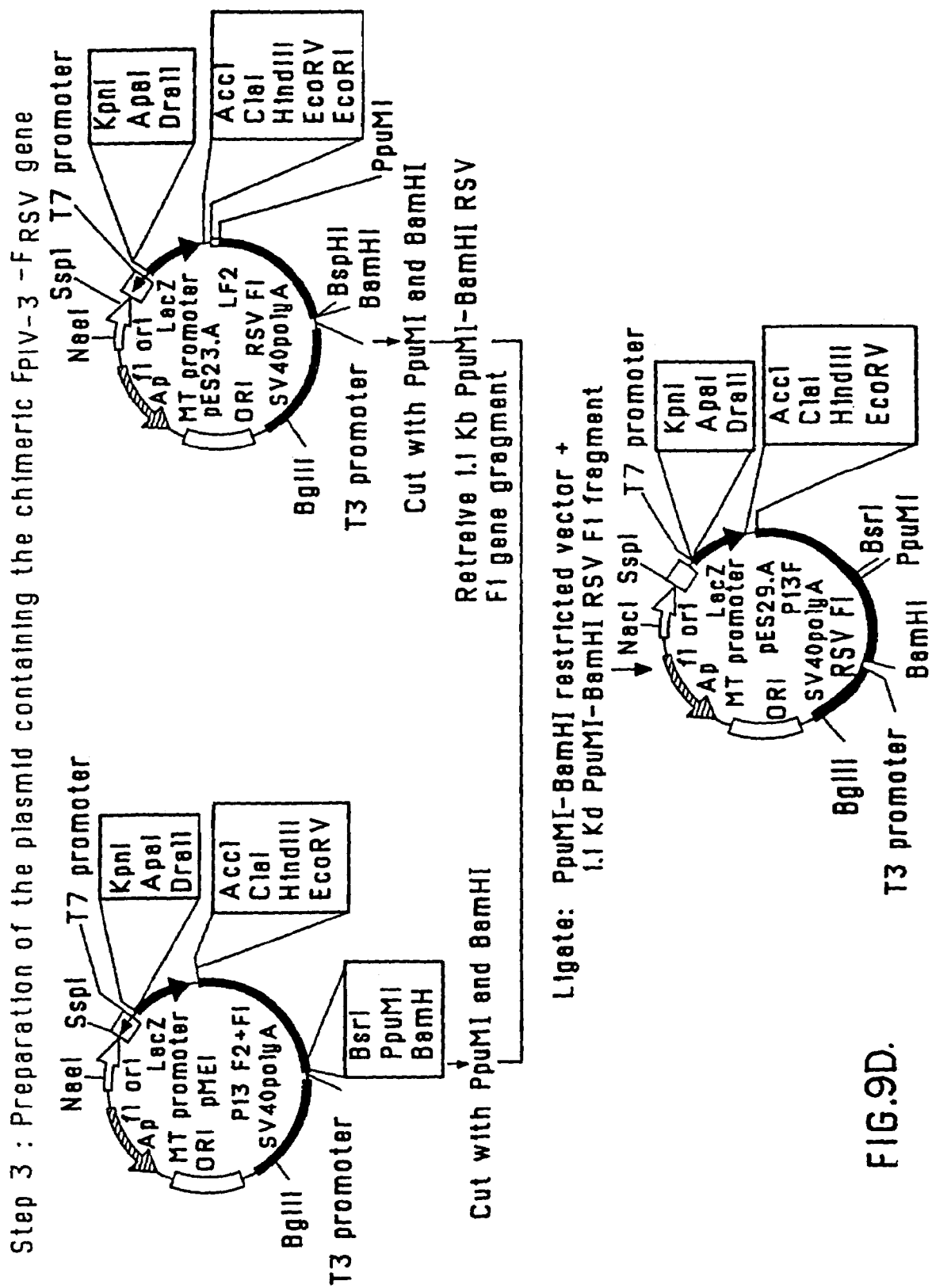
Figure 10A:
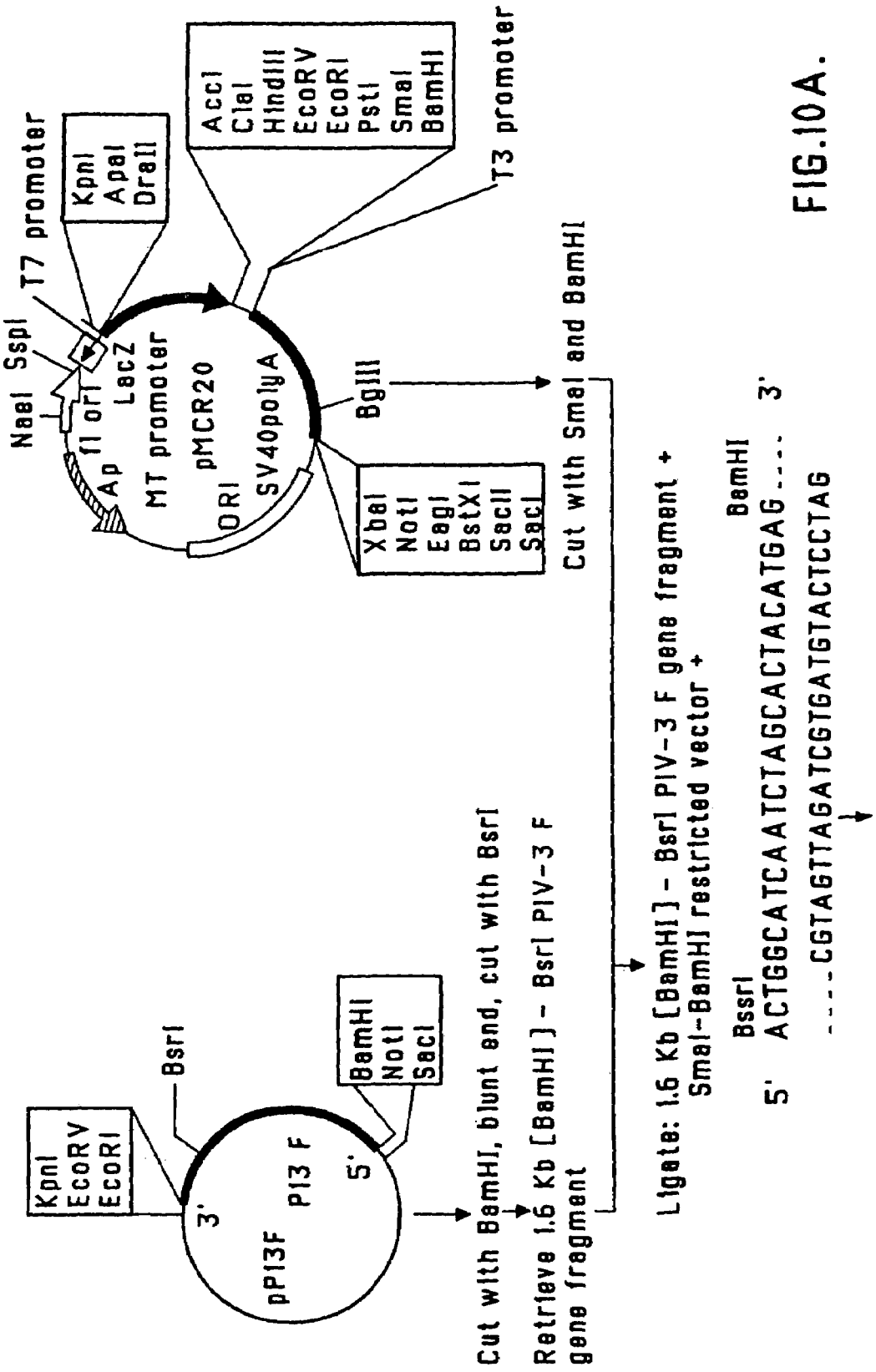
Figure 11:
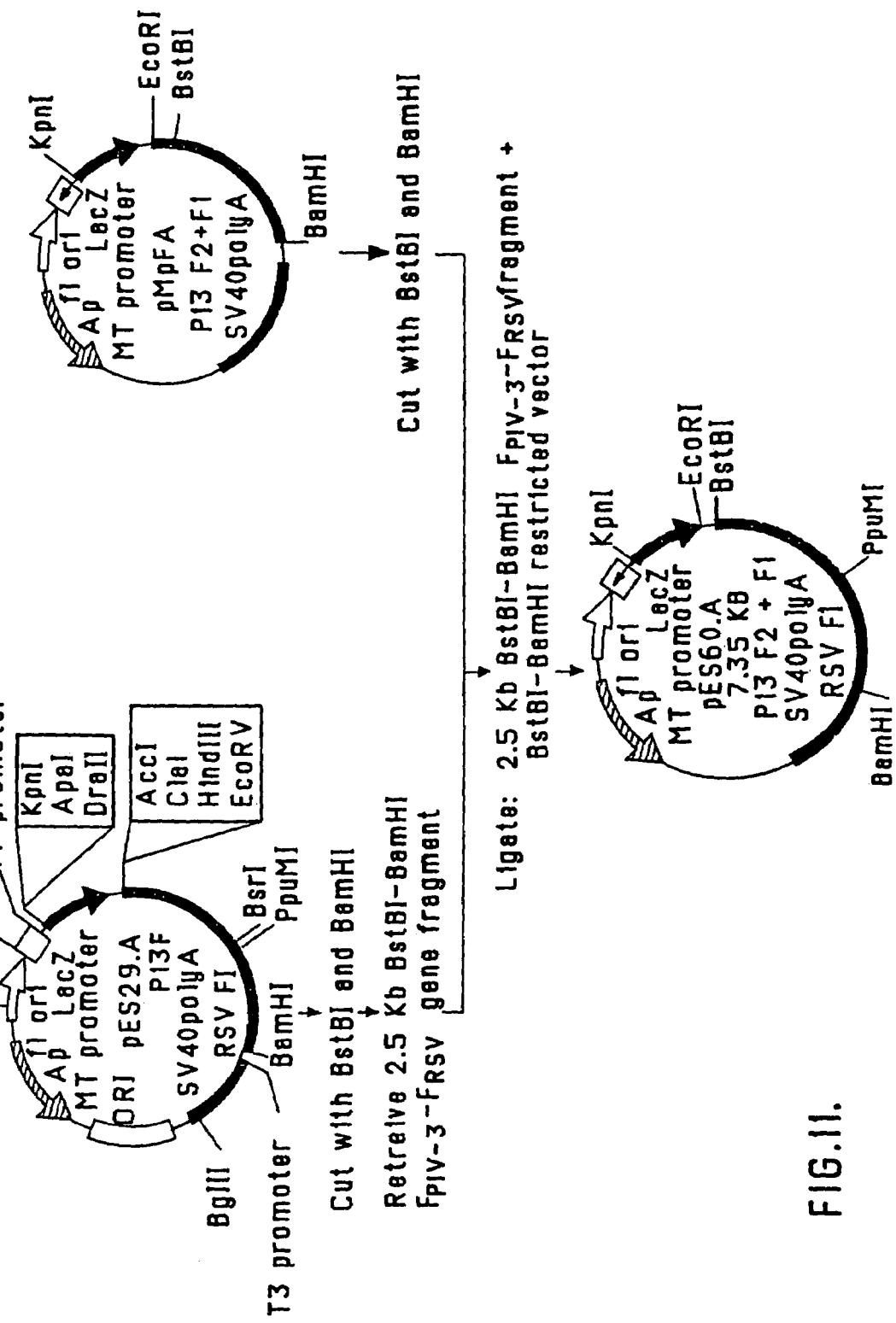
FIG. 11 shows the steps involved in the construction of an expression vector containing a chimeric $F_{PIV-3}$-$F_{RSV}$ gene containing a truncated PIV-3 F gene devoid of 5'-untranslated region linked to a truncated RSV F1 gene.
Figure 15B:
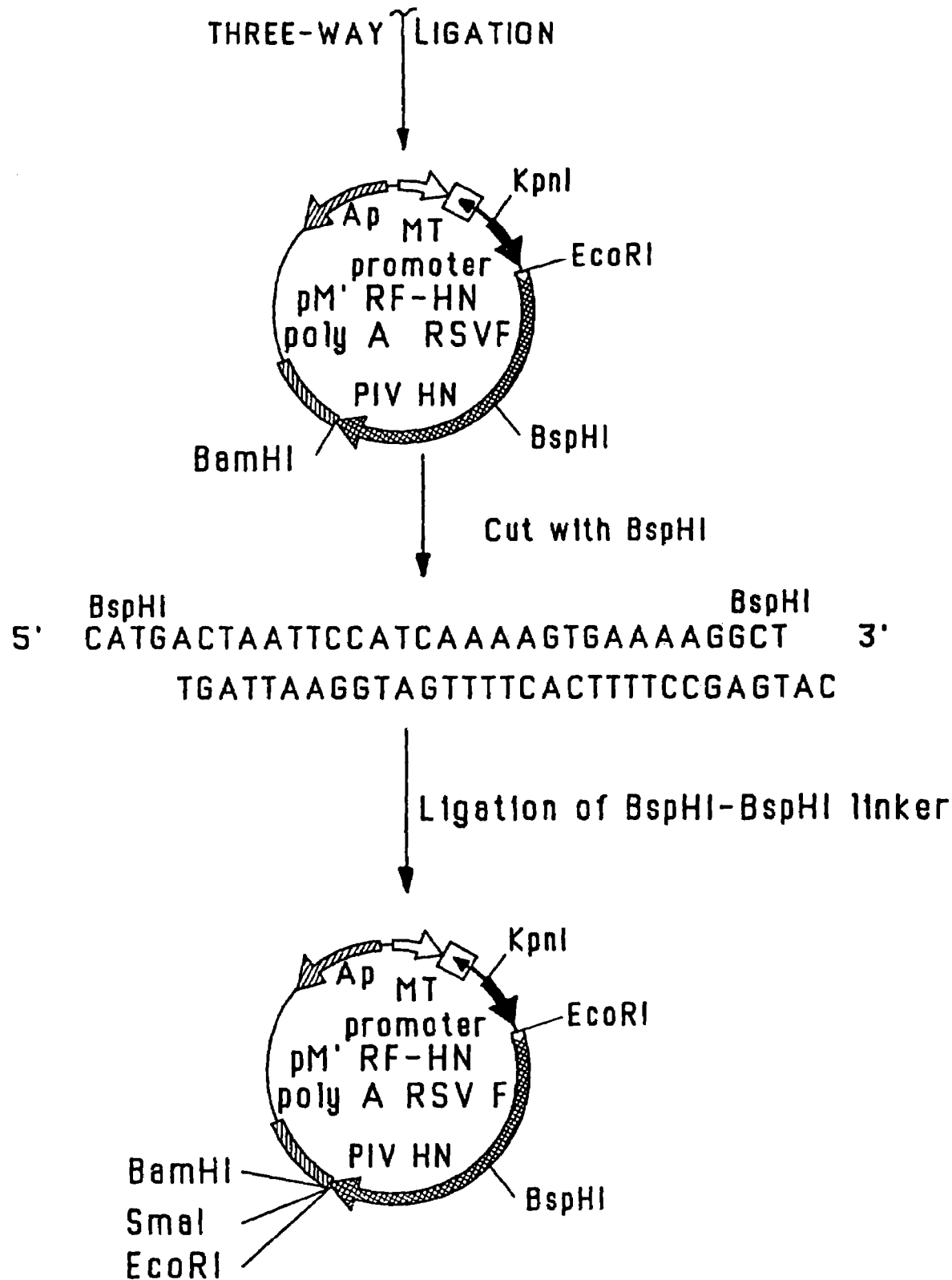
FIG. 15 shows the steps involved in construction of a chimeric $F_{RSV}$-$HN_{PIV-3}$ gene.

Several nucleotide and amino acid sequences are referred to in the disclosure of this application. The following table identifies the sequences and the location of the sequence:

| SEQ ID No. | Identification | Location |
|---|---|---|
| 1 | Nucleotide sequence for PCR-amplified PIV-3 F gene | FIG. 1, Example 1 |
| 2 | Amino acid sequence for PCR-amplified PIV-F protein | FIG. 1, Example 1 |
| 3 | Nucleotide sequence for PIV-3 HN gene | FIG. 3, Example 1 |
| 4 | Amino acid sequence for PIV-3 HN protein | FIG. 3, Example 1 |
| 5 | Nucleotide sequence for RSV F gene | FIG. 5, Example 1 |
| 6 | Amino acid sequence for RSV F protein | FIG. 5, Example 1 |
| 7 | Nucleotide sequence for RSV G gene | FIG. 7, Example 1 |
| 8 | Amino acid sequence for RSV G protein | FIG. 7, Example 1 |
| 9 | BsrI - BamHI oligo-nucleotide cassette | FIG. 9, Example 2 |
| 10 | BspHI - BamHI oligo-nucleotide cassette | FIG. 9, Example 2 |
| 11 | EcoRI - Ppu MI oligo-nucleotide cassette | FIG. 9, Example 2 |
| 12 | BrsI - BamHI oligo-nucleotide cassette | FIG. 10, Example 3 |
| 13 | EcoRI -Bsr BI oligo-nucleotide cassette | FIG. 10, Example 3 |
| 14 | EcoRV - EcoRI oligo-nucleotide cassette | FIG. 11, Example 5 |
| 15 | EcoRV - BamHI oligo-nucleotide cassette | FIG. 14, Example 8 |
| 16 | BspHI - BspHI oligo-nucleotide cassette | FIG. 15, Example 9 |
| 17 | Nucleotide sequence for PIV-3 F gene | Example 15 |
| 18 | Mutagenic oligo-nucleotide #2721 | FIG. 17, Example 15 |
| 19 | Nucleotide sequence for part of oligo-nucleotide #2721 | Example 15 |
| 20 | Oligonucleotide probe | Example 15 |

Deposit Information

Certain plasmid DNAs described and referred to herein have been deposited with the American Type Culture Collection (ATCC) located at Rockville, Md., USA, pursuant to the Budapest Treaty and prior to the filing of this application. The deposited purified plasmids will become available to the public upon grant of this U.S. patent application or upon publication of its corresponding European patent application, whichever first occurs. The invention described and claimed herein is not to be limited in scope by the plasmid DNAs of the constructs deposited, since the deposited embodiment is intended only as an illustration of the invention. The following purified plasmids were deposited at the ATCC with the noted accession numbers on Dec. 17, 1992:

| Plasmid | Example No. | Accession No. |
| --- | --- | --- |
| pAC DR7 | 5 | 75387 |
| pD2RF-HN | 9 | 75388 |
| pD2F-G | 16 | 75389 |

Any equivalent plasmids that can be used to produce equivalent antigens as described in this application are within the scope of the invention.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods for cloning and sequencing the PIV-3 and RSV genes as well as the procedures for sub-cloning the genes into appropriate vectors and expressing the gene constructs in mammalian and insect cells are not explicitly described in this disclosure but are well within the scope of those skilled in the art.

Example 1

This Example outlines the strategy used to clone and sequence the PIV-3 F, HN and RSV F, G genes (from a type A isolate). These genes were used in the construction of the $F_{PIV-3}$-$F_{RSV}$, $F_{RSV}$-$HN_{PIV-3}$, and $F_{PIV-3}$-$G_{RSV}$ chimeric genes detailed in Examples 2 to 4, 9 and 15, respectively.

Two PIV-3 F gene clones initially were obtained by PCR amplification of cDNA derived from viral RNA extracted from a recent clinical isolate of PIV-3. Two other PIV-3 F gene clones as well as the PIV-3 HN, RSV F and RSV G genes were cloned from a cDNA library prepared from mRNA isolated from MRC-5 cells infected with clinical isolates of either PIV-3 or RSV (type A isolate). The PIV-3 F (both PCR amplified and non-PCR amplified), PIV-3 HN, RSV F and RSV G gene clones were sequenced by the dideoxynucleotide chain termination procedure. Sequencing of both strands of the genes was performed by a combination of manual and automated sequencing.

The nucleotide (SEQ ID No: 1) and amino acid (SEQ ID No: 2) sequences of the PCR amplified PIV-3 F gene and F protein, respectively, are presented in FIG. 1 and the restriction map of the gene is shown in FIG. 2. Sequence analysis of the 1844 nucleotides of two PCR amplified PIV-3 F gene clones confirmed that the clones were identical. Comparison of the coding sequence of the PCR-amplified PIV-3 F gene clone with that of the published PIV-3 F gene sequence revealed a 2.6% divergence in the coding sequence between the two genes resulting in fourteen amino acid substitutions.

The nucleotide sequence of the non-PCR amplified PIV-3 F gene clone differed from the PCR amplified gene clone in the following manner: the non-PCR amplified clone had ten additional nucleotides (AGGACAAAAG) SEQ ID NO:21 at the 5' untranslated region of the gene and differed at four positions, 8 (T in PCR-amplified gene to C in non-PCR amplified gene), 512 (C in PCR-amplified gene to T in non-PCR amplified gene), 518 (G in PCR-amplified gene to A in non-PCR amplified gene) and 1376 (A in PCR-amplified gene to G in non-PCR amplified gene). These changes resulted in three changes in the amino acid sequence of the F protein encoded by the non-PCR amplified PIV-3 F gene. Serine (position 110), glycine (position 112), and aspartic acid (position 398) in the primary amino acid sequence of the F protein encoded by the PCR amplified PIV-3 F gene was changed to phenylalanine (position 110), glutamic acid (position 112) and glycine (position 398), respectively, in the primary amino acid sequence of the F protein encoded by the PCR amplified clone.

FIG. 3 shows the nucleotide (SEQ ID No: 3) and amino acid (SEQ ID No: 4) sequences of the PIV-3 HN gene and protein, respectively and the restriction map of the gene is presented in FIG. 4. Analysis of the 1833 nucleotide sequence from two HN clones confirmed that the sequences were identical. A 4.4% divergence in the coding sequence of the PIV-3 HN gene was noted when the sequence was compared to the published PIV-3 HN coding sequence. This divergence resulted in seventeen amino acid substitutions in the amino acid sequence of the protein encoded by the PIV-3 HN gene.

The nucleotide (SEQ ID No: 5) and amino acid (SEQ ID No: 6) sequences of the RSV F gene and RSV F protein, respectively, are shown in FIG. 5 and the restriction map of the gene is shown in FIG. 6. Analysis of the 1886 nucleotide sequence from two RSV F clones verified complete sequence homology between the two clones. Comparison of this nucleotide sequence with that reported for the RSV F gene revealed approximately 1.8% divergence in the coding sequence resulting in eleven amino acid substitutions.

The nucleotide (SEQ ID No: 7) and amino acid (SEQ ID No: 8) sequences of the RSV G gene and RSV G protein, respectively, are presented in FIG. 7 while the restriction map of the gene is outlined in FIG. 8. Comparison of the 920 nucleotide sequence of the G gene clone with the published G sequence (type A isolate) revealed a 4.2% divergence in the nucleotide sequence and a 6.7% divergence in the amino acid sequence of the gene product. This divergence resulted in twenty amino acid substitutions.

The full-length PIV-3 F (non-PCR amplified), PIV-3 HN, RSV F and RSV G genes were cloned into λgtll and subcloned into the multiple cloning site of a Bluescript M13-SK vector, either by blunt end ligation or using appropriate linkers. The PCR-amplified PIV-3 F gene was directly cloned into the Bluescript vector. The cloning vectors containing the PIV-3 F-PCR amplified, PIV-3 F non-PCR amplified, PIV-3 HN, RSV F and RSV G genes were named pPI3F, pPI3Fc, pPIVHN, pRSVF and pRSVG, respectively.

Example 2

This Example illustrates the construction of a Bluescript-based expression vector (pMCR20) containing the chimeric $F_{PIV-3}$-$F_{RSV}$ gene. This chimeric gene construct contains the 5' untranslated region of the PIV-3 F gene but lacks the hydrophobic anchor and cytoplasmic tail coding regions of both the PIV-3 and RSV F genes. The steps involved in the construction of this plasmid are summarized in FIG. 9.

To prepare the PIV-3 portion of the chimeric gene (FIG. 9, step 1), the full length PIV-3 gene lacking the transmembrane region and cytoplasmic tail coding regions was retrieved from plasmid pPI3F by cutting the polylinker with BamHI, blunt-ending the linearized plasmid with Klenow polymerase and cutting the gene with BsrI. A BsrI-BamHI oligonucleotide cassette (SEQ ID No: 9) containing a PpuMI site and three successive translational stop codons were ligated to the truncated 1.6 Kb [BamHI]-BsrI PIV-3 F gene fragment and cloned into the EcoRV-BamHI sites of a Bluescript M13-SK expression vector containing the human methallothionen promoter and the poly A and IVS sequences of the SV40 genome (designated pMCR20), to generate plasmid pME1.

To engineer the RSV F gene component of the chimeric construct (FIG. 9, step 2), the RSV F gene lacking the transmembrane region and cytoplasmic tail coding regions was retrieved from plasmid pRSVF by cutting the polylinker with EcoRI and the gene with BspHI. A synthetic BspHI-BamHI oligonucleotide cassette (SEQ ID No: 10) containing three successive translational stop codons was ligated to the 1.6 Kb truncated RSV F gene and cloned into the EcoRI-BamHI sites of the Bluescript based expression vector, pMCR20 to produce plasmid pES13A. Plasmid pES13A then was cut with EcoRI and PpuMI to remove the leader and F2 coding sequences from the truncated RSV F gene. The leader sequence was reconstructed using an EcoRI-PpuMI oligocassette (SEQ ID No: 11) and ligated to the RSV F1 gene segment to generate plasmid pES23A.

To prepare the chimeric $F_{PIV-3}$-$F_{RSV}$ gene (FIG. 9, step 3) containing the 5' untranslated region of the PIV-3 F gene linked to the truncated RSV F1 gene fragment, plasmid pME1 (containing the 1.6 Kb truncated PIV-3 F gene) first was cut with PpuMI and BamHI. The PpuMI-BamHI restricted pME1 vector was dephosphorylated with intestinal alkaline phosphatase. The 1.1 Kb RSV F1 gene fragment was retrieved from plasmid pES23A by cutting the plasmid with PpuMI and BamHI. The 1.1 Kb PpuMI-BamHI RSV F1 gene fragment was cloned into the PpuMI-BamHI sites of the dephosphorylated pME1 vector to generate plasmid pES29A. This chimeric gene construct contains the 5' untranslated region of the PIV-3 F gene but lacks the nucleotide sequences coding for the hydrophobic anchor domains and cytoplasmic tails of both the PIV-3 and RSV F proteins.

Example 3

This Example illustrates the construction of a Bluescript-based expression vector containing the PIV-3 F gene lacking both the 5' untranslated and transmembrane anchor and cytoplasmic tail coding regions. The steps involved in constructing this plasmid are outlined in FIG. 10.

Plasmid pPI3F containing the full length PIV-3 F gene was cut with BamHI, blunt ended with Klenow polymerase and then cut with BsrI to remove the transmembrane and cytoplasmic tail coding regions. The Bluescript-based expression vector, pMCR20, was cut with SmaI and BamHI. A synthetic BsrI-BamHI oligonucleotide cassette (SEQ ID No: 12) containing a translational stop codon was ligated with the 1.6 Kb blunt ended-BsrI PIV-3 F gene fragment to the SmaI-BamHI restricted pMCR20 vector to produce plasmid pMpFB. The PIV-3 F gene of this construct lacked the DNA fragment coding for the transmembrane and cytoplasmic anchor domains but contained the 5' untranslated region. To engineer a plasmid containing the PIV-3 F gene devoid of both the 5' untranslated region and the DNA fragment coding for the hydrophobic anchor domain, plasmid pMpFB was cut with EcoRI and BstBI. An EcoRI-BstBI oligocassette (SEQ ID No: 13) containing the sequences to reconstruct the signal peptide and coding sequences removed by the EcoRI-BstBI cut was ligated to the EcoRI-BstBI restricted pMpFB vector to produce plasmid pMpFA.

Example 4

This Example illustrates the construction of the chimeric $F_{PIV-3}$-$F_{RSV}$ gene composed of the truncated PIV-3 F gene devoid of the 5' untranslated region linked to the truncated RSV F1 gene. The steps involved in constructing this plasmid are summarized in FIG. 11.

To prepare this chimeric gene construct, plasmid pES29A (Example 2) was cut with BstBI and BamHI to release the 2.5 Kb BstBI-BamHI PI3-3 F-RSV F1 chimeric gene fragment. This BstBI-BamHI fragment was isolated from a low melting point agarose gel and cloned into the BstBI-BamHI sites of the dephosphorylated vector pMpFA to produce plasmid pES60A. This construct contained the PIV-3 F gene lacking both the 5' untranslated region and the hydrophobic anchor and cytoplasmic tail coding sequences linked to the F1 coding region of the truncated RSV F gene. This chimeric gene was subsequently subcloned into the baculovirus transfer vector (see Example 5).

Example 5

Figure 12B:
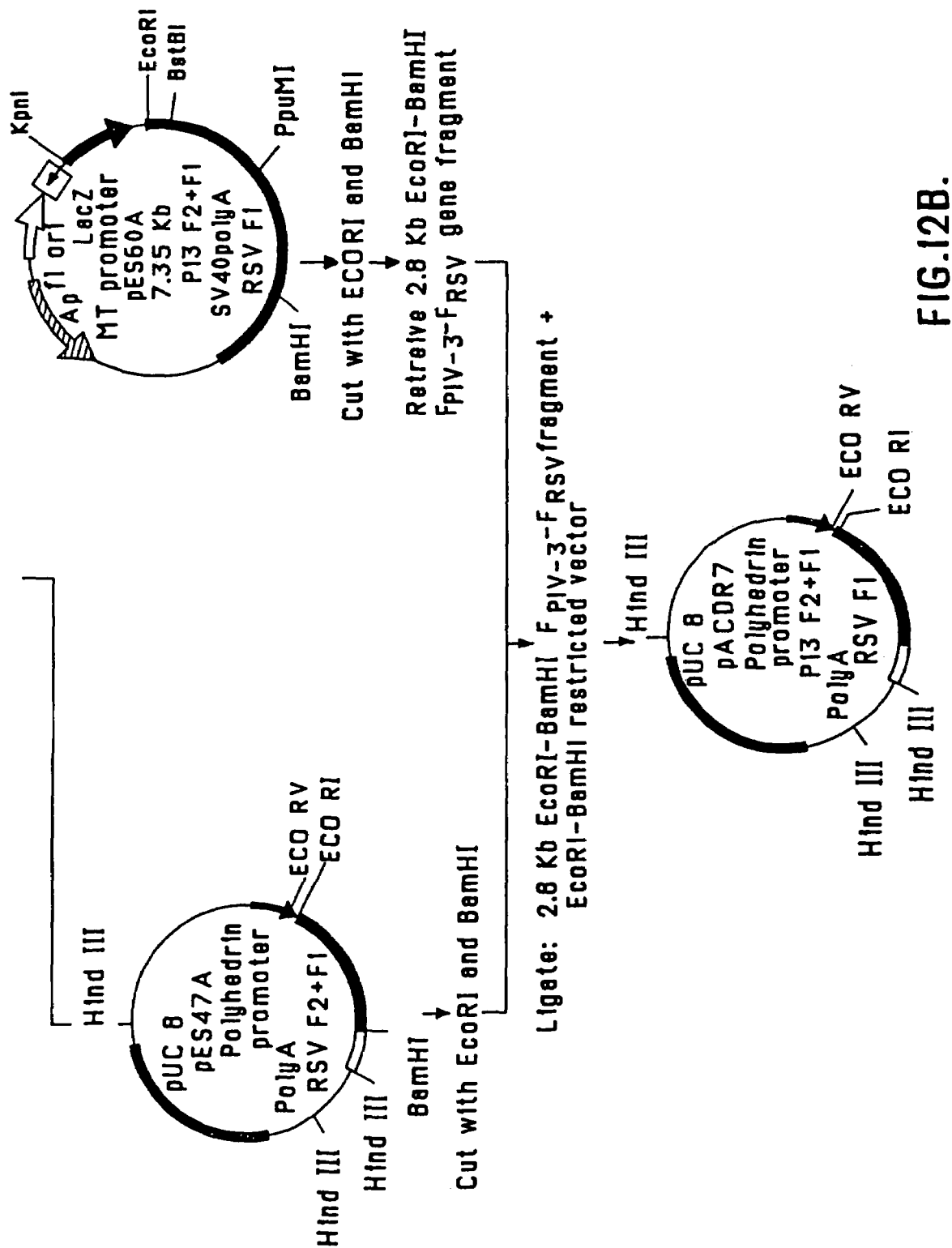

This Example illustrates the construction of the modified pAC 610 baculovirus transfer vector containing the native polyhedrin promoter and the chimeric $F_{PIV-3}$-$F_{RSV}$ gene consisting of the PIV-3 F gene lacking both the 5' untranslated sequence and the nucleotide sequence coding for the hydrophobic anchor domain and cytoplasmic tail linked to the truncated RSV F1 gene. Construction of this plasmid is illustrated in FIG. 12.

The pAC 610 baculovirus expression vector was modified to contain the native polyhedrin promoter in the following manner. Vector pAC 610 was cut with EcoRV and BamHI. The 9.4 Kb baculovirus transfer vector lacking the EcoRV-BamHI DNA sequence was isolated from a low melting point agarose gel and treated with intestinal alkaline phosphatase. In a 3-way ligation, an EcoRV-EcoRI oligonucleotide cassette (SEQ ID No: 14) containing the nucleotides required to restore the native polyhedrin promoter was ligated with the 1.6 Kb EcoRI-BamHI truncated RSV F gene fragment isolated from construct pES13A (Example 2, step 2) and the EcoRV-BamHI restricted pAC 610 phosphatase vector to generate plasmid pES47A. To prepare the pAC 610 based expression vector containing the chimeric $F_{PIV-3}$-$F_{RSV}$ gene, plasmid pES47A was first cut with EcoRI and BamHI to remove the 1.6 Kb truncated RSV F gene insert. The 2.8 Kb $F_{PIV-3}$-$F_{RSV}$ chimeric gene was retrieved by cutting plasmid pES60A (Example 4) with EcoRI and BamHI. The 2.8 Kb EcoRI-BamHI chimeric gene was ligated to the EcoRI-BamHI restricted pES47A vector to generate plasmid pAC DR7 (ATCC 75387).

Example 6

This Example outlines the preparation of plaque-purified recombinant baculoviruses containing the chimeric $F_{PIV-3}$-$F_{RSV}$ gene.

Spodoptera frugiperda (Sf9) cells were co-transfected with 1.0 µg wild-type AcMNPV DNA and 2.5 µg of $F_{PIV-3}$-$F_{RSV}$ plasmid DNA (plasmid pAC DR7—Example 5). Putative recombinant baculoviruses (purified once by serial dilution) containing the $F_{PIV-3}$-$F_{RSV}$ chimeric gene were identified by dot-blot hybridization. Lysates of insect cells infected with the putative recombinant baculoviruses were probed with the $^{32}$P-labelled $F_{PIV-3}$-$F_{RSV}$ chimeric gene insert. Recombinant baculoviruses were plaque-purified twice before being used for expression studies. All procedures were carried out according to the protocols outlined by M. D. Summers and G. E. Smith in "A Manual of Methods for Baculovirus Vectors and Insect Cell Culture Procedures", Texas Agricultural Experiment Station, Bulletin 1555, 1987.

Example 7

This Example illustrates the presence of the chimeric $F_{PIV-3}$-$F_{RSV}$ protein in supernatants and cell lysates of infected Sf9 cells.

Insect cells were infected with the plaque-purified recombinant baculoviruses prepared as described in Example 6 at a m.o.i. of 8. Concentrated supernatants from cells infected with the recombinant viruses were positive in a PIV-3 F specific ELISA. In addition, when lysates from $^{35}$S-methionine labelled infected cells were subjected to SDS-polyacrylamide gel electrophoresis and gels were analyzed by autoradiography, a strong band with apparent molecular weight of approximately 90 kDa was present in lysates of cells infected with the recombinant viruses but was absent in the lysates from wild-type infected cells. The presence of the chimeric $F_{PIV-3}$-$F_{RSV}$ protein in the lysates of cells infected with the recombinant baculoviruses was confirmed further by Western blot analysis using monospecific anti-PIV-3 F and anti-RSV F antisera and/or monoclonal antibodies (Mabs). Lysates from cells infected with the recombinant baculoviruses reacted with both anti-PIV-3 and anti-RSV antisera in immunoblots. As shown in the immunoblot of FIG. 13, lysates from cells infected with either the RSV F or $F_{PIV-3}$-$F_{RSV}$ recombinant baculoviruses reacted positively with the anti-F RSV Mab. As expected, lysates from cells infected with wild type virus did not react with this Mab. In addition, only lysates from cells infected with the chimeric $F_{PIV-3}$-$F_{RSV}$ recombinant viruses reacted with the anti-PIV-3 $F_1$ antiserum.

Example 8

This Example illustrates modification of the baculovirus transfer vector pVL1392 (obtained from Invitrogen), wherein the polyhedrin ATG start codon was converted to ATT and the sequence CCG was present downstream of the polyhedrin gene at positions +4, 5, 6. Insertion of a structural gene several base pairs downstream from the ATT codon is known to enhance translation. The steps involved in constructing this modified baculovirus transfer vector are outlined in FIG. 14.

The baculovirus expression vector pVL1392 was cut with EcoRV and BamHI. The 9.5 kb restricted pVL1392 vector was ligated to an EcoRV-BamHI oligonucleotide cassette (SEQ ID No: 15) to produce the pD2 vector.

Example 9

This Example illustrates the construction of the pD2 baculovirus expression vector containing the chimeric $F_{RSV}$-$HN_{PIV-3}$ gene consisting of the truncated RSV F and PIV-3 HN genes linked in tandem. The steps involved in constructing this plasmid are summarized in FIG. 15.

To engineer the $F_{RSV}$-$F_{PIV-3}$ gene, the RSV F gene lacking the nucleotide sequence coding for the transmembrane domain and cytoplasmic tail of the RSV F glycoprotein was retrieved from plasmid pRSVF (Example 1) by cutting the polylinker with EcoRI and the gene with BspHI. The PIV-3 HN gene devoid of the DNA fragment coding for the hydrophobic anchor domain was retrieved from plasmid pPIVHN (Example 1) by cutting the gene with BspHI and the polylinker with BamHI. The 1.6 Kb EcoRI-BspHI RSV F gene fragment and the 1.7 Kb BspHI-BamHI PIV-3 HN gene fragment were isolated from low melting point agarose gels. For cloning purposes, the two BspHI sites in the Bluescript based mammalian cell expression vector, pMCR20, were mutated. Mutations were introduced in the BspHI sites of the pMCR20 by cutting the expression vector with BspHI, treating both the BspHI restricted vector and the 1.1 Kb fragment released by the BspHI cut with Klenow polymerase and ligating the blunt-ended 1.1 Kb fragment to the blunt-ended Bluescript-based expression vector to generate plasmid pM'. Since insertion of the 1.1 Kb blunt-end fragment in the mammalian cell expression vector in the improper orientation would alter the $Amp^r$ gene of the Bluescript-based expression vector, only colonies of HB101 cells transformed with the pM' plasmid DNA with the 1.1 Kb blunt-ended fragment in the proper orientation could survive in the presence of ampicillin. Plasmid DNA was purified from ampicillin-resistant colonies of HB101 cells transformed with plasmid PM' by equilibrium centrifugation in cesium chloride-ethidium bromide gradients. The 1.6 Kb EcoRI-BspHI RSV F and 1.7 Kb BspHI-BamHI PIV-3 HN gene fragments were directly cloned into the EcoRI-BamHI sites of vector pM' in a 3-way ligation to generate plasmid pM' RF-HN.

To restore specific coding sequences of the RSV F and PIV-3 HN genes removed by the BspHI cut, a BspHI-BspHI oligonucleotide cassette (SEQ ID No: 16) containing the pertinent RSV F and PIV-3 HN gene sequences was ligated via the BspHI site to the BspHI-restricted plasmid pM' RF-HN to produce plasmid pM RF-HN. Clones containing the BspHI-BspHI oligonucleotide cassette in the proper orientation were identified by sequence analysis of the oligonucleotide linker and its flanking regions.

To clone the chimeric $F_{RSV}$-$HN_{PIV-3}$ gene into the baculovirus expression vector pD2 (Example 8), the $F_{RSV}$-$HN_{PIV-3}$ truncated gene first was retrieved from plasmid pM RF-HN by cutting the plasmid with EcoRI. The 3.3 Kb $F_{RSV}$-$HN_{PIV-3}$ gene then was cloned into the EcoRI site of the baculovirus transfer vector plasmid pD2 to generate plasmid pD2 RF-HN (ATCC 75388). Proper orientation of the 3.3 Kb EcoRI $F_{RSV}$-$HN_{PIV-3}$ chimeric gene insert in plasmid pD2 RF-HN was confirmed by sequence analysis.

Example 10

This Example outlines the preparation of plaque-purified recombinant baculoviruses containing the chimeric $F_{RSV}$-$HN_{PIV-3}$ gene.

Spodoptera frugiperda (Sf9) cells were co-transfected with 1 µg wild-type AcNPV DNA and 2 µg of $F_{RSV}$-$HN_{PIV-3}$ plasmid DNA (plasmid pD2 RF-HN-Example 9). Putative recombinant baculoviruses (purified once by serial dilution) containing the $F_{RSV}$-$HN_{PIV-3}$ chimeric gene were identified by dot-blot hybridization. Lysates of insect cells infected with the putative recombinant baculoviruses were probed with the $^{32}$P-labelled RSV F or PTV-3 HN gene oligonucleotide probes. Recombinant baculoviruses were plaque-purified three times before being used for expression studies. All procedures were carried out according to the protocols outlined by Summers and Smith (Example 6).

Example 11

This Example illustrates the presence of the chimeric $F_{RSV}$-$HN_{PIV-3}$ protein in supernatants of infected Sf9 and High 5 cells.

Insect cells (Sf9 and High 5), maintained in serum free medium EX401, were infected with the plaque purified recombinant baculoviruses of Example 10 at a m.o.i. of 5 to 10 pfu/cell. Supernatants from cells infected with the recombinant baculoviruses tested positive for expressed protein in both the RSV-F and PIV-3 HN specific ELISAS. In addition, supernatants from infected cells reacted positively with both an anti-F RSV monoclonal antibody and anti-HN peptide antisera on immunoblots. A distinct band of approximately 105 kDa was present in the immunoblots. These results confirm the secretion of the chimeric $F_{RSV}$-$F_{PIV-3}$ protein into the supernatant of Sf9 and High 5 cells infected with the recombinant baculoviruses.

Example 12

This Example illustrates the purification of the chimeric $F_{RSV}$-$HN_{PIV-3}$ protein from the supernatants of infected High 5 cells.

High 5 cells, maintained in serum free medium, were infected with the plaque purified recombinant baculoviruses of Example 10 at a m.o.i of 5 pfu/cell. The supernatant from virus infected cells was harvested 2 days post-infection. The soluble $F_{RSV}$-$HN_{PIV-3}$ chimeric protein was purified from the supernatants of infected cells by immunoaffinity chromatography using an anti-HN PIV-3 monoclonal antibody. The anti-HN monoclonal antibody was coupled to CNBr-activated Sepharose 4B by conventional techniques. The immunoaffinity column was washed with 10 bed volumes of washing buffer (10 mM Tris-HCl pH 7.5, 150 mM NaCl, 0.02% v/v TRITON-X 100 (Trademark for a non-ionic detergent which is octadienyl phenol (ethylene glycol)$_{10}$)) prior to use. After sample loading, the column was washed with 10 bed volumes of washing buffer followed by 3 bed volumes of high salt buffer (10 mm Tris-HCl pH 7.5, 500 mM NaCl, 0.02% v/v TRITON-X 100 (Trademark for a non-ionic detergent which is octadienyl phenol (ethylene glycol)$_{10}$)). The chimeric $F_{RSV}$-$HN_{PIV-3}$ protein was eluted from the immunoaffinity column with 100 mM glycine, pH 2.5, in the presence of 0.02% TRITON X-100 (Trademark for a non-ionic detergent which is octadienyl phenol (ethylene glycol)$_{10}$). Eluted protein was neutralized immediately with 1M. Tris-HCl, pH 10.7.

Polyacrylamide gel electrophoretic analysis (FIG. 16, panel A) of the immunoaffinity-purified $F_{RSV}$-$HN_{PIV-3}$ protein revealed the presence of one major protein band with an apparent molecular weight of 105 kDa. The purified protein reacted with both an anti-RSV F monoclonal antibody and anti-HN peptide antisera on immunoblots (FIG. 16, panel B, lanes 1 and 2, respectively).

Example 13

This Example illustrates the immunogenicity of the $F_{RSV}$-$HN_{PIV-3}$ protein in guinea pigs.

Groups of four guinea pigs were injected intramuscularly with either 1.0 or 10.0 µg of the chimeric $F_{RSV}$-$HN_{PIV-3}$ protein purified as described in Example 12 and adjuvanted with aluminum phosphate. Groups of control animals were immunized with either placebo, or live PIV-3 or RSV (administered intranasally). Guinea pigs were bled 2 and 4 weeks after the primary injection and boosted at 4 weeks with an equivalent dose of the antigen formulation. Serum samples also were taken 2 and 4 weeks after the booster dose. To assess the ability of the chimeric protein to elicit PIV-3 and RSV-specific antibody responses, sera samples were analyzed for the presence of PIV-3 specific hemagglutination inhibiting and neutralizing antibodies as well as RSV neutralizing antibodies. As summarized in Table 1 below (the Tables appear at the end of the disclosure), the sera of animals immunized with two 10 µg doses of the chimeric protein had titres of PIV-3 specific hemagglutination inhibition (HAI) and PIV-3/RSV neutralizing antibodies at the 6 and 8 week time points which were equivalent to the levels obtained following intranasal inoculation with either live PIV-3 or RSV. In addition, animals immunized with only two 1 µg doses of the chimeric protein elicited strong PIV-3 and RSV specific neutralizing antibodies. These results confirmed the immunogenicity of both the RSV and PIV-3 components of the chimeric protein and provided confirmatory evidence that a single recombinant immunogen can elicit neutralizing antibodies against both RSV and PIV-3.

Example 14

This Example illustrates the immunogenicity and protective ability of the $F_{RSV}$-$HN_{PIV-3}$ protein in cotton rats.

Groups of eight cotton rats were injected intramuscularly with either 1.0 or 10.0 µg of the chimeric $F_{RSV}$-$HN_{PIV-3}$ protein (prepared as described in Example 12) adjuvanted with aluminum phosphate. Groups of control animals were immunized with either placebo (PBS+aluminum phosphate) or live PIV-3 or RSV (administered intranasally). Cotton rats were bled 4 weeks after the primary injection and boosted at 4 weeks with an equivalent dose of the antigen formulation. Serum samples were also taken 1 week after the booster dose. As shown in Table 2 below, data from the 4-week bleed demonstrated that both a 1 and 10 µg dose of the chimeric protein was capable of inducing a strong primary response. Reciprocal mean $log_2$ PIV-3 specific HAI and PIV-3/RSV neutralizing titers were equivalent to the titres obtained with live PIV-3 and RSV. Thus, a single inoculation of the chimeric protein was sufficient to elicit neutralizing antibodies against both PIV-3 and RSV. Strong neutralizing PIV-3 and RSV titres also were observed following the booster dose (5 week bleed). These results provide additional evidence that both the RSV and PIV-3 components of the chimeric protein are highly immunogenic.

To assess the ability of the chimeric immunogen to simultaneously protect animals against both RSV and PIV-3, four cotton rats from each group were challenged intranasally with 100 $TCID_{50}$ units of either PIV-3 or RSV. Animals were killed 4 days after virus challenge. Virus titers were determined in lung lavages. As shown in Table 3 below, animals immunized with either 1 or 10 µg of the chimeric $F_{RSV}$-$HN_{PIV-3}$ protein were completely protected against challenge with either PIV-3 or RSV. These results provide evidence that the chimeric protein is not only highly immunogenic but can also simultaneously protect cotton rats against disease caused by both PIV-3 and RSV infection.

Example 15

Figure 18:
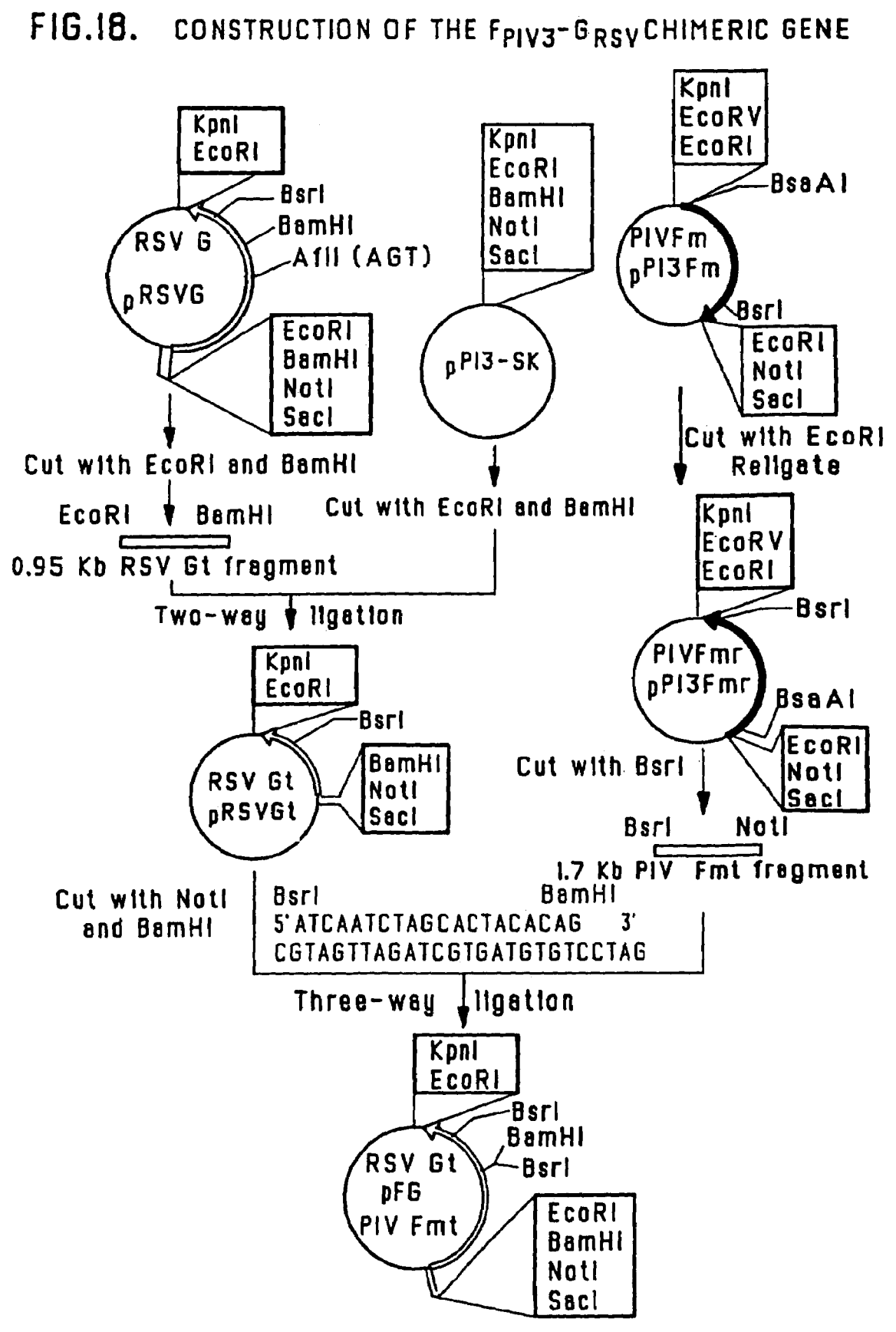

This Example illustrates the construction of a Bluescript M13-SK vector containing the chimeric $F_{PIV-3}$-$G_{RSV}$ gene. This chimeric gene construct contains the 5' untranslated region of a mutated PIV-3 F gene but lacks the nucleotide sequence coding for the hydrophobic anchor and cytoplasmic tail domains of both a mutated PIV-3 F and the native RSV G genes. The steps involved in constructing this plasmid are outlined in FIGS. 17 and 18.

The first step (FIG. 17) involved in preparing the PIV-3 F component of the chimeric $F_{PIV-3}$-$G_{RSV}$ gene construct was to eliminate the putative pre-termination sites within the 18 nucleotide long sequence 5' CAAGAAAAAGGAATAAAA 3' (SEQ ID No: 17) located between positions 857 and 874 of the non PCR-amplified PIV-3 F gene and positions 847 and 864 of the PCR-amplified PIV-3 F gene (see FIG. 1). To this end, the PIV-F cDNA of the non-PCR amplified PIV-3 F gene was cut at the BsaAI and EcoRI sites. The BsaAI-EcoRI PIV F gene fragment was cloned into the EcoRI site of a Bluescript M13-SK vector using an EcoRI-BsaAI linker. The 857-874 target region of the PIV-3 F gene (non-PCR amplified) then was mutated by oligonucleotide-mediated mutagenesis using the method of Morinaga et al. [1984, Biotechnology 2: 636-639]. Plasmid pPI3Fc (Example 1) was cut with ScaI in the Amp$^r$ gene and dephosphorylated with alkaline phosphatase (plasmid #1). A second sample of plasmid pPI3Fc was cut with BstEII and NsiI to produce a 3.9 Kb restricted plasmid, lacking the 0.9 Kb BstEII-NsiI fragment of the PIV-3 F gene (plasmid #2). A mutagenic 78-mer synthetic oligonucleotide (#2721 shown in FIG. 17-SEQ ID. No: 18)) containing the sequence 5' CAGGAGAAGGGTATCAAG 3' (SEQ ID No: 19) was synthesized to specifically mutate the 857-874 DNA segment without changing the F protein sequence. This oligonucleotide was added to plasmid DNAs #1 and #2, denatured at 100° C. for 3 min. and renatured by gradual cooling. The mixture then was incubated in the presence of DNA polymerase, dNTPs and T4 ligase and transformed into HB101 cells. Bacteria containing the 1.8 Kb mutated PIV-3 F gene were isolated on YT agar plates containing 100 µg/ml ampicillin. Hybridization with the oligonucleotide probe 5' AGGAGAAGGGTATCAAG 3' (SEQ ID No: 20) was used to confirm the presence of the mutated PIV-3 F gene. The mutated gene sequence was confirmed by DNA sequencing. The plasmid containing the mutated PIV-3 gene was designated pPI3Fm.

The second step (FIG. 18) in the engineering of the chimeric gene construct involved constructing a Bluescript based vector to contain the truncated PIV-3 Fm gene lacking the nucleotide sequence coding for the transmembrane anchor domain and cytoplasmic tail of the PIV-3 F protein linked in tandem with the RSV G gene lacking both the 5' leader sequence and the nucleotide sequence coding for the transmembrane anchor domain and cytoplasmic tail of the G glycoprotein.

To prepare this chimeric gene, the orientation of the mutated PIV-F gene in plasmid pPI3Fm first was reversed by EcoRI digestion and religation to generate plasmid pPI3Fmr. To prepare the PIV-3 F gene component of the chimeric gene, plasmid pPI3Fmr was cut with NotI and BsrI to release the 1.7 Kb truncated PIV-3 F gene. To prepare the RSV G component, the 0.95 Kb RSV-G gene lacking both the 5' leader sequence and the DNA segment encoding the G protein anchor domain and cytoplasmic tail was released from plasmid pRSVG (Example 1) by cutting the polylinker with EcoRI and the gene with BamHI. The 0.95 Kb EcoRI-BamHI RSV G gene fragment was subcloned into the EcoRI-BamHI sites of a restricted Bluescript vector, pM13-SK, to produce plasmid pRSVGt. The 0.95 Kb EcoRI-BamHI G gene fragment and the 1.5 Kb NotI-BsrI truncated PIV-3 F gene were linked via a BsrI-BamHI oligonucleotide cassette (SEQ ID No: 9) restoring the F and G gene coding sequences and cloned into the pRSVGt vector restricted with BamHI and NotI in a 3-way ligation. The plasmid thus generated was designated pFG.

Example 16

This Example outlines the construction of the pD2 baculovirus transfer vector (described in Example 8) containing the chimeric $F_{PIV-3}$-$G_{RSV}$ gene consisting of a mutated PIV-3 F gene lacking the hydrophobic anchor and cytoplasmic coding regions linked to the RSV G gene lacking both the 5' leader sequence and the nucleotide sequences encoding the transmembrane anchor domain and cytoplasmic tail of the G protein.

To prepare this construct, plasmid pFG (Example 15) was cut with EcoRI to release the 2.6 Kb $F_{PIV-3}$-$G_{RSV}$ chimeric gene. The 2.6 Kb EcoRI restricted chimeric gene fragment then was sub-cloned into the EcoRI site of the dephosphorylated pD2 vector to generate the 12.1 Kb plasmid pD2F-G (ATCC 75389).

Example 17

This Example outlines the preparation of plaque-purified recombinant baculoviruses containing the chimeric $F_{PIV-3}$-$G_{RSV}$ gene.

Spodoptera frugiperda (Sf9) cells were co-transfected with 2 µg of pD2F-G plasmid DNA (Example 16) and 1 µg of linear wild-type AcNPV DNA (obtained from Invitrogen). Recombinant baculoviruses containing the $F_{PIV-3}$-$G_{RSV}$ gene were plaque-purified twice according to the procedure outlined in Example 10.

Example 18

This Example illustrates the presence of the chimeric $F_{PIV-3}$-$G_{RSV}$ protein in the supernatant of Sf9 and High 5 cells infected with the recombinant baculoviruses.

Sf9 and High 5 cells were infected with recombinant baculoviruses containing the $F_{PIV-3}$-$G_{RSV}$ gene (Example 16) at a m.o.i. of 5 to 10 pfu/cell. The supernatant of cells infected with the recombinant viruses tested positive for expressed protein in the PIV-3 F specific ELISA. Supernatants of infected cells reacted with both anti-F PIV-3 and anti-G RSV monoclonal antibodies in immunoblots. These results confirm the presence of the chimeric $F_{PIV-3}$-$G_{RSV}$ protein in the supernatants of infected Sf9 and High 5 cells.

Example 19

This Example outlines the preparation of recombinant vaccinia viruses expressing the $F_{PIV-3}$-$F_{RSV}$ and $F_{RSV}$-$HN_{PIV-3}$ genes.

Vaccinia virus recombinant viruses expressing the $F_{PIV-3}$-$F_{RSV}$ (designated vP1192) and $F_{RSV}$-$HN_{PIV-3}$ (designated vP1195) genes were produced at Virogenetics Corporation (Troy, N.Y.) (an entity related to assignee hereof) using the COPAK host-range selection system. Insertion plasmids used in the COPAK host-range selection system contained the vaccinia K1L host-range gene [Perkus et al., (1990) Virology 179:276-286] and the modified vaccinia H6 promoter [Perkus et al. (1989), J. Virology 63:3829-3836]. In these insertion plasmids, the K1L gene, H6 promoter and polylinker region are situated between Copenhagen strain vaccinia flanking arms replacing the ATI region [open reading frames (ORFs) A25L, A26L; Goebel et al., (1990), Virology 179: 247-266; 517-563]. COPAK insertion plasmids are designed for use in in vivo recombination using the rescue virus NYVAC (vP866) (Tartaglia et al., (1992) Virology 188: 217-232). Selection of recombinant viruses was done on rabbit kidney cells.

Recombinant viruses, vP1192 and vP1195 were generated using insertion plasmids pES229A-6 and PSD.RN, respectively. To prepare plasmid pES229A-6 containing the $F_{PIV-3}$-$F_{RSV}$ gene, the COPAK-H6 insertion plasmid pSD555 was cut with SmaI and dephosphorylated with intestinal alkaline phosphatase. The 2.6 Kb $F_{PIV-3}$-$F_{RSV}$ gene was retrieved from plasmid pES60A (Example 4) by cutting the plasmid with EcoRI and BamHI. The 2.6 Kb EcoRI-BamHI $F_{PIV-3}F_{RSV}$ gene was blunt ended with Klenow polymerase, isolated from a low melting point agarose gel and cloned into the SmaI site of the COPAK-H6 insertion plasmid pSD555 to generate plasmid pES229A-6. This positioned the $F_{PIV-3}$-$F_{RSV}$ ORF such that the 5' end is nearest the H6 promoter.

To prepare plasmid PSD.RN, the pSD555 vector first was cut with SmaI and BamHI. Plasmid pM RF-HN (Example 9) containing the truncated $F_{RSV}$-$HN_{PIV-3}$ gene was cut with ClaI, blunt ended with Klenow polymerase and then cut with BamHI. The 3.3 Kb $F_{RSV}$-$HN_{PIV\text{-}3}$ gene was cloned into the SmaI-BamHI sites of the pSD555 vector to generate plasmid PSD.RN. This positioned the $F_{RSV}$-$HN_{PIV\text{-}3}$ ORF such that the H6 5' end is nearest the H6 promoter.

Plasmids pES229A-6 and PSD.RN were used in in vitro recombination experiments in vero cells with NYVAC (vP866) as the rescuing virus. Recombinant progeny virus was selected on rabbit kidney (RK)-13 cells (ATCC #CCL37). Several plaques were passaged two times on RK-13 cells. Virus containing the chimeric genes were confirmed by standard in situ plaque hybridization [Piccini et al. (1987), Methods in Enzymology, 153:545-563] using radiolabeled probes specific for the PIV and RSV inserted DNA sequences. Plaque purified virus containing the $F_{PIV\text{-}3}$-$F_{RSV}$ and $F_{RSV}$-$HN_{PIV\text{-}3}$ chimeric genes were designated vP1192 and vP1195, respectively.

Radioimmunoprecipitation was done to confirm the expression of the chimeric genes in vP1192 and vP1195 infected cells. These assays were performed with lysates prepared from infected Vero cells [according to the procedure of Taylor et al., (1990) J. Virology 64, 1441-450] using guinea pig monospecific PIV-3 anti-HN and anti-F antiserum and rabbit anti-RSV F antiserum. Both the anti-PIV F and anti-RSV F antisera precipitated a protein with an apparent molecular weight of approximately 90 koa from vP1192 infected Vero cells. Both anti-RSV F and guinea pig anti-PIV HN antisera precipitated a protein with an apparent molecular weight of approximately 100 kDa from vP1195 infected cells. These results confirmed the production of the $F_{PIV\text{-}3}$-$F_{RSV}$ and $F_{RSV}$-$HN_{PIV\text{-}3}$ chimeric proteins in Vero cells infected with the recombinant poxviruses.

SUMMARY OF DISCLOSURE

In summary of the disclosure, the present invention provides multimeric hybrid genes which produce chimeric proteins capable of eliciting protection against infection by a plurality of pathogens, particularly PIV and RSV. Modifications are possible within the scope of this invention.

TABLE 1

Secondary antibody response of guinea pigs immunized with the chimeric $F_{RSV}$-$HN_{PIV\text{-}3}$ protein

| Antigen | Dose | HAI Titre[a] ($log_2$ ± s.e.) | | Neutralization Titre[b] ($log_2$ ± s.e.) | | | |
|---|---|---|---|---|---|---|---|
| | | PIV-3 | | PIV-3 | | RSV | |
| Formulation | (ug) | 6 wk Bleed | 8 wk Bleed | 6 wk Bleed | 8 wk Bleed | 6 wk Bleed | 8 wk Bleed |
| Buffer | — | <1.0 ± 0.0 | <1.0 ± 0.0 | <1.0 ± 0.0 | <1.0 ± 0.0 | <1.0 ± 0.0 | <1.0 ± 0.0 |
| $F_{RSV}$-$HN_{PIV\text{-}3}$ | 10.0 | 9.1 ± 0.3 | 9.1 ± 0.3 | 7.1 ± 0.3 | 7.1 ± 0.5 | 5.5 ± 0.9 | 4.5 ± 1.2 |
| | 1.0 | 7.0 ± 2.0 | 7.3 ± 2.2 | 5.0 ± 1.5 | 4.5 ± 1.4 | 4.5 ± 0.5 | 3.0 ± 1.0 |
| Live PIV-3 | | 8.6 ± 0.7 | 7.3 ± 0.6 | 7.0 ± 0.4 | 7.3 ± 0.6 | N/A | N/A |
| Live RSV | | N/A[c] | N/A | N/A | N/A | 5.5 ± 1.5 | 5.0 ± 1.0 |

[a]Reciprocal mean $log_2$ serum dilution which inhibits erythrocyte agglutination by 4 hemagglutinating units of PIV-3

[b]Reciprocal mean $log_2$ serum dilution which blocks hemadsorption of 100 $TCID_{50}$ units of PIV-3 or RSV

[c]N/A—not applicable

TABLE 2

Serum antibody response of cotton rats immunized with the chimeric $F_{RSV}$-$HN_{PIV\text{-}3}$ protein[a]

| Antigen | Dose | HAI Titre[b] ($log_2$ ± s.d.) | | Neutralization Titre[c] ($log_2$ ± s.d.) | | | |
|---|---|---|---|---|---|---|---|
| | | PIV-3 | | PIV-3 | | RSV | |
| Formulation | (ug) | 4 wk Bleed | 5 wk Bleed | 4 wk Bleed | 5 wk Bleed | 4 wk Bleed | 5 wk Bleed |
| Buffer | — | 2.8 ± 0.5 | <3.0 ± 0.0 | <1.0 ± 1.0 | <1.0 ± 0.0 | 1.8 ± 0.3 | 0.8 ± 0.7 |
| $F_{RSV}$-$HN_{PIV\text{-}3}$ | 10.0 | 9.5 ± 1.3 | 10.5 ± 0.6 | >9.0 ± 0.0 | >9.0 ± 0.0 | 5.2 ± 1.1 | 5.8 ± 0.9 |
| | 1.0 | 9.3 ± 1.0 | 10.3 ± 0.5 | >9.0 ± 0.0 | >9.0 ± 0.0 | 5.0 ± 0.7 | 5.8 ± 1.2 |

TABLE 2-continued Serum antibody response of cotton rats immunized with the chimeric $F_{RSV}$-$HN_{PIV-3}$ protein[a]

| Antigen Formulation | Dose (ug) | HAI Titre[b] (log$_2$ ± s.d.) PIV-3 | | Neutralization Titre[c] (log$_2$ ± s.d.) PIV-3 | | RSV | |
|---|---|---|---|---|---|---|---|
| | | 4 wk Bleed | 5 wk Bleed | 4 wk Bleed | 5 wk Bleed | 4 wk Bleed | 5 wk Bleed |
| Live PIV-3 | | 7.0 ± 0.0 | 8.5 ± 0.7 | >9.0 ± 0.0 | 9.2 ± 0.7 | N/A | N/A |
| Live RSV | | N/A[d] | N/A | N/A | N/A | 5.5 ± 0.6 | 8.5 ± 0.6 |

[a]Each value represents the mean titre of antisera from 8 animals.
[b]Reciprocal mean log$_2$ serum dilution which inhibits erythrocyte agglutination by 4 hemagglutinating units of PIV-3
[c]Reciprocal mean log$_2$ serum dilution which blocks hemadsorption of 100 TCID$_{50}$ units of PIV-3 or RSV
[d]N/A—not applicable

TABLE 3

Response of immunized cotton rats to PIV/RSV challenge[a]

| Antigen Formulation | Dose (ug) | Mean virus lung titre log$_{10}$/g lung ± s.d. | |
|---|---|---|---|
| | | RSV | PIV-3 |
| Buffer | — | 3.7 ± 0.3 | 3.4 ± 0.3 |
| $F_{RSV}$-$HN_{PIV-3}$ | 10.0 | ≦1.5 ± 0.0 | ≦1.5 ± 0.0 |
| $F_{RSV}$-$HN_{PIV-3}$ | 1.0 | ≦1.5 ± 0.0 | ≦1.5 ± 0.0 |
| Live RSV | | ≦1.5 ± 0.0 | ≦1.5 ± 0.0 |
| Live PIV-3 | | ≦1.5 ± 0.0 | ≦1.5 ± 0.0 |

[a]Animals were challenged intranasally with 100 TCID$_{50}$ units of PIV-3 or RSV and killed 4 days later. Each value represents the mean virus lung titre of 4 animals.

What we claim is:

1. A multimeric hybrid gene encoding a chimeric protein including a protein from parainfluenza virus (PIV) and a protein from respiratory syncytial virus (RSV), comprising a nucleotide sequence encoding a PIV-3 F protein or a fragment thereof having fusion activity linked to a nucleotide sequence coding for a RSV G protein or a fragment thereof having attachment activity.

2. The hybrid gene of claim 1 which is of $F_{PIV3}$-$G_{RSV}$ hybrid gene.

3. The hybrid gene of claim 1 contained in an expression vector.

4. The hybrid gene of claim 3 in the form of a plasmid which is pD2F-G (ATCC 75389).

5. Eukaryotic cells containing the multimeric hybrid gene of claim 1 for expression of the chimeric protein encoded by the hybrid gene.

6. The cells of claim 5 which are mammalian cells, insect cells, yeast cells or fungal cells.

7. A vector for antigen delivery containing the gene of claim 1.

8. The vector of claim 7 which is viral vector.

9. The vector of claim 8 wherein said viral vector is selected from the group consisting of poxviral, adenoviral and retroviral viral vectors.

10. The vector of claim 7 which is a bacterial vector.

11. The vector of claim 10 wherein said bacterial vector is selected from salmonella and mycobacteria.

12. A process for the preparation of a chimeric protein including a protein from parainfluenza virus (PIV) and a protein from respiratory syncytial virus (RSV), which comprises:
    isolating a first nucleotide sequence encoding a PIV-3 F protein or a fragment thereof having fusion activities,
    isolating a second nucleotide sequence encoding a RSV G protein or a fragment thereof having attachment activity,
    linking said first and second nucleotide sequences to form a multimeric hybrid gene, and
    expressing the multimeric hybrid gene in a cellular expression system.

13. The process of claim 12 wherein said multimeric hybrid gene is $F_{PIV3}$-$G_{RSV}$ hybrid gene.

14. The process of claim 12 wherein said multimeric hybrid gene is contained in an expression vector which is p2DF-G (ATCC 75389).

15. The process of claim 12 wherein said cellular expression system is provided by mammalian cells, insect cells, yeast cells or fungal cells.

16. The process of claim 12 including separating a chimeric protein from a culture of said eukaryotic cellular expression and purifying the separated chimeric protein.

* * * * *